US008993599B2

(12) United States Patent
Hall et al.

(10) Patent No.: US 8,993,599 B2
(45) Date of Patent: Mar. 31, 2015

(54) PHARMACEUTICAL FORMULATIONS USEFUL FOR INHIBITING ACID SECRETION AND METHODS FOR MAKING AND USING THEM

(75) Inventors: Warren Hall, Del Mar, CA (US); Kay Olmstead, San Diego, CA (US); Laura Weston, Escondido, CA (US)

(73) Assignee: Santarus, Inc., Raleigh, NC (US)

( * ) Notice: Subject to any disclaimer, the term of this patent is extended or adjusted under 35 U.S.C. 154(b) by 465 days.

(21) Appl. No.: 11/338,608

(22) Filed: Jan. 24, 2006

(65) Prior Publication Data

US 2006/0204585 A1    Sep. 14, 2006

Related U.S. Application Data

(63) Continuation-in-part of application No. 10/893,203, filed on Jul. 16, 2004, now abandoned.

(60) Provisional application No. 60/488,321, filed on Jul. 18, 2003.

(51) Int. Cl.
| | |
|---|---|
| A61K 31/4439 | (2006.01) |
| A61K 9/20 | (2006.01) |
| A61K 33/10 | (2006.01) |
| A61K 9/00 | (2006.01) |
| A61K 47/02 | (2006.01) |
| A61K 9/28 | (2006.01) |
| A61K 9/48 | (2006.01) |
| A61K 9/50 | (2006.01) |
| A61K 33/00 | (2006.01) |
| A61K 33/06 | (2006.01) |
| A61K 45/06 | (2006.01) |

(52) U.S. Cl.
CPC .............. *A61K 9/0056* (2013.01); *A61K 47/02* (2013.01); *A61K 9/2009* (2013.01); *A61K 9/2081* (2013.01); *A61K 9/2846* (2013.01); *A61K 9/4808* (2013.01); *A61K 9/5047* (2013.01); *A61K 31/4439* (2013.01); *A61K 33/00* (2013.01); *A61K 33/06* (2013.01); *A61K 45/06* (2013.01); *Y10S 514/819* (2013.01); *Y10S 514/96* (2013.01); *Y10S 514/97* (2013.01)
USPC ........... 514/338; 514/819; 514/960; 514/970; 424/465; 424/717

(58) Field of Classification Search
CPC . A61K 31/4439; A61K 47/02; A61K 9/2009; A61K 9/2081; A61K 9/4808
See application file for complete search history.

(56) References Cited

U.S. PATENT DOCUMENTS

| | | | |
|---|---|---|---|
| 4,045,564 A | 8/1977 | Berntsson et al. | |
| 4,182,766 A | 1/1980 | Krasso et al. | |
| 4,255,431 A | 3/1981 | Junggren et al. | |
| 4,337,257 A | 6/1982 | Junggren et al. | |
| 4,359,465 A | 11/1982 | Ruwart | |
| 4,414,216 A | 11/1983 | Kawakita et al. | |
| 4,472,409 A | 9/1984 | Senn-Bilfinger | |
| 4,508,905 A | 4/1985 | Junggren et al. | |
| 4,544,750 A | 10/1985 | Brandstrom et al. | |
| 4,620,008 A | 10/1986 | Brandstrom et al. | |
| 4,628,098 A | 12/1986 | Nohara et al. | |
| 4,636,499 A | 1/1987 | Brandstrom et al. | |
| 4,689,333 A | 8/1987 | Nohara et al. | |
| 4,725,691 A | 2/1988 | Brandstrom et al. | |
| 4,738,974 A | 4/1988 | Brandstrom | |
| 4,786,505 A | 11/1988 | Lovgren et al. | |
| 4,808,596 A | 2/1989 | Matsuishi et al. | |
| 4,853,230 A | 8/1989 | Lovgren et al. | |
| 4,965,351 A | 10/1990 | Caruso et al. | |
| 4,985,548 A | 1/1991 | Caruso et al. | |
| 5,008,278 A | 4/1991 | Brandstrom et al. | |
| 5,013,743 A | 5/1991 | Iwahi et al. | |
| 5,019,584 A | 5/1991 | Brandstrom et al. | |
| 5,025,024 A | 6/1991 | Brandstrom et al. | |
| 5,026,560 A | 6/1991 | Makino et al. | |
| 5,039,806 A | 8/1991 | Brandstram et al. | |
| 5,045,321 A | 9/1991 | Makino et al. | |
| 5,075,323 A | 12/1991 | Fain et al. | |
| 5,093,132 A | 3/1992 | Makino et al. | |
| 5,093,342 A | 3/1992 | Tomoi et al. | |

(Continued)

FOREIGN PATENT DOCUMENTS

| | | |
|---|---|---|
| CA | 1234118 | 3/1988 |
| DE | 10061136 | 10/2002 |

(Continued)

OTHER PUBLICATIONS

Adams, S.P. et al., "Comments of the Report of "Association" of Omeprazole with DNA by Phillips et al.," Mutagenesis, 1992, pp. 395-396, vol. 7, No. 5, Oxford University Press.

Al-Assi, M.T. et al., "Treatment of *Helicobacter pylori* Infection with Omeprazole-Amoxicillin Combination Therapy Versus Rantidine/Sodium Bicarbonate-Amoxicillin," Am J. of Gastroenterology, 1995, pp. 1411-1414, vol. 90, No. 9.

Andersson, T. et al., "Pharmacokinetics of (14C) Omeprazole in Patients with Liver Cirrhosis," Clinical Pharmacokinetics, 1993, pp. 71-78, vol. 24, No. 1.

Andersson, T. et al., "Pharmacokinetics of Various Single Intravenous and Oral Doses of Omeprazole," Eur. J. of Clin. Pharma., 1990, p. 9. 195-197, vol. 39, No. 2.

(Continued)

*Primary Examiner* — Savitha Rao
*Assistant Examiner* — Gregg Polansky
(74) *Attorney, Agent, or Firm* — Novak Druce Connolly Bove + Quigg LLP

(57) ABSTRACT

In one general aspect of the present invention, pharmaceutical formulations comprising both a proton pump inhibitor microencapsulated or dry coated with a material that enhances the shelf-life of the pharmaceutical composition and one or more antacid are described. In another general aspect of the present invention, pharmaceutical formulations comprising both a proton pump inhibitor microencapsulated or dry coated with a taste-masking material and one or more antacid are described.

32 Claims, 10 Drawing Sheets

(56) References Cited

U.S. PATENT DOCUMENTS

| | | |
|---|---|---|
| 5,106,862 A | 4/1992 | Briving et al. |
| 5,124,158 A | 6/1992 | Ruwart et al. |
| 5,215,974 A | 6/1993 | Alminger et al. |
| 5,219,870 A | 6/1993 | Kim |
| 5,232,706 A | 8/1993 | Palomo Coll |
| 5,244,670 A | 9/1993 | Upson et al. |
| 5,246,714 A | 9/1993 | Dahlinder et al. |
| 5,288,506 A | 2/1994 | Spickett et al. |
| 5,374,730 A | 12/1994 | Slemon et al. |
| 5,385,739 A | 1/1995 | Debregeas et al. |
| 5,386,032 A | 1/1995 | Brandstrom |
| 5,391,752 A | 2/1995 | Hoermer et al. |
| 5,395,323 A | 3/1995 | Berglund |
| 5,399,700 A | 3/1995 | Min et al. |
| 5,417,980 A | 5/1995 | Goldman et al. |
| 5,430,042 A | 7/1995 | Lindberg et al. |
| 5,433,959 A | 7/1995 | Makino et al. |
| 5,447,918 A | 9/1995 | McCullough |
| 5,447,923 A | 9/1995 | Catrenich et al. |
| 5,464,632 A | 11/1995 | Cousin et al. |
| 5,470,983 A | 11/1995 | Slemon et al. |
| 5,504,082 A | 4/1996 | Kawakita et al. |
| 5,536,735 A | 7/1996 | Takechi et al. |
| 5,589,491 A | 12/1996 | Nakanishi et al. |
| 5,599,794 A | 2/1997 | Eek et al. |
| 5,629,305 A | 5/1997 | Eek et al. |
| 5,633,244 A | 5/1997 | Eek et al. |
| 5,635,520 A | 6/1997 | Uda |
| 5,639,478 A | 6/1997 | Makino et al. |
| 5,690,960 A | 11/1997 | Bengtsson et al. |
| 5,693,818 A | 12/1997 | Von Unge |
| 5,714,504 A | 2/1998 | Lindberg et al. |
| 5,714,505 A | 2/1998 | Hasselkus |
| 5,731,002 A | 3/1998 | Olovson et al. |
| 5,753,265 A | 5/1998 | Bergstrand et al. |
| 5,766,765 A | 6/1998 | Nelson |
| 5,798,120 A | 8/1998 | Tomohisa et al. |
| 5,814,338 A | 9/1998 | Veronesi |
| 5,817,338 A | 10/1998 | Bergstrand et al. |
| 5,824,339 A | 10/1998 | Shimizu et al. |
| 5,840,737 A | 11/1998 | Phillips |
| 5,846,562 A | 12/1998 | Yanai et al. |
| 5,876,759 A | 3/1999 | Gowan, Jr. |
| 5,877,192 A | 3/1999 | Lindberg et al. |
| 5,879,708 A | 3/1999 | Makino et al. |
| 5,883,102 A | 3/1999 | Hamley et al. |
| 5,885,594 A | 3/1999 | Nilsen et al. |
| 5,900,424 A | 5/1999 | Kallstrom et al. |
| 5,929,244 A | 7/1999 | Von Unge |
| 5,935,600 A | 8/1999 | Cherukuri et al. |
| 5,939,091 A | 8/1999 | Eoga et al. |
| 5,948,773 A | 9/1999 | Akiyama et al. |
| 5,948,789 A | 9/1999 | Larsson et al. |
| 5,955,107 A | 9/1999 | Augello et al. |
| 5,958,955 A | 9/1999 | Gustavsson et al. |
| 5,962,022 A | 10/1999 | Bolt et al. |
| 5,965,162 A | 10/1999 | Fuisz et al. |
| 5,972,389 A | 10/1999 | Shell et al. |
| 5,979,515 A | 11/1999 | Olsson |
| 5,997,903 A | 12/1999 | Dietrich et al. |
| 6,013,281 A | 1/2000 | Lundberg et al. |
| 6,017,560 A | 1/2000 | Makino et al. |
| 6,030,988 A | 2/2000 | Gilis et al. |
| 6,047,829 A | 4/2000 | Johnstone et al. |
| 6,090,827 A | 7/2000 | Erickson et al. |
| 6,123,962 A | 9/2000 | Makino et al. |
| 6,124,464 A | 9/2000 | Hogberg et al. |
| 6,132,770 A | 10/2000 | Lundberg |
| 6,132,771 A | 10/2000 | Depui et al. |
| 6,136,344 A | 10/2000 | Depui et al. |
| 6,143,771 A | 11/2000 | Lindberg et al. |
| 6,147,103 A | 11/2000 | Anousis et al. |
| 6,150,380 A | 11/2000 | Lovqvist et al. |
| 6,162,816 A | 12/2000 | Bohlin et al. |
| 6,166,213 A | 12/2000 | Anousis et al. |
| 6,169,102 B1 | 1/2001 | Kanamaru et al. |
| 6,183,776 B1 | 2/2001 | Depui et al. |
| 6,235,311 B1 | 5/2001 | Ullah et al. |
| 6,248,363 B1 | 6/2001 | Patel et al. |
| 6,262,085 B1 | 7/2001 | Whittle et al. |
| 6,262,086 B1 | 7/2001 | Whittle et al. |
| 6,268,385 B1 | 7/2001 | Whittle et al. |
| 6,274,173 B1 | 8/2001 | Sachs et al. |
| 6,284,271 B1 | 9/2001 | Lundberg et al. |
| 6,294,192 B1 | 9/2001 | Patel et al. |
| 6,299,904 B1 | 10/2001 | Shimizu et al. |
| 6,319,513 B1 | 11/2001 | Dobrozsi |
| 6,319,904 B1 | 11/2001 | Akiyama et al. |
| 6,328,993 B1 | 12/2001 | Linder et al. |
| 6,328,994 B1 | 12/2001 | Shimizu et al. |
| 6,365,180 B1 | 4/2002 | Meyer et al. |
| 6,432,381 B2 | 8/2002 | Liversidge et al. |
| 6,444,689 B1 | 9/2002 | Whittle et al. |
| 6,462,058 B1 | 10/2002 | Fujishima et al. |
| 6,489,346 B1 | 12/2002 | Phillips |
| 6,500,459 B1 | 12/2002 | Chhabra et al. |
| 6,551,621 B1 | 4/2003 | Debregeas et al. |
| 6,555,139 B2 | 4/2003 | Sharma |
| 6,569,453 B2 | 5/2003 | Linder et al. |
| 6,569,463 B2 | 5/2003 | Patel et al. |
| 6,572,900 B1 | 6/2003 | Zyck |
| 6,586,004 B2 | 7/2003 | Shimizu et al. |
| 6,608,092 B1 | 8/2003 | Fujishima et al. |
| 6,645,988 B2 | 11/2003 | Phillips |
| 6,664,276 B2 | 12/2003 | Fujishima et al. |
| 6,699,885 B2 | 3/2004 | Phillips |
| 6,740,339 B1 | 5/2004 | Ohkouchi et al. |
| 6,984,404 B1 * | 1/2006 | Talton et al. |
| 7,163,958 B2 | 1/2007 | Earl et al. |
| 2001/0009678 A1 | 7/2001 | Toshihiro et al. |
| 2001/0010825 A1 | 8/2001 | Shimizu et al. |
| 2001/0027192 A1 | 10/2001 | Akiyama et al. |
| 2001/0048946 A1 | 12/2001 | Ghebre-Sellassie |
| 2002/0012680 A1 | 1/2002 | Patel et al. |
| 2002/0025342 A1 | 2/2002 | Linder et al. |
| 2002/0039597 A1 | 4/2002 | Ukai et al. |
| 2002/0044960 A1 | 4/2002 | Cherukuri |
| 2002/0044962 A1 | 4/2002 | Cherukuri et al. |
| 2002/0068088 A1 | 6/2002 | Gruber |
| 2002/0142034 A1 | 10/2002 | Shimizu et al. |
| 2002/0146451 A1 | 10/2002 | Sharma et al. |
| 2002/0160046 A1 | 10/2002 | Robinson et al. |
| 2002/0192299 A1 | 12/2002 | Taneja et al. |
| 2003/0045724 A1 | 3/2003 | Fujishima et al. |
| 2003/0050620 A1 | 3/2003 | Odidi et al. |
| 2003/0088106 A1 | 5/2003 | Whittall et al. |
| 2003/0091630 A1 | 5/2003 | Louie-Helm et al. |
| 2003/0091643 A1 | 5/2003 | Friesen et al. |
| 2003/0096012 A1 | 5/2003 | Besse et al. |
| 2003/0096845 A1 | 5/2003 | Whittle et al. |
| 2003/0144306 A1 | 7/2003 | Phillips |
| 2003/0181487 A1 | 9/2003 | Kamiyama et al. |
| 2003/0191159 A1 * | 10/2003 | Phillips |
| 2003/0215527 A1 | 11/2003 | Phillips |
| 2003/0235628 A1 | 12/2003 | Taneja et al. |
| 2004/0005362 A1 | 1/2004 | Taneja |
| 2004/0006109 A1 | 1/2004 | Taneja |
| 2004/0018239 A1 | 1/2004 | Ishida et al. |
| 2004/0039027 A1 | 2/2004 | Kamiyama et al. |
| 2004/0048896 A1 | 3/2004 | Phillips |
| 2004/0048898 A1 | 3/2004 | Fujishima et al. |
| 2004/0049045 A1 | 3/2004 | Hashimoto et al. |
| 2004/0052854 A1 | 3/2004 | Yoshinari et al. |
| 2004/0058018 A1 | 3/2004 | Phillips |
| 2004/0081671 A1 | 4/2004 | Taneja |
| 2004/0081700 A1 | 4/2004 | Taneja |
| 2004/0082618 A1 | 4/2004 | Taneja |
| 2004/0082791 A1 | 4/2004 | Fujishima et al. |
| 2004/0097539 A1 | 5/2004 | Terashita et al. |
| 2004/0097555 A1 | 5/2004 | Ohkawa et al. |
| 2004/0121004 A1 | 6/2004 | Taneja |
| 2004/0131675 A1 | 7/2004 | Yamamoto et al. |
| 2004/0131676 A1 | 7/2004 | Taneja |
| 2004/0146559 A1 | 7/2004 | Sowden et al. |

(56) References Cited

U.S. PATENT DOCUMENTS

| | | |
|---|---|---|
| 2004/0170750 A1 | 9/2004 | Bunick et al. |
| 2004/0248942 A1 | 12/2004 | Hepburn et al. |
| 2005/0037070 A1 | 2/2005 | Hall et al. |
| 2005/0054682 A1 | 3/2005 | Phillips |
| 2005/0112192 A1 | 5/2005 | Qiu et al. |
| 2005/0266071 A1 | 12/2005 | Olmstead et al. |
| 2006/0039942 A1 | 2/2006 | Greten et al. |

FOREIGN PATENT DOCUMENTS

| | | |
|---|---|---|
| DE | 19752843 C2 | 1/2003 |
| EP | 0005129 A1 | 10/1979 |
| EP | 0005129 B1 | 4/1981 |
| EP | 0040639 A1 | 12/1981 |
| EP | 0040639 B1 | 5/1984 |
| EP | 0244380 A2 | 11/1987 |
| EP | 0247983 A2 | 12/1987 |
| EP | 0248634 A2 | 12/1987 |
| EP | 0308515 A1 | 3/1989 |
| EP | 0315964 A1 | 5/1989 |
| EP | 0394471 A1 | 10/1990 |
| EP | 0452697 A1 | 10/1991 |
| EP | 0465254 A1 | 1/1992 |
| EP | 0502556 B1 | 6/1992 |
| EP | 0237200 B1 | 7/1992 |
| EP | 0496437 A2 | 7/1992 |
| EP | 0496437 B1 | 7/1992 |
| EP | 0502556 A1 | 9/1992 |
| EP | 0244380 B1 | 1/1993 |
| EP | 0247983 B1 | 1/1993 |
| EP | 0315964 B1 | 1/1993 |
| EP | 0338861 B1 | 1/1993 |
| EP | 0248634 B1 | 7/1993 |
| EP | 0414847 B1 | 9/1993 |
| EP | 0565210 A2 | 10/1993 |
| EP | 0567201 A2 | 10/1993 |
| EP | 0567643 A1 | 11/1993 |
| EP | 0308515 B1 | 1/1994 |
| EP | 0436620 B1 | 8/1994 |
| EP | 0654471 A1 | 5/1995 |
| EP | 0565210 A3 | 6/1995 |
| EP | 0567201 A3 | 7/1995 |
| EP | 0452697 B1 | 12/1995 |
| EP | 0496437 A3 | 7/1996 |
| EP | 0652751 B1 | 10/1996 |
| EP | 0587659 B1 | 5/1997 |
| EP | 0654471 BI | 7/1998 |
| EP | 0567201 B1 | 9/1999 |
| EP | 0565210 B1 | 11/1999 |
| EP | 1004305 A1 | 5/2000 |
| EP | 0636364 B1 | 9/2000 |
| EP | 0696921 B1 | 2/2001 |
| ES | 2024993 A6 | 3/1992 |
| GB | 2189698 A | 11/1987 |
| JP | 45-039541 A | 12/1970 |
| JP | 45-039543 A | 12/1970 |
| JP | 46-009580 A | 3/1971 |
| JP | 46-009581 A | 3/1971 |
| JP | 48-103567 A | 12/1973 |
| JP | 49-005967 A | 1/1974 |
| JP | 49-013172 A | 2/1974 |
| JP | 49-020173 A | 2/1974 |
| JP | 49-020174 A | 2/1974 |
| JP | 49-041198 A | 4/1974 |
| JP | 49-093537 A | 9/1974 |
| JP | 49-095997 A | 9/1974 |
| JP | 50-052065 A | 5/1975 |
| JP | 50-112373 A | 9/1975 |
| JP | 50-142565 A | 11/1975 |
| JP | 51-016669 A | 2/1976 |
| JP | 51-131875 A | 11/1976 |
| JP | 52-005769 A | 1/1977 |
| JP | 51-017268 A | 2/1977 |
| JP | 52-014776 A | 2/1977 |
| JP | 52-097978 A | 8/1977 |
| JP | 52-102416 A | 8/1977 |
| JP | 53-059675 A | 5/1978 |
| JP | 55-019211 A | 2/1980 |
| JP | 56-061311 A | 5/1981 |
| JP | 59-095997 A | 6/1984 |
| JP | 61-221117 A | 10/1986 |
| JP | 62-145083 A | 6/1987 |
| JP | 62-258316 A | 11/1987 |
| JP | 62-258320 A | 11/1987 |
| JP | 62-277322 A | 12/1987 |
| JP | 62-283964 A | 12/1987 |
| JP | 02-22225 A | 1/1990 |
| JP | 03-34967 A | 2/1991 |
| JP | 03-48680 A | 3/1991 |
| JP | 03-52887 A | 3/1991 |
| JP | 03-163018 A | 7/1991 |
| JP | 05-117268 A | 5/1993 |
| JP | 05-104225 A | 8/1993 |
| JP | 05-194224 A | 8/1993 |
| JP | 05-194225 A | 8/1993 |
| JP | 05-255088 A | 10/1993 |
| JP | 05-294831 A | 11/1993 |
| JP | 06-092853 A | 4/1994 |
| JP | 06-100449 A | 4/1994 |
| JP | 07-033659 A | 2/1995 |
| JP | 09-087110 A | 3/1997 |
| JP | 10017470 A | 1/1998 |
| JP | 10017471 A | 1/1998 |
| JP | T-H11-501950 | 2/1999 |
| JP | T-H11-501951 | 2/1999 |
| JP | 2000-212180 A | 8/2000 |
| JP | A-2000-103731 | 10/2000 |
| JP | A-2000-302681 | 10/2000 |
| JP | 2000-355540 A | 12/2000 |
| JP | 2001-000406 | 1/2001 |
| JP | 2001040006 | 2/2001 |
| JP | T-2001-511443 | 8/2001 |
| JP | T-2002-534374 | 10/2002 |
| KR | 1996-0003605 B1 | 3/1996 |
| KR | 1996-0011238 B1 | 8/1996 |
| KR | 1996-0011390 B1 | 8/1996 |
| RO | 88351 | 4/1996 |
| WO | WO 89-00566 A1 | 1/1989 |
| WO | WO-92-04898 A1 | 4/1992 |
| WO | WO-92-08716 A1 | 5/1992 |
| WO | WO-95-07913 A1 | 3/1993 |
| WO | WO-93-05770 A1 | 4/1993 |
| WO | WO-94-00112 A1 | 1/1994 |
| WO | WO-94-02140 A1 | 2/1994 |
| WO | WO-94-02141 A1 | 2/1994 |
| WO | WO-95-01783 A1 | 1/1995 |
| WO | WO-95-15962 A1 | 6/1995 |
| WO | WO-95-23594 A1 | 9/1995 |
| WO | WO-95-32957 A1 | 12/1995 |
| WO | WO-95-32959 A1 | 12/1995 |
| WO | WO-96-01612 A1 | 1/1996 |
| WO | WO-96-01622 A1 | 1/1996 |
| WO | WO-96-01623 A1 | 1/1996 |
| WO | WO-96-01624 A1 | 1/1996 |
| WO | WO-96-01625 A1 | 1/1996 |
| WO | WO-96-02236 A1 | 2/1996 |
| WO | WO-96-16959 A1 | 6/1996 |
| WO | WO-96-24338 A1 | 8/1996 |
| WO | WO-96-24375 A1 | 8/1996 |
| WO | WO-96-38175 A1 | 12/1996 |
| WO | WO-97-02020 A1 | 12/1996 |
| WO | WO-97-02021 A1 | 1/1997 |
| WO | WO-97-09964 A1 | 3/1997 |
| WO | WO-97-25064 A1 | 7/1997 |
| WO | WO-97-25065 A1 | 7/1997 |
| WO | WO 97/25066 | 7/1997 |
| WO | WO-97-41114 A1 | 11/1997 |
| WO | WO-97-48380 A1 | 12/1997 |
| WO | WO-98-00114 A2 | 1/1998 |
| WO | WO-98-02368 A1 | 1/1998 |
| WO | WO-98-16228 A1 | 4/1998 |
| WO | WO-98-28284 A1 | 7/1998 |
| WO | WO-98-40054 A1 | 9/1998 |

(56) References Cited

FOREIGN PATENT DOCUMENTS

| | | |
|---|---|---|
| WO | WO 98-50019 A1 | 11/1998 |
| WO | WO-98-53803 A1 | 12/1998 |
| WO | WO-98-54171 A1 | 12/1998 |
| WO | WO-99-00380 A1 | 1/1999 |
| WO | WO-99-08500 A2 | 2/1999 |
| WO | WO-99-25323 A1 | 5/1999 |
| WO | WO-99-25711 A1 | 5/1999 |
| WO | WO-99-27917 A1 | 6/1999 |
| WO | WO-99-29320 A1 | 6/1999 |
| WO | WO-99-29299 A1 | 7/1999 |
| WO | WO-99-32091 A1 | 7/1999 |
| WO | WO-99-32093 A1 | 7/1999 |
| WO | WO-99-45004 A1 | 9/1999 |
| WO | WO-99-53918 A1 | 10/1999 |
| WO | WO-99-55705 A1 | 11/1999 |
| WO | WO-99-55706 A1 | 11/1999 |
| WO | WO 99-59544 | 11/1999 |
| WO | WO-00-01372 A2 | 1/2000 |
| WO | WO-00-09092 A1 | 2/2000 |
| WO | WO 00-10999 A2 | 3/2000 |
| WO | WO-00-10999 A3 | 3/2000 |
| WO | WO-00-15195 A1 | 3/2000 |
| WO | WO-00-26185 A2 | 5/2000 |
| WO | WO-00-27366 A1 | 5/2000 |
| WO | WO-00-28975 A2 | 5/2000 |
| WO | WO-00-28975 A3 | 5/2000 |
| WO | WO-0026185 A3 | 5/2000 |
| WO | WO-00-30612 A1 | 6/2000 |
| WO | WO-00-35448 A1 | 6/2000 |
| WO | WO-00-44744 A1 | 8/2000 |
| WO | WO-00-45817 A1 | 8/2000 |
| WO | WO-00-50038 A1 | 8/2000 |
| WO | WO-00-69438 A1 | 11/2000 |
| WO | WO-00-78293 A1 | 12/2000 |
| WO | WO-01-03707 A1 | 1/2001 |
| WO | WO-01-24782 A2 | 4/2001 |
| WO | WO 01/28559 A1 | 4/2001 |
| WO | WO-01-34573 A1 | 5/2001 |
| WO | WO-01-51050 A1 | 7/2001 |
| WO | WO 02/053097 | 7/2002 |
| WO | WO 02/072070 A1 * | 9/2002 |
| WO | WO 02/085889 A1 | 10/2002 |
| WO | WO-03-009846 A1 | 2/2003 |
| WO | WO-03-017980 A1 | 3/2003 |
| WO | WO-03-061584 A1 | 7/2003 |
| WO | PCT/US04/23044 | 4/2005 |

OTHER PUBLICATIONS

Andersson, T. et al., "Pharmacokinetics and Bioavailability of Omeprazole After Single and Repeated Oral Administration in Healthy Subjects," British J. of Clin. Pharma., 1990, pp. 557-563, vol. 29, No. 5.

Andersson, T., "Pharmacokinetics, Metabolism and Interactions of Acid Pump Inhibitors: Focus on Omeprazole, Lansoprazole and Pantoprazole," Clin. Pharacokinetics, 1996, pp. 9-28, vol. 31, No. I.

Andersson, T. et al., "Pharmacokietic Studies with Esomeprazole, the (S)-Isomer of Omeprazole," Clin. Pharmacokinetics, 2001, pp. 411-426, vol. 40, No. 6.

Arvidsson, T. et al., "Peak Distortion in the Column Liquid Chromatographic Determination of.Omeprazole Dissolved in Borax Buffer," J. of Chromatography, 1991, pp. 271-278, vol. 586, Part 2.

Balaban, D. et al., "Nasogastric Omeprazole: Effects on Gastric pH in Critically Ill Patients," Am. J. of Gastroenterology, 1997, pp. 79-83, vol. 92, No. I.

Ballard, E. et al., "Bioequivalence Between Lansoprazole Sachet for Suspension and Intact Capsule," Gastroenterology, 2001, pp. A-245, vol. 120, No. 5, Supp. 1, Abstract 1276.

Arturo Ballesteros, M. et al., "Bolus or Intravenous Infusion of Ranitidine: Effects on Gastric pH and Acid Secretion," Annals of Internal Medicine, 1990, pp. 334-339, Vo. 112.

Barie, P.S. and Hariri, R.J., "Therapeutic Use of Omeprazole for Refractory Stress-Induced Gastric Mucosal Hemorrage," Critical Care Medicine, 1992, pp. 899-901, vol. 20, No. 6.

Beekman, S.M., "Preparation and Properties of New Gastric Antacids I: Aluminum Hydroxide-Magnesium Carbonate Dried Gels," J. of the Am. Pharmaceutical Association, 1960, pp. 191-200, vol. 49.

Bennett, D.R. and Dickson, B.D. (eds.), "Gastrointestinal Drugs," Am Med. Assoc. Drug Eval., AMA, Chicago 1973, pp. 773-827, $2^{nd}$ ed., Publishing Sciences Group, Acton, Mass USA.

Blum, A.L., "Therapeutic Approach to Ulcer Healing," Am J. of Med., Aug. 1985, pp. 8-14, vol. 79, Supp. 2C.

Bone, R.C., "Let's Agree on Terminology: Definition of Sepsis," Critical Care Med., 1991, p. 27, vol. 19, No. 7.

Borrero, E. et al., "Antacids vs. Sucralfate in Preventing Acute Gastrointestinal Tract in Abdominal Aortic Surgery," Archives of Surgery, 1986, pp. 810-812, vol. 121.

Brunton, L.L., "Agents for Control of Gastric Activity and Treatment of Peptic Ulcers," The Pharmacologic Basis of Therapeutics, 1990, NY, p. 907.

Cantu, T.G. and Korek, J.S., "Central Nervous System Reactions to Histamine-2 Receptor Blockers," Annals of Int. Med., 1991, pp. 1027-1034, vol. 114.

Caos, A. et al., "Rabeprazole for the Prevention of Pathologic and Symptomatic Relapse of Erosive or Ulcerative Gastroesophageal Reflux Disease," Am. J. of Gastroenterolgy, 2000, pp. 3081-3088, vol. 95, No. 11.

Carroll et al., "Nasogastric Administration of Omeprazole for Control of Gastric pH," 10 World Congresses of Gastroenterolgy, 1994, Abstract 22P, vol. 2.

Cederberg, C. et al., "Omeprazole: Pharmacokinetics and Metabolism in Man," Scandinavian J. of Gastroenterology, 1989, pp. 33-40, vol. 24, Supp. 166.

Cederberg, C. et al., "Effect of Once Daily Intravenous and Oral Omeprazole on24-Hour Intragastric Acidity in Healthy Subjects," Scandinavian J. of Gastroenterology, 1993, pp. 179-184, vol. 28, No. 2.

Ching, C. and Lam, S., "Antacids-Indications and Limitations," Drugs, pp. 305-317, vol. 47, No. 2.

Cioffi, W.G. et al., "Comparison of Acid Neutralizing and Non-Acid Neutralizing Stress Ulcer Prophylaxis in Thermally Injured Patients," J. of Trauma, 1994, pp. 541-547, vol. 36, No. 4.

Cook, D.J. et al., "Nosocomial Pneumonia and the Role of Gastric pH: A Meta-Analysis," Chest, 1991, pp. 7-13, vol. 100, No. 1.

Cook, D.J. et al., "Risk Factors for Gastrointestinal Bleeding in Critically Ill Patients," N. Engl. J. of Med., Feb. 1994, pp. 377-381, vol. 330, No. 6.

Cook, D.J. et al., "Stress Ulcer Prophlaxis in the Critically Ill: A Meta-Analysis," Am. J. of Med., 1991, pp. 519-527, vol. 91.

Crill, C.M. et al., "Upper Gastrointestinal Tract Bleeding in Critically Ill Pediatric Patients," Pharmacotherapy, 1999, pp. 162-180, vol. 19, No. 2.

Czaja, A.J. et al., "Acute Gastroduodenal Disease After Thermal Injury: an Endoscopic Evaluation of Incidence and Natural History," N. Engl. J. of Med., Oct. 1974, pp. 925-929, vol. 291, No. 18.

Deakin, M. and Temple, J.G., "Therapeutic Process-Review XXXIII: Are We Making Progress in the Drug Treatment of Oesophageal Disease?", J. of Clin. Pharmacy and Therapeutics, 1988, pp. 365-374, vol. 13, No. 6.

Di Iorio, B. et al., "Aluminum and Phosphorus Urinary Excretion After Modifying Gastric Acid Secretion in Normal Subjects," Trace Elements and Electrolytes, 1996, pp. 47-49, vol. 13, No. 1.

Digiacinto, J.L. et al., "Stability of Suspension Formulations of Lansoprazole and Omeprazole Stored in Amber-Colored Plastic Oral Syringes," Annals of Pharmacotherapy, 2000, pp. 600-605, vol. 34, No. 5.

Doan, T.T. et al., "Comparative Pharmacokinetics and Pharmacodynamics of Lansoprazole Oral Capsules and Suspension in Healthy Subjects," Am. J. of Health-System Pharmacists, Aug. 2001, pp. 1512-1519, vol. 58, No. 16.

Dobkin, E.D. et al., "Does pH Paper Accurately Reflect Gastric pH?", Critical Care Medicine, 1990, pp. 985-988, vol. 18, No. 9.

Driks, M.R. et al., "Nosocomial Pneumonia in Intubated Patients Given Sucralfate As Compared with Antacids or Histamine Type 2 Blockers. The Role of Gastric Colonization," N. Engl. J. of Med., 1987, pp. 1376-1382, vol. 317.

(56) References Cited

OTHER PUBLICATIONS

Eisenberg, P.G. et al., Prospective Trial Comparing a Combination pH Probe-Nasogastric Tube with Aspirated Gastric pH in Intensive Care Unit Patients, Critical Care Med., 1990, pp. 1092-1095, vol. 18.
Ekpe, A. and Jacobsen, T., "Effect of Various Salts on the Stability of Lansoprazole, Omeprazole, and Pantoprazole as Determined by High-Performance Liquid Chromatography," Drug Dev. And Industrial Pharmacy, 1999, pp. 1057-1065; vol. 25, No. 9.
Elliot, R., "Nasogastric Administration of Omeprazole," Australian J. of Hosp. Pharmacy, 1998, pp. 174-176, vol. 28, No. 3.
Fabian, T.C. et al., "Pneumonia and Stress Ulceration in Severely Injured Patients. A Prospective Evaluation of the Effects of Stress Ulcer Prophylaxis," Feb. 1993, Archives of Surgery, pp. 185-192, vol. 128.
Fellenius, E. et al., "Substituted Benzimidazoles Inhibit Gastric Acid Secretion by Blocking (H+ + K+)ATPase," Nature, Mar. 1981, pp. 159-162, vol. 290.
Fiddian-Green, R.G. et al., "Predictive Value of Intramural pH and Other Risk Factors for Massive Bleeding from Stress Ulceration," Gastroenterology, 1983, pp. 613-620, vol. 85.
Fryklund et al., "Function and Structure of Parietal Cells After H+-K+-ATPase Blockade," Am. J. of Physiology, 1988, pp. G399-407, vol. 254, No. 3, Pt. I.
Fuchs, C., "Antacids: Their Function, Formulation, and Evaluation," Drug and Cosmetic Industry, Jun. 1949, vol. 64, No. 6, pp. 692-773.
Gafter, U. et al., "Thrombocytopenia Associated With Hypersensitivity to Rantidinc: Possible Cross-Reactivity with Cimetidine," Am. J. of Gastroenterology, 1989, pp. 560-562, vol. 84, No. 5.
Garner, J.S. et al., "CDC Definitions for Nosocomial Infections, 1988," Am J. of Infection Control, 1988, pp. 128-140, vol. 16.
Garnett, W.R., "Efficacy, Safety, and Cost Issues in Managing Patients with Gastroesophael Reflux Diseases," Am. J. of Hosp. Pharmacy, 1993, pp. 511-518, vol. 50, Supp.1.
Gray et al., "Influence of Insulin Antibodies on Pharmacokinetics and Bioavailability of Recombinant Human and Highly Purified Beef Insulins in Insulin Dependent Diabetes," Br. Med. J., Jun. 1985, pp. 1687-1690, vol. 290.
Hardy, P. et al., "Inhibition of Gastric Secretion by Omeprazole and Efficiency of Calcium Carbonate on the Control of Hyperphosphatemia in Patients on Chronic Hemodialysis," Art. Organs, 1998, pp. 569-573, vol. 22, No. 7.
Hatlebakk, J.G. et al., "Lansoprazole Capsules and Amoxicillin Oral Suspension in the Treatment of Peptic Ulcer Disease," Scandinavian J. of Gastroenterology, 1995, pp. 1053-1057, vol. 30, No. 11.
Heath et al., "Intragastric pH Measurement Using a Novel Disposable Sensor," Intensive Care Med., 1988, pp. 232-235, vol. 14.
Hixson et al., "Current Trends in the Pharmacotherapy for Gastroesophageal Reflux Disease," Arch. Intern. Med., 1992, pp. 117-723, vol. 152, No. 4.
Hixson et al., "Current Trends in the Pharmacotherapy for Peptic Ulcer Disease," Arch. Intern. Med., 1992, pp. 726-732, vol. 152, No. 4.
Holbert, J.M. et al., "A Study of Antacid Buffers: The Time Factor in Neutralization of Gastric Acidity," J. of Am Pharmaceut. Assoc. (Scientific Edition), 1947, pp. 149-151, vol. 36.
Holt, S. and Howden, C.W., "Omeprazole, Overview and Opinion," Dig. Diseases and Sciences, 1991, pp. 385-393, vol. 36. No. 4.
Horn, J., "The Proton-Pump Inhibitors: Similarities and Differences," Clinical Therapeutics, 2000, pp. 266-280, vol. 22, No. 3.
Howden, C.W. et al., "Oral Pharmacokinetics of Omeprazole," Eur. J. of Clin. Pharmacology, pp. 641-643, vol. 26.
Humphries, T.J. and Merritt, G.J., "Review Article: Drug Interactions with Agents Used to Treat Acid-Related Diseases," Alimentary Pharmacol. & Therapeutics, 1999, pp. 18-26, vol. 13, Supp 3.
Jungnickel, P.W., "Pantoprazole: A New Proton Pump Inhibitor," Clin. Therapeutics, 2000, pp. 1268-1293, vol. 22, No. 11.
Karol, M.D. et al., "Pharmacokinetics of Lansoprazole in Hemodialysis Patients," J. of Clin. Pharmacology, 1995, pp. 815-820, vol. 35.

Kihira, K. et al., "Endoscopic Topical Therapy for the Treatment of *Helicobacter pylori* Infection," J. of Gastroenterology, 1996, pp. 66-68, vol. 31, Supp. IX.
Kiilerich, S. et al., "Effect of Intravenous Infusion of Omeprazole and Rantidine on Twenty-Four Hour Intragastric pH in Patients with Duodenal Ulcer," Digestion, 1995, pp. 25-30, vol. 56.
Korponay-Szabo, I.R. et al., "High Acid Buffering Capacity of Protein Hydrolysate Infant Forumulas," J. of Pediatric Gastroenterology & Nutrition, Aug. 2000, vol. 31, Supp.2, Abstract 956.
Kromer, W. et al., "Differences in pH-Dependent Activation Rate of Substituted Benzimidazoles and Biological in vitro Correlates," Pharmacol., 1998, pp. 57-70, vol. 56.
Kromer, W., "Similarities and Differences in the Properties of Substituted Benzimidazoles: A Comparison Between Pantoprzole and Related Compounds," Digestion, 1995, pp. 443-454, vol. 56, No. 6.
Laggner, A. N. et al., "Prevention of Upper Gastrointestinal Bleeding in Long Term Ventilated Patients," Am. J. of Med., 1989, pp. 81-84, vol. 86, Supp. 6A.
Landahl, S. et al., "Pharmacokinetic Study of Omeprazole in Elderly Healthy Volunteers," Pharmacokinetics, 1992, pp. 496-476, vol. 23, No. 6.
Larson, G.M. et al., "Gastric Response to Severe Head Injury," Am. J. of Surgery, 1984, pp. 97-105, vol. 147.
Larson, C. et al., "Bioavailability and Efficacy of Omeprazole Given Orally and by Nasogastric Tube," Digestive Diseases and Science, 1996, pp. 475-479, vol. 41, No. 3.
Larsson, H. et al., "Gastric Acid Antisecretory Effect of Two Different Dosage of Omeprazole During Prolonged Oral Treatment in the Gastric Fistula Dog,", Canadian J. of Gastroenterology, 1988, pp. 1013-1019, vol. 23, No. 8.
Lasky, M., "A Prospective Study of Omeprazole Suspension to Prevent Clinically Significant Gastrointestinal Bleeding from Stress Ulcers in Mechanically Ventilated Trauma Patients," J. of Trauma: Injury, Infection and Critical Care, 1998, pp. 527-533, vol. 44, No. 3.
Lin, M. et al., "Evaluation of Buffering Capacity and Acid Neutralizing pH Time Profile of Antacids," J. of Formosan Med. Assoc., 1998, pp. 704-710, vol. 97, No. 10.
Lind, C. et al., "Inhibition of Basal and Betazole-and-sham-feeding induced Acid Secretion by Omeprazole in Man," Scandinavian J. of Gastroenterology, 1986, pp. 1004-1010, vol. 21.
Lockhart, S.P. and Baxter, G., "A Lansoprazole Suspension Formulation as an Alternative to Capsules for Oral Administration," World Congresses of Gastroenterology, 1998, p. 226, vol. 59 Supp. 3, Abstract ExhA2074.
Londong, W. et al., "Dose-Response Study of Omeprazole on Meal-Stimulated Gastric Acid Secretion and Gastrin-Release," 1983, Gastroenterology, pp. 1373-1378, vol. 85, No. 6.
Maconi, G. et al., "Prolonging Proton Pump Inhibitor-Based Anti-*Helicobacer pylori* Treatment from One to Two Weeks in Duodenal Ulcer: Is It Worthwhile?", Digest of Liver Disease, 2000, pp. 275-280, vol. 32.
Marrone, G.C. and Silen, W., "Pathogenesis, Diagnosis and Treatment of Acute Gastric Mucosal Lesions," 1984, Clinics in Gastroenterology, pp. 635-650, vol. 13, No. 2.
Martin, L.F. et al., "Continuous Intravenous Cimetidine Decreases Stress-Related Upper Gastrointestinal Hemorrage Without Promoting Pneumonia," Critical Care Med., 1993, pp. 19-39, vol. 21, No. 1.
Martin, L.F. et al., "Stress Ulcers and Organ Failure in Intubated Patients in Surgical Intensive Care Unites," Ann. Of Surgery, 1992, pp. 332-337, vol. 215, No. 4.
Maxwell, S.L. et al., "Control of Gastric pH in a Critical Care Unit: Physician Behavior and Pharmacologic Effectiveness," Am. Rev. of Respiratory Disease, 1991, pp. A482, vol. 143, No. 4 (Part 2).
McAndrews, K.L. and Eastham, J.H., "Omeprazole and Lansoprazole Suspensions for Nasogastric Administration," Am. J. of Health-System Pharmacy, 1999, pp. 81, vol. 56.
McTavish, D. et al., "Omeprazole: An Updated Review of its Pharmacology and Therapeutic Use in Acid-Related Disorders," Drugs, 1991, pp. 138-170, vol. 41, No. 1.
Meiners, D. etal., "Evaluation of Various Techniques to Monitor Intragastric pH," Arch. Of Surgery, 1982, pp. 288-291, vol. 117.

(56) References Cited

OTHER PUBLICATIONS

Mohiuddin, M.A. et al., "Effective Gastric Acid Suppression After Oral Administration of Enteric-Coated Omeprazole Granules," Digestive Diseases and Sciences, 1997, pp. 715-719, vol. 42, No. 4.

Nakagawa, A. et al., "Lansoprazole: Phase I Study of Lansoprazole(AB-1749) Antiulcer Agent," Abstract in English, Text in Japanese, 1991, pp. 33-34.

Nakamura, M. et al., "Effect of Combined Administration of Lansoprazole and Sofalcone on Microvascular and Connective Tissue Regeration after Ethanol-Induced Mucosal Damage," J. of Clin. Gastroenterology, 1998, pp. S170-S177, vol. 27, Supp.1.

Naunton, M. et al., "Overuse of Proton Pump Inhibitors," J. of Clin. Pharmacy and Ther., 2000, pp. 333-340, vol. 25.

Oh, M.S. and Carroll, H.J., "Electrolyte and Acid-Base Disorders," The Pharmacologic Approach to the Critically Ill Patient, 1994, pp. 957-968, $3^{rd}$ Ed., Williams & Wilkins, Baltimore, MD, USA.

Oosterhuis, B. and Jonkman, J.H.G., "Omeprazole: Pharmacology, Pharmacokinetics and Interactions," Digestions, 1989, pp. 9-17, vol. 44, Supp. 1.

Osler, P. et al., "Effect of Omeprazole on the Phosphate-Binding Capacity of Calcium Carbonate," Nephron, 1995, pp. 89-90, vol. 69.

Ostro, M.J. et al., "Control of Gastric pH with Cimetidine: Boluses Versus Primed Infusions," Gastroenterology, 1985, pp. 532,537, vol. 89, No. 3.

Paul, J. et al., "Pantoprozole Bicarbonate Suspension (PBS) Provides Oral Bioavailability Comparable to Tablet," Critical Care Med. 2001, $30^{th}$ Int'l Educational & Scientific Symposium, A563.

Peckman, H.J., "Alternative Method for Administering Proton-Pump Inhibitors Through Nasogastric Tubes," Am. J. of Health Systems Pharmacy, 1999, pp. 1020, vol. 56.

Peura, D.A. and Johnson, L.F., "Cimetidine for Prevention and Treatment of Gastroduodenal Mucosal Lesions in Patients in an Intensive Care Unit," Ann. Of Int. Med., 1985, pp. 173-177, vol. 103, No. 2.

Phillips, J. and Metzler,M., "Simplified Omeprazole Solution for the Prophylaxis of Stress-Related Mucosal Damage in Critically Ill Patients," Critical Care Med. 1994, p. A53, vol. 22, No. 1.

Phillips, J.O. et al., "A Prospective Study of Simplified Omeprazole Suspension for the Prophylaxis of Stress-Related Mucosal Damage," Crictial Care Med. 1996, pp. 1793-1800, vol. 24, No. 11.

Phillips, J.O. et al., "The Stability of Simplified Omeprazole Suspension (SOS)," Critical Care Med., 1998, p. A101, vol. 26, No. 1 (Supp.), Abstract No. 221.

Phillips, J.O. et al., "A Multicenter, Prospective, Randomized Clinical Trial of Continuous Infusion I. V. Rantidine vs. Omeprazole Suspension in the Prophylaxid of Stress Ulcers," Crititcal Care Med., 1998, pp. A101, vol. 26, No. 1.(Supp.), Abstract No. 222.

Phillips, J.O., "The Stability of Simplified Lansoprazole Suspension (SLS)," Gastroenterology, Abstract G0382, vol. 116, No. 4.

Pickworth, K.K. et al., "Occurrence of Nasocomial Pneumonia in Mechanically Ventilated Trauma Patients: A Comparison of Sucralfate and Ranitidine," Critical Care Med., 1993, pp. 1856-1862, vol. 21, No. 12.

Pilbrant, A. and Cederberg, C. et al., "Development of an Oral Forumulation of Omeprazole," Scandinavian J. of Gastroenterology, 1985, pp. 113-120, vol. 20, Supp. 108.

Pilbrant, A., "Principles for Development of Antacids," Scandinavian J. of Gastroenterology, 1982, pp. 32-36, vol. 75.

Pipkin, G.A. and Mills, J.G., "Onset of Action of Antisecretory Drugs: Beneficial Effects of a Rapid Increasein Intragastric pH in Acid Reflux Disease," Scandinavian J. of Gastroenterology, 1999, pp. 3-8, Supp. 230.

Prichard, P.J. et al., Omeprazole: A Study of its Inhibition of Gastric pH andOral Pharmacokinetics After Morning or Evening Dosage,: Gastroenterology, 1985, pp. 64-69, vol. 88.

Priebe,H. and Skillman, J.J., "Methods of Prophylaxis in Stress Ulcer Disease," World J. of Surgery, 1981, pp. 223-233, vol. 5, No. 2.

Quercia, R.A. et al., "Stability of Omeprazole in an Extemporaneously Prepared Oral Liquid," Am. J. of Health System Pharmacy, 1997, pp. 1833-1836, vol. 54, No. 16.

Regardh, C.G. et al., "The Pharmacokinetics of Omeprazole inHumans—A Study of Single and Oral Doses," Ther. Drug Monitoring, 1990, pp. 163-172, vol. 12, No. 2.

Regardh et al., "Pharmacokinetics and Metabolism of Omeprazole in Animals and Man—An Overview," Scandinavian J. of Gastroenterology, Supp., 1985, pp. 79-84, vol. 108.

Rodrigo, J.M. and Ponce, J., "Therapeutic Approach to Peptic Ulcer-Relapse," Methods and Findings in Experimental and Clinical Pharmacology, 1989, pp. 131-135, vol. 11, Supp. I.

Roy, P.K. et al., "Zollinger-Ellison Syndrome-Clinical Presentation in 261 Patients," Medicine, 2000, pp. 379-411, vol. 79, No. 6.

Ryan, P. et al., "Nosocomial Pneumonia During Stress Ulcer Prophylaxis with Cimetidine and Sucralfate," 1993, Arch. Of Surgery, pp. 1353-1357, vol. 128.

Sax, M.J., "Clinically Important Adverse Effects and Drug Interactions with H2-Receptor Antagonists: An Update," Pharmacotherapy, 1987, pp. 110S-115S, vol. 7., No. 6, Part 2.

Schepp, W., "Stress Ulcer Prophylaxis: Still a Valid Option in the 1990s?", Digestion, 1993, pp. 189-199, vol. 54.

Schmassmann, A. et al., "Antacid Provides Better Restoration of Glandular Structures Within the Gastric Ulcer Scar than Omeprazole," Gut, 1994, pp. 869-904, vol. 35, No. 7.

Schmassmann, A. et al., "Antacids in Experimental Gastric Ulcer Healing: Pharmacokinetics of Aluminum and Quality of Healing," Eur. J. of Gastroenterology & Hepatology, 1993, pp. S111-S116, vol. 5, Supp. 3.

Shuman, R.B. et al., "Prophylactic Therapy for Acute Ulcer Bleeding: A Reappraisal,", Ann. Of Int. Med., 1987, pp. 562-567, vol. 106.

Schuster, D.P., "Stress Ulcer Prophylaxis: In Whom? With What?," Critical Care Med, 1993, vol. 21.

Sechet, A. et al., "Role of the Time of Administration of Calcium Carbonate in the Control of Hyperphophemia in Patients on Maintenance Hemodialysis," Nephrologie, 1999, pp. 209-212, vol. 20, No. 4.

Sechet, A. et al., "Inhibition of Gastric Secretion by Omeprazole and Efficacy of Calcium Carbonate in the Control of Hyperphosphatemia in Patients on Maintenance Hemodialysis," Nephrologie, 1888, pp. 213-216, vol. 20, No. 4.

Sharma, V.K. et al., "The Effects on Intragastric Acidity of Per-Gastrostomy Administration of an Alkaline Suspension of Omeprazole," Alimentary Pharmacology & Therapeutics, 1999, pp. 1091-1095, vol. 13.

Sharma, V.K. et al., "Oral Pharmacokinetics of Omeprazole and Lansoprazole After Single and Repeated Doses as Intact Capsules or as Suspensions in Sodium Bicarbonate," Alimentary Pharmacology & Therapeutics, 2000; pp. 887-892, vol. 14, No. 7.

Sharma,V.K. et al., The Pharmacodynamics of Lansoprazole Administered via Gastrostomy as Intact, Non-Encapsulate Granules, Alimentary Pharmacology & Therapeutics, 1998, pp. 1171-1174, vol. 12.

Sharma, V.K. et al., Simplified Lansoprazole Suspension—A Liquid Formulation of Lansoprazole-Effectively Suppress Intragastric Acidity when Administered Through a Gastrostomy, Am. J. of Gastroenterology, 1999, pp. 1813-1817, vol. 94, No. 7.

Sharma, V.K., "Comparison of 24-Hour Intragastric pH Using Four Liquid Formulations of Lansoprazole and Omeprazole," Am J. of Health System Pharmacy, 1999, p. S180-S21, vol. 56, Supp. 4.

Sharma, V.K. et al., "Effect on 24-Hour Intragastric Acidity of Simplifie Omeprazole Solution (SOS) Administered via Gastrostomy," Am. J. of Gastroenterolgy, 1997, p. 1625, vol. 92, No. 9 Abstract #169.

Sharma,V.K., "Simplified Lansoprazole Suspension (SLS): A Proton Pump Inhibitor PPI) in a Liquid Formulation that Works," Am. J. of Gastroenterology, Sep. 1998, pp. 1647, Abstract #153.

Siepler, J.K. et al., Selecting Drug Therapy for Patients with Duodenal Ulcers, Clin. 1990, pp. 463-467, vol. 9, No. 6.

Siepler, J.K., "A Dosage Alternative for H-2 Receptor Antagonists, Continuous-Infusion," Clin. Therapeutics, 1986, pp. 24-33, vol. 8, Supp. A.

Sih, J.C. et al., "Studies on (H(+)-K+)-ATPase Inhibitors of Gastric Acid Secretion, Prodrugs of 2-[(2-Pyridinlymethyl)sulfinyl] benzimidazole Proton-pump Inhibitors," J. of Med. Chem. 1991, pp. 1049-1062, vol. 34, No. 3.

(56) References Cited

OTHER PUBLICATIONS

Simms, H. et al., "Role of Gastric Colonization in the Development of Pneumonia in Critically Ill Trauma Patients: Results of a Prospective Randomized Trial," J. of Trauma, 1991, pp. 531-537, vol. 31, No. 4.
Skillman, J.J. et al., "Respiratory Failure, Hypotension, Sepsis and Jaundice: A Clinical Syndrom Associated with Lethal Hemorrhage from Acute Stress Ulceration of the Stomach," Am. J. of Surgery, 1969, pp. 523-530, vol. 117.
Skillman, J.J. et al., "The Gastric Mucosal Barrier: Clinical and Experimental Studies in Critically Ill and Normal Man, and in the Rabbit," Ann. Of Surgery, 1970, 564-584, vol. 172,No. 4.
Smythe, M.A. and Zarowitz, B.J., "Changing Perspectives of Stress Gastritis Prophylaxis," Ann. Of Pharmocotherapy, 1994, pp. 1073-1085, vol. 28.
Spencer, C.M. and Faulds, D., "Esomeprazole," Drugs, Aug. 2000, pp. 321-329, vol. 60, No. 2.
Spychal, R.T. and Wickman, N.W.R., "Thrombocytopenia Associated with Rantidine," Br. Med. J., 1985, p. 1687, vol. 291.
Stratford, M.R. L. et al., "Nicoltinamide Pharmacokinetics in Humans: Effect of Gastric Acid Inhibition, Comparison of Rectal vs. Oral Administration and the Use of Saliva for Drug Monitoring," Br. J. of Cancer, 1996, pp. 16-21, vol. 74, No. 1.
Tabata, T. et al., "Stabilization of a New Antiulcer Drug (Lansoprazole) in the Solid Dosage Forms," Drug Dev. & Industrial Pharmacy, 1992, pp. 1437-1447, vol. 18, No. 3.
Takeuchi, K. et al., "Effects o Pantoprazole, a novel H+/K+-ATPase Inhibitor, on Duodenal Ulcerogenic and Healing Responses in Rats: A Comparative Study with Omeprazole and Lansoprazole," J. of Gastroenterology & Hepatology, 1999, pp. 251-257, vol. 14, No. 3.
Tanaka, M. et al., "Differntial Stereoselective Pharmacokinetics of Pantoprazole, a Proton Pump Inhibitor in Extensive and Poor Metabolizers of Pantoprazole—A Preliminary Study," Chirality, 1997, pp. 17-21, vol. 9.
Tanaka, H. et al., "Pathogenesis of the Earliest Epithilial Cell Damage by Mepirizole and Cysteamine in the Rat Duodenum," Jap. J. of Pharmacology, 1989, pp. 509-519, vol. 51, No. 4.
Thomson, A.B.R., "Are the Orally Administered Proton Pump Inhibitors Equivalent? A Comparison of Lansoprazole, Omeprazole, Pantoprazole, and Rabeprazole," Curr. Gastroenterology Reports, 2000, pp. 482-492, vol. 2.
Tryba, M., "Risk of Acute Stress Bleeding and Nosocomial Pneumonia in Ventilated Intensive Care Patients, Sucralfate vs. Antacids," Am. J. of Med., 1987, pp. 117-124, vol. 87, Supp. 3B.
Tryba, M., "Stress Ulcer Prophylaxis-Quo Vadis?", Intensive Care Med., 1994, pp. 311-313, vol. 20.
Tytgat, G.n. J., "Drug Therapy of Reflux Oesophagitis: An Update," Scandinavian J. of Gastroentereology, 1989, pp. 38-49, vol. 24, Supp. 168.
Vial, T. et al., "Side Effects of Rantidine," Drug Safety, 1991, pp. 94-117, vol. 6, No. 2.
Vincent, J. et al., Concurrent Administration of Omeprazole and Antacid Does Not Alter the Pharmacokinetics of Doetilide in Healthy Subjects, Clin. Pharmacology & Therapeutics, 1996, p. 182, vol. 59, No. 2, Abstract P11-93.
Wade, L.G., Organic Chemistry, 1987, pp. 349-350, Prentice-Hall, Inc.,NJ, USA.
Walan, A, "Pharmacological Agents for Peptic Ulcer Disease," Scandinavian J. of Gastroenterology, Supp. 1984, p. 1, vol. 19, No. 98.
Wallmark, B. et al., "The Relationship Between Gastric Acid Secretion and Gastric H+/K+ATPase Activity," J. of Biol. Chem., 1985, 13681-13684, vol. 260, No. 25.
Watanabe, K. et al., "Pharmocokinetic Evaluation of Omeprazole Suspension Following Oral Administration in Rats: Effect of Neutralization of Gastric Acid," Acta Medica Okayama, 1996, pp. 219-222, vol. 50, No. 4.
Wilder-Smith, C.H. and Merki, H.S., "Tolerance During Dosing with H2 Receptor Antagonists, An Overview," 1991, Scandinavian J. of Gastroenterology, pp. 14-19, vol. 27, Supp. 193.
Whipple, J. et al., "The Effect of Omeprazole/Sodium Bicarbonate Solutiom Administration on the Accuracy of Subsequent pH Measurements through the Nasogastric Tube," Critical Care Med., 1995, pp. A69, vol. 28, No. 1 (Supp.).
Yamakawa, T. et al., "Synthesis and Structure-Activity Relationships of Substituted 2-(2-Imidazolysufinylmethyl) anilines as a New Class of Gastric H+/K(+)-ATPase Inhibitors. II.," Chem. And Pharmacuetical Bulletin, 1992, pp. 675-682, vol. 40, No. 3.
Yasuda, S. et al., "Antacids Have No Influence of the Pharmacokietics of Raberprazole, A New Proton Pump Inhibitor, in Healthy Volunteers," Intl. J. of Clin. Pharmacology & Therapeutics, 1999, pp. 249-253, vol. 37, No. 5.
Zinner, M.J. et al, "The Prevention of Gastro-Intestinal Tract Bleeding in Patients in an Intensive Care Unit," Surgery, Gynecology & Obstetrics, pp. 214-220, vol. 153.
"Agents for Control of Gastric Acidity and Treatement of Peptic Ulcers," Chapter 37, pp. 907-909.
"Buffered and Isotonic Solutions," Physical Pharmacy, pp. 169-189, Chapter 8.
Phillips, J.O. et al., "A Randomized, Pharmacokinetic and Pharmacodynamic, Cross-Over Study of Duodenal or Jejunal Administration Compared to Nasogastric Administration of Omeprazole Suspension in Patients at Risk for Stress Ulcers," American Journal of Gastroenterology (2001),vol. 96, No. 2, pp. 367-372.
PCT/US07/80641 Search Report dated Jul. 29, 2008.
Farup et al., "The Impact of Nocturnal Symptoms Associated with Gastroesophageal Reflux Disease on Health-Related Quality of Life," Arch Intern Med. 161:45-52 (2001).
"Pharmacotherapy Related Outcomes Group Researching Effective Stress Ulcer Strategies," Overview of Omeprazole Suspension 2000 Presentation, 14 pages.
CA 2,531,564 Office Action dated Nov. 27, 2012.
Dialog patent search re: omeprazole & specific coating, May 27, 2003, 154 pages.
Dialog patent search re: omeprazole & specific coating, May 29, 2003, 59 pages.
Dialog patent search re: omeprazole & specific coating, U.S. patents bibliographic titles, claims, abstracts only, May 30, 2003, p. 1-211.
Dialog search re: orneprazole & specific coaling, EP, PCT full text tiles, May 30, 2003, p, 212-804.
Metzler, M., "Advances in the Use of PPI's from Efficacy to Effectiveness." Presentation: Simplified Omeprazole Suspension, 1999, 4 pages.
Nerac search re: omeprazole and (opadry or HPMC), Question No. 1116119.016, May 2003, 47 pages.
Nerac search re: orneprimie and thocel (ETC), Question No. 1116119.014, May 2003, 38 pages.
Nerac search re: omeprazole and ethocel, Question No. 1116119.015, May 2003, 3 pages.
Nerac search re: omeprazole and kollicoat IR, Question No. 1116119.011, May 2003, 2 pages.
Nerac search re: omeprazole and RDI00, Question No. 1116119.017, May 2003, 12 pages.
Nerac search re: omeprazole/microencapsulation/HP, Question No. 1116119.008, May 2003, 13 pages.
Nerac search re: Omeprazole or Proton Pump Inhibitor and Coating (negate enteric), Question No. 1116119.009, May 2003, 57 pages.
Phillips, "Simplified Omeprazole Solution—(S.O.S.)—Pharmacokinetic/Pharmacodynamic Study in Patients at Risk for Stress Related Mucosal Damage (SRMD)," Project #5122, 1994, 6 pages.
Phillips, D.H., "Interaction of Omeprazole with DNA in Rat Tissues," Mutagenesis, 1992, pp. 277-283, vol. 7, No. 4.
Phillips, J., "Overview of Omeprazole Suspension—From Efficacy to Effectiveness Alternative Dosing of PPI's," 1998, Presentation, 5 pages.
Phillips, J., "Overview of Omeprazole Suspension—Problems with Administering Granules," 1999/2000 Presentation, 3 pages.
Phillips, J., "Simplified Omeprazole Suspension (SOS)," 1998, Presentation, 6 pages.
Phillips, J., "Stress-Related Mucosal Damage Optimizing Drug Therapy in the 1990's," Presentation at U. of MO. Surgical Society Scientific Program, 1994, 6 pages.

(56) References Cited

OTHER PUBLICATIONS

Phillips, J., "Stress-Related Mucosal Damage—Optimizing Drug Therapy," Presentation 1997, 5 pages.
Phillips, J., "Update on Acid-Related Disorders—Optimizing Pharmacotherapy for the 1990's," Presentation 1996, 6 pages.
Re, M.I., "Microencapsulation by spray drying", Drying Technology: An International Journal, 16(6): 1195-1236, 1998.

Vippagunta et al., "Crystalline solids," Advanced Drug Delivery Review 48 (2001) 3-26.

* cited by examiner

Prilosec, SAN-15A, SAN-15B and SAN-15C PK Data

SEM of Omeprazole and eAPI

Ome (5000X)

eAPI/Klucel (3000X)

PK Clinical Data - 40 mg, Day 1

SAN-15 Chewable Tablet 20 mg vs. Prilosec® Capsule 20 mg Day 1 Dosing

SAN-15 Chewable Tablet 40 mg vs. Prilosec® Capsule 40 mg
Day 1 Dosing

SAN-15 Chewable Tablet 20 mg vs. Prilosec® Capsule 20 mg Day 7 Dosing

Cmax vs. Tmax for SAN-15 ChewTab (20 mg and 40 mg) and Prilosec® Day 7 Dosing

Cmax vs. Tmax for SAN-15 ChewTab (20 mg and 40 mg) and Prilosec® Day 1 vs Day 7 Dosing

PHARMACEUTICAL FORMULATIONS USEFUL FOR INHIBITING ACID SECRETION AND METHODS FOR MAKING AND USING THEM This application is a continuation-in-part of U.S. patent application Ser. No. 10/893,203, filed on Jul. 16, 2004, which claims benefit under 35 U.S.C. § 119(e) of U.S. Provisional Application No. 60/488,321, filed Jul. 18, 2003; the contents of these applications are incorporated by reference herein in their entirety.

FIELD OF THE INVENTION

The present invention is related to pharmaceutical formulations comprising an antacid and a proton pump inhibitor microencapsulated with (1) a material that enhances the shelf-life of the composition, and/or (2) a taste-masking material. Also provided herein are pharmaceutical compositions comprising proton pump inhibitor and antacid wherein the proton pump inhibitor is dry coated. In addition, methods for manufacture of the pharmaceutical formulations; uses of the pharmaceutical formulations in treating disease; and combinations of the pharmaceutical formulations with other therapeutic agents are described.

BACKGROUND OF THE INVENTION

Upon ingestion, most acid-labile pharmaceutical compounds must be protected from contact with acidic stomach secretions to maintain their pharmaceutical activity. To accomplish this, compositions with enteric-coatings have been designed to dissolve at a pH to ensure that the drug is released in the proximal region of the small intestine (duodenum), rather than the acidic environment of the stomach. However, due to the pH-dependent attributes of these enteric-coated compositions and the uncertainty of gastric retention time, in-vivo performance as well as both inter- and intra-subject variability are all major set backs of using enteric-coated systems for the controlled release of a drug.

Phillips et al. has described non-enteric coated pharmaceutical compositions. These compositions, which allow for the immediate release of the pharmaceutically active ingredient into the stomach, involve the administration of one or more buffering agents with an acid labile pharmaceutical agent, such as a proton pump inhibitor. The buffering agent is thought to prevent substantial degradation of the acid labile pharmaceutical agent in the acidic environment of the stomach by raising the pH. See, e.g., U.S. Pat. Nos. 5,840,737; 6,489,346; 6,645,988; and 6,699,885; and U.S. patent application Ser. No. 10/898,135.

A class of acid-labile pharmaceutical compounds that are administered as enteric-coated dosage forms are proton pump inhibiting agents. Exemplary proton pump inhibitors include, omeprazole (Prilosec®), lansoprazole (Prevacid®), esomeprazole (Nexium®), rabeprazole (Aciphex®), pantoprazole (Protonix®), pariprazole, tentaprazole, and leminoprazole. The drugs of this class suppress gastrointestinal acid secretion by the specific inhibition of the $H^+/K^+$-ATPase enzyme system (proton pump) at the secretory surface of the gastrointestinal parietal cell. Most proton pump inhibitors are susceptible to acid degradation and, as such, are rapidly destroyed as pH falls to an acidic level. Therefore, if the enteric-coating of these formulated products is disrupted (e.g., trituration to compound a liquid, or chewing the capsule or tablet) or the buffering agent fails to sufficiently neutralize the gastrointestinal pH, the drug will be exposed to degradation by the gastrointestinal acid in the stomach.

Omeprazole is one example of a proton pump inhibitor which is a substituted bicyclic aryl-imidazole, 5-methoxy-2-[(4-methoxy-3,5-dimethyl-2-pyridinyl)methyl]sulfinyl]-1H-benzimidazole, that inhibits gastrointestinal acid secretion. U.S. Pat. No. 4,786,505 to Lovgren et al. teaches that a pharmaceutical oral solid dosage form of omeprazole must be protected from contact with acidic gastrointestinal juice by an enteric-coating to maintain its pharmaceutical activity and describes an enteric-coated omeprazole preparation containing one or more subcoats between the core material and the enteric-coating.

Proton pump inhibitors are typically prescribed for short-term treatment of active duodenal ulcers, gastrointestinal ulcers, gastro esophageal reflux disease (GERD), severe erosive esophagitis, poorly responsive symptomatic GERD, and pathological hypersecretory conditions such as Zollinger Ellison syndrome. These above-listed conditions commonly arise in healthy or critically ill patients of all ages, and may be accompanied by significant upper gastrointestinal bleeding.

It is believed that omeprazole, lansoprazole and other proton pump inhibiting agents reduce gastrointestinal acid production by inhibiting $H^+/K^+$-ATPase of the parietal cell during the final common pathway for gastrointestinal acid secretion. See, e.g., Fellenius et al., Substituted Benzimidazoles Inhibit Gastrointestinal Acid Secretion by Blocking $H^+/K^+$-ATPase, *Nature*, 290: 159-161 (1981); Wallmark et al., The Relationship Between Gastrointestinal Acid Secretion and Gastrointestinal $H^+/K^+$-ATPase Activity, *J. Biol. Chem.*, 260: 13681-13684 (1985); and Fryklund et al., Function and Structure of Parietal Cells After $H^+/K^+$-ATPase Blockade, *Am. J. Physiol.*, 254 (1988).

Proton pump inhibitors have the ability to act as weak bases which reach parietal cells from the blood and diffuse into the secretory canaliculi. There the drugs become protonated and thereby trapped. The protonated compound can then rearrange to form a sulfenamide which can covalently interact with sulfhydryl groups at critical sites in the extra cellular (luminal) domain of the membrane-spanning $H^+/K^+$-ATPase. See, e.g., Hardman et al., *Goodman & Gilman's The Pharmacological Basis of Therapeutics*, 907 (9th ed. 1996). As such, proton pump inhibitors are prodrugs that must be activated to be effective. The specificity of the effects of proton pump inhibiting agents is also dependent upon: (a) the selective distribution of $H^+/K^+$-ATPase; (b) the requirement for acidic conditions to catalyze generation of the reactive inhibitor; and (c) the trapping of the protonated drug and the cationic sulfenamide within the acidic canaliculi and adjacent to the target enzyme. See, e.g., Hardman et al.

Still, there remains a need for a pharmaceutical formulation that releases a proton pump inhibitor into the gastrointestinal tract for absorption of an intact, non-acid degraded or non-acid reacted form of a proton pump inhibitor into the bloodstream of a subject in either a fed or fasted state which exhibits enhanced shelf-life stability and improved patient compliance. The discussion that follows discloses pharmaceutical formulations comprising microencapsulated or dry coated proton pump inhibitors and one or more antacids which help to fulfill these needs.

SUMMARY OF THE INVENTION

Figure 1:
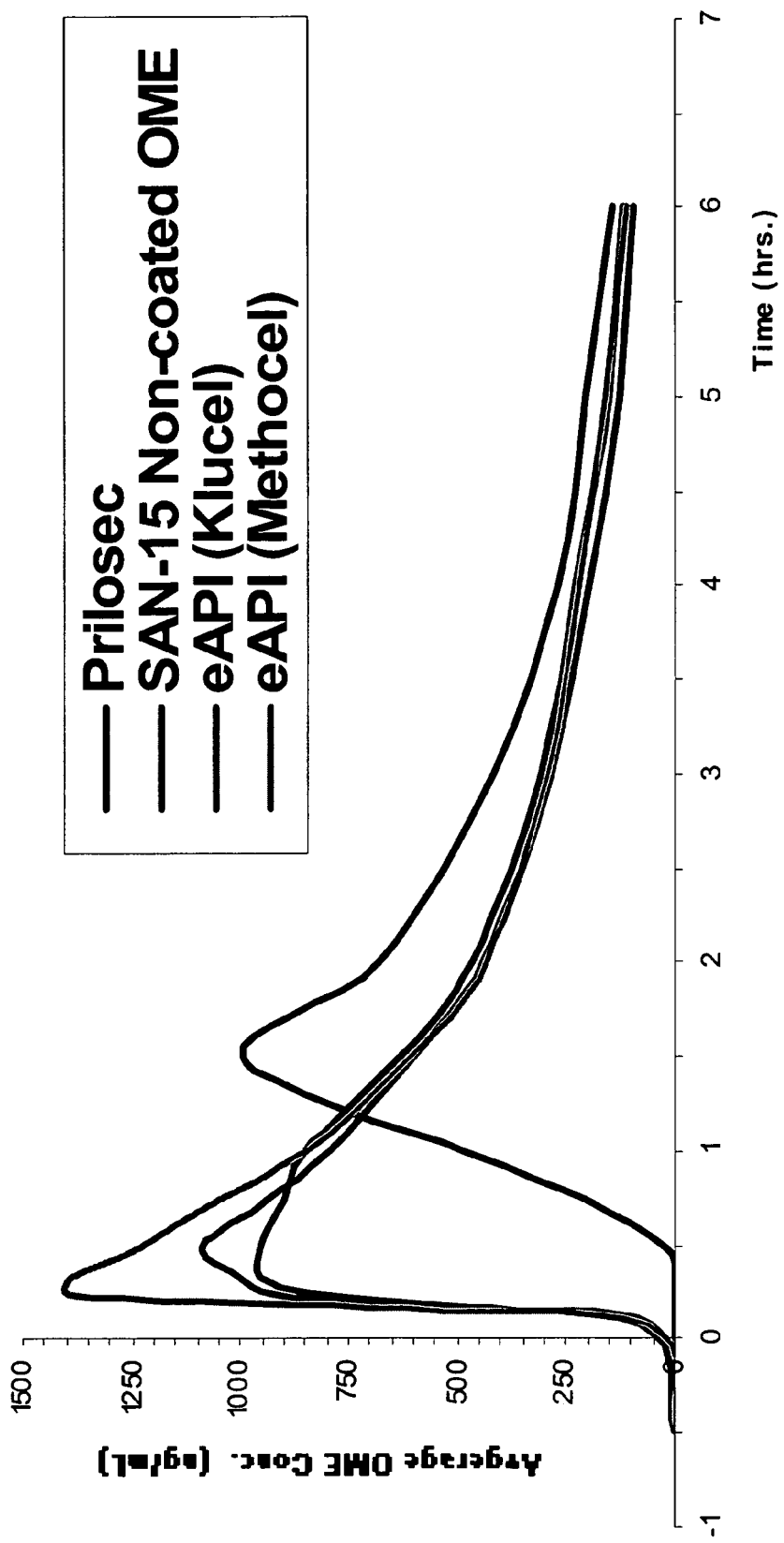
FIG. 1 is a graph comparing the pharmacokinetic release profiles of omeprazole of Prilosec®, non-microencapsulated omeprazole with antacid (as described in Example 13B), omeprazole microencapsulated with Klucel and antacid tablet (as described in Example 13C), and omeprazole microencapsulated with Methocel and antacid tablet (as described in Example 13D) in human.
Figure 2A:
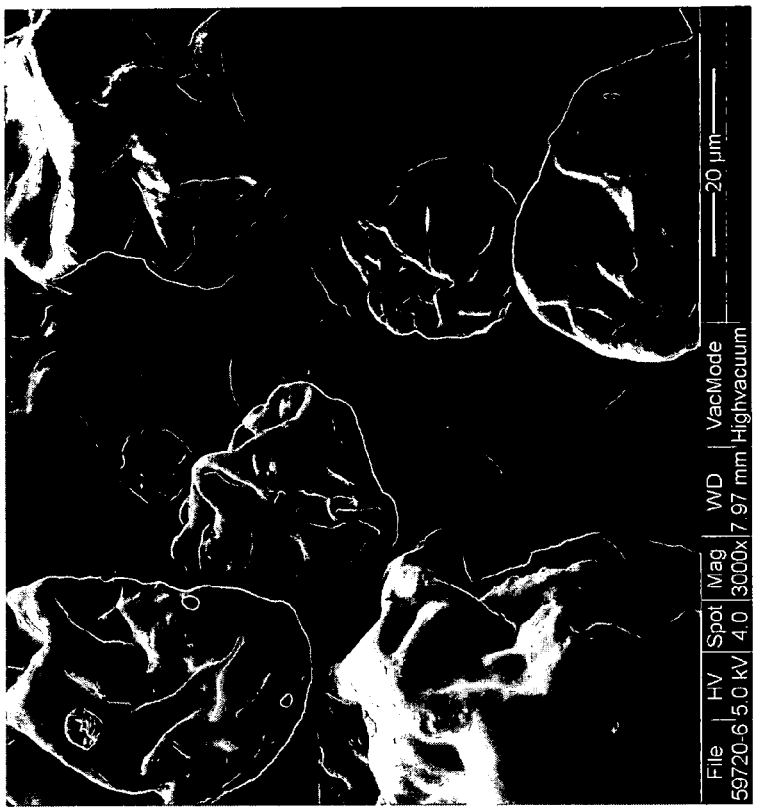
FIGS. 2A and 2B are SEM micrographs of micronized omeprazole and omeprazole microencapsulated with Klucel® Hydroxypropyl Cellulose.
Figure 2B:
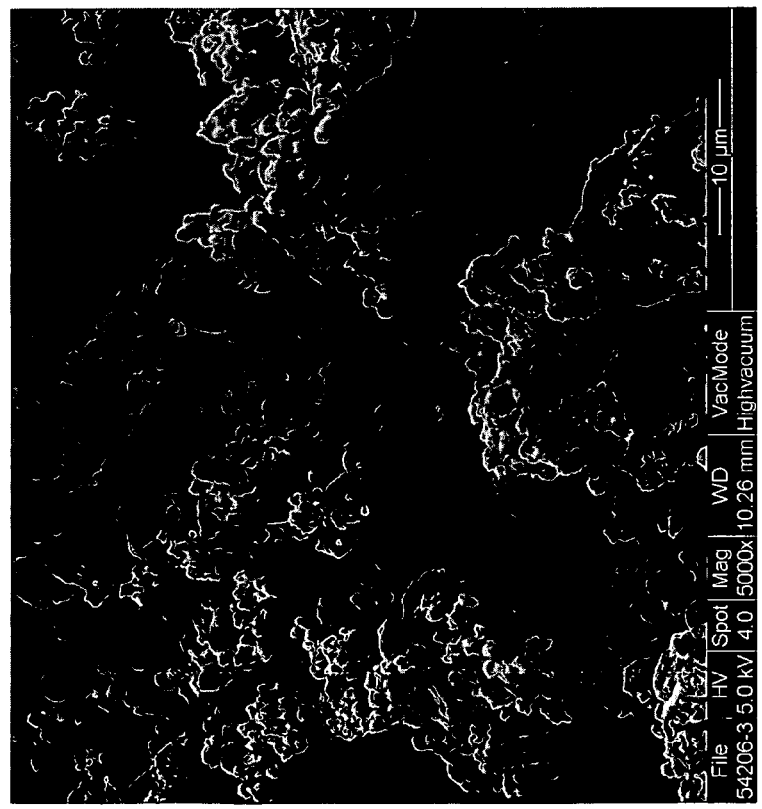

Provided herein are pharmaceutical formulations having enhanced shelf-lives comprising, at least one acid labile proton pump inhibitor which is microencapsulated with a material that enhances the shelf-life of the pharmaceutical formulation and at least one antacid; wherein an initial serum concentration of the proton pump inhibitor is greater than about 0.1 µg/ml at any time within about 30 minutes after administration of the pharmaceutical formulation. Also provided herein are taste-masked pharmaceutical formulations comprising at least one acid labile proton pump inhibitor which is microencapsulated with a taste-masking material and at least one antacid; wherein an initial serum concentration of the proton pump inhibitor is greater than about 0.1 µg/ml at any time within about 30 minutes after administration of the pharmaceutical formulation.

In various embodiments provided herein, the proton pump inhibitor is microencapsulated with one or more compounds selected from cellulose hydroxypropyl ethers; low-substituted hydroxypropyl ethers; cellulose hydroxypropyl methyl ethers; methylcellulose polymers; ethylcelluloses and mixtures thereof; polyvinyl alcohol; hydroxyethylcelluloses; carboxymethylcelluloses and salts of carboxymethylcelluloses; polyvinyl alcohol and polyethylene glycol co-polymers; monoglycerides; triglycerides; polyethylene glycols, modified food starch, acrylic polymers; mixtures of acrylic polymers with cellulose ethers; cellulose acetate phthalate; sepifilms, cyclodextrins; and mixtures thereof.

In various embodiments provided herein, the proton pump inhibitor is microencapsulated with one or more additives to enhance the processing or performance of microencapsulation. Such additives maybe pH modifier, plastersizer, antioxidant, or sweetener or flavor.

Provided herein are pharmaceutical formulations having enhanced shelf-lives comprising, at least one acid labile proton pump inhibitor and at least one antacid; wherein an initial serum concentration of the proton pump inhibitor is greater than about 0.1 µg/ml at any time within about 30 minutes after administration of the pharmaceutical formulation, wherein some or all of the proton pump inhibitor is dry coated.

In other embodiments, the at least one antacid comprises at least one soluble antacid. In some embodiments, the soluble antacid is sodium bicarbonate. In various embodiments, the at least one buffer is selected from sodium bicarbonate, calcium carbonate, sodium carbonate, magnesium oxide, magnesium hydroxide, magnesium carbonate, aluminum hydroxide, and mixtures thereof.

Provided herein are methods of extending the shelf-life of pharmaceutical formulations comprising microencapsulating at least one acid labile proton pump inhibitor with a material that enhances the shelf-life; and combining the microencapsulated acid labile proton pump inhibitor with at least one antacid. Also provided herein are methods of masking the taste of a pharmaceutical formulation comprising microencapsulating at least one acid labile proton pump inhibitor with a taste-masking material; and combining the microencapsulated acid labile proton pump inhibitor with an antacid.

Also provided herein are methods of making a pharmaceutical formulation with and extended shelf-life by dry coating the proton pump inhibitor. In some embodiments, the proton pump inhibitor is combined with some or all of the antacid to form a slug or sheet of material. This intermediate product is then broken into granular material with is combined with other components present in the pharmaceutical formulation. In other embodiments, the dry coated proton pump inhibitor is combined with additional antacid.

In various embodiments of the present invention, the pharmaceutical formulations may further comprise one or more excipients selected from parietal cell activators, organic solvents, erosion facilitators, diffusion facilitators, antioxidants, flavoring agents and carrier materials selected from binders, suspending agents, disintegration agents, filling agents, surfactants, solubilizers, stabilizers, lubricants, wetting agents, diluents, anti-adherents, and antifoaming agents.

DETAILED DESCRIPTION OF THE INVENTION

The present invention is directed to pharmaceutical formulations exhibiting enhanced shelf-life stability and/or improved taste masking properties useful for the treatment of a disease, condition or disorder. Methods of treatment using the pharmaceutical formulations of the present invention are also described.

It has been discovered that pharmaceutical compositions comprising (1) an acid labile proton pump inhibitor which is microencapsulated with a material that enhances the shelf-life of the pharmaceutical composition together with (2) one or more antacid, provide superior performance by enhancing shelf-life stability of the pharmaceutical formulation during manufacturing and storage.

It has also been discovered that pharmaceutical compositions comprising (1) an acid labile proton pump inhibitor which has been dry coated and (2) one or more antacids, provide superior performance by enhancing shelf-life stability of the pharmaceutical formulation during manufacturing and storage. In some embodiments, the proton pump inhibitor is dry coated with some or all of the antacid. In other embodiments, the dry coated proton pump inhibitor is combined with a second antacid which can be the same antacid as used to dry coat the proton pump inhibitor or a different antacid. In some embodiments, the dry coated material is combined with one or more pharmaceutical excipients. In yet other embodiments, the proton pump inhibitor is dry coated with a material comprising antacid, sweetener(s), lubricant, and binder.

Certain taste-masking materials have also been discovered which, when used in the pharmaceutical formulations provide (1) more palatable forms of the drug by blocking the contact of the unpleasant taste of the pharmaceutical agent from the contact of the taste receptor, thereby increasing patient compliance; and/or (2) require lower amounts of traditional flavoring agents.

To more readily facilitate an understanding of the invention and its preferred embodiments, the meanings of terms used herein will become apparent from the context of this specification in view of common usage of various terms and the explicit definitions of other terms provided in the glossary below or in the ensuing description.

Glossary

As used herein, the terms "comprising," "including," and "such as" are used in their open, non-limiting sense.

The term "about" is used synonymously with the term "approximately." Illustratively, the use of the term "about" indicates that values slightly outside the cited values, i.e. dosages comprising plus or minus 0.1% to 10%, which are also effective and safe. As one of ordinary skill in the art would understand, such dosages are thus encompassed by the scope of the claims reciting the terms "about" and "approximately."

The phrase "acid-labile pharmaceutical agent" refers to any pharmacologically active drug subject to acid catalyzed degradation.

"Aftertaste" is a measurement of all sensation remaining after swallowing. Aftertaste can be measured, e.g., from 30 seconds after swallowing, 1 minutes after swallowing, 2 minutes after swallowing, 3 minutes after swallowing, 4 minutes after swallowing, 5 minutes after swallowing, and the like.

"Amplitude" is the initial overall perception of the flavors balance and fullness. The amplitude scale is 0-none, 1-low, 2-moderate, and 3-high.

"Anti-adherents," "glidants," or "anti-adhesion" agents prevent components of the formulation from aggregating or sticking and improve flow characteristics of a material. Such compounds include, e.g., colloidal silicon dioxide such as Cab-o-sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, e.g., butylated hydroxytoluene (BHT), sodium ascorbate, and tocopherol.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Bioavailability" refers to the extent to which an active moiety, e.g., drug, prodrug, or metabolite, is absorbed into the general circulation and becomes available at the site of drug action in the body. Thus, a proton pump inhibitor administered through IV is 100% bioavailable. "Oral bioavailability" refers to the extent to with the proton pump inhibitor is absorbed into the general circulation and becomes available at the site of the drug action in the body when the pharmaceutical formulation is taken orally.

"Bioequivalence" or "bioequivalent" means that the area under the serum concentration time curve (AUC) and the peak serum concentration ($C_{max}$) are each within 80% and 125% with a 90% confidence interval.

"Carrier materials" include any commonly used excipients in pharmaceutics and should be selected on the basis of compatibility with the proton pump inhibitor and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Character notes" include, e.g., aromatics, basis tastes, and feeling factors. The intensity of the character note can be scaled from 0-none, 1-slight, 2-moderate, or 3-strong.

A "derivative" is a compound that is produced from another compound of similar structure by the replacement of substitution of an atom, molecule or group by another suitable atom, molecule or group. For example, one or more hydrogen atom of a compound may be substituted by one or more alkyl, acyl, amino, hydroxyl, halo, haloalkyl, aryl, heteroaryl, cycloaolkyl, heterocycloalkyl, or heteroalkyl group to produce a derivative of that compound.

"Diffusion facilitators" and "dispersing agents" include materials that control the diffusion of an aqueous fluid through a coating. Exemplary diffusion facilitators/dispersing agents include, e.g., hydrophilic polymers, electrolytes, Tween® 60 or 80, PEG and the like. Combinations of one or more erosion facilitator with one or more diffusion facilitator can also be used in the present invention.

"Diluents" increase bulk of the composition to facilitate compression. Such compounds include e.g., lactose; starch; mannitol; sorbitol; dextrose; microcrystalline cellulose such as Avicel®; dibasic calcium phosphate; dicalcium phosphate dihydrate; tricalcium phosphate; calcium phosphate; anhydrous lactose; spray-dried lactose; pregelatinzed starch; compressible sugar, such as Di-Pac® (Amstar); mannitol; hydroxypropylmethylcellulose; sucrose-based diluents; confectioner's sugar; monobasic calcium sulfate monohydrate; calcium sulfate dihydrate; calcium lactate trihydrate; dextrates; hydrolyzed cereal solids; amylose; powdered cellulose; calcium carbonate; glycine; kaolin; mannitol; sodium chloride; inositol; bentonite; and the like.

The term "disintegrate" includes both the dissolution and dispersion of the dosage form when contacted with gastrointestinal fluid.

"Disintegration agents" facilitate the breakup or disintegration of a substance. Examples of disintegration agents include a starch, e.g., a natural starch such as corn starch or potato starch, a pregelatinized starch such as National 1551 or Amijel® or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

"Drug absorption" or "absorption" refers to the process of movement from the site of administration of a drug toward the systemic circulation, e.g., into the bloodstream of a subject.

"Dry coating" is a method of coating the proton pump inhibitor with one or more other components without using water or other solvents.

"Dry granulation" is a method of converting powder particles into granules using the application of pressure without the use of a liquid.

An "enteric coating" is a substance that remains substantially intact in the stomach but dissolves and releases the drug once the small intestine is reached. Generally, the enteric coating comprises a polymeric material that prevents release in the low pH environment of the stomach but that ionizes at a slightly higher pH, typically a pH of 4 or 5, and thus dissolves sufficiently in the small intestines to gradually release the active agent therein.

The "enteric form of the proton pump inhibitor" is intended to mean that some or most of the proton pump inhibitor has been enterically coated to ensure that at least some of the drug is released in the proximal region of the small intestine (duodenum), rather than the acidic environment of the stomach.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" or "sweeteners" useful in the pharmaceutical compositions of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Gastrointestinal fluid" is the fluid of stomach secretions of a subject or the saliva of a subject after oral administration of a composition of the present invention, or the equivalent thereof. An "equivalent of stomach secretion" includes, e.g., an in vitro fluid having similar content and/or pH as stomach secretions such as a 1% sodium dodecyl sulfate solution or 0.1N HCl solution in water.

"Half-life" refers to the time required for the plasma drug concentration or the amount in the body to decrease by 50% from its maximum concentration.

"Lubricants" are compounds that prevent, reduce or inhibit adhesion or friction of materials. Exemplary lubricants include, e.g., stearic acid; calcium hydroxide; talc; sodium stearyl fumerate; a hydrocarbon such as mineral oil, or hydrogenated vegetable oil such as hydrogenated soybean oil (Sterotex®); higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol or a methoxypolyethylene glycol such as Carbowax™, sodium oleate, glyceryl behenate, polyethylene glycol, magnesium or sodium lauryl sulfate, colloidal silica such as Syloid™, Carb-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, of a therapeutic agent that is absorbed into the bloodstream after administration. One of ordinary skill in the art would be able to measure the serum concentration or plasma concentration of a proton pump inhibitor or other therapeutic agent. See, e.g., Gonzalez H. et al., *J. Chromatogr. B. Analyt. Technol. Biomed. Life Sci.*, vol. 780, pp 459-65, (Nov. 25, 2002).

"Parietal cell activators" or "activators" stimulate the parietal cells and enhance the pharmaceutical activity of the proton pump inhibitor. Parietal cell activators include, e.g., chocolate; alkaline substances such as sodium bicarbonate; calcium such as calcium carbonate, calcium gluconate, calcium hydroxide, calcium acetate and calcium glycerophosphate; peppermint oil; spearmint oil; coffee; tea and colas (even if decaffeinated); caffeine; theophylline; theobromine; amino acids (particularly aromatic amino acids such as phenylalanine and tryptophan); and combinations thereof.

"Pharmacodynamics" refers to the factors that determine the biologic response observed relative to the concentration of drug at a site of action.

"Pharmacokinetics" refers to the factors that determine the attainment and maintenance of the appropriate concentration of drug at a site of action.

"Plasma concentration" refers to the concentration of a substance in blood plasma or blood serum of a subject. It is understood that the plasma concentration of a therapeutic agent may vary many-fold between subjects, due to variability with respect to metabolism of therapeutic agents. In accordance with one aspect of the present invention, the plasma concentration of a proton pump inhibitors and/or other therapeutic agent may vary from subject to subject. Likewise, values such as maximum plasma concentration ($C_{max}$) or time to reach maximum serum concentration ($T_{max}$), or area under the serum concentration time curve (AUC) may vary from subject to subject. Due to this variability, the amount necessary to constitute "a therapeutically effective amount" of proton pump inhibitor or other therapeutic agent, may vary from subject to subject. It is understood that when mean plasma concentrations are disclosed for a population of subjects, these mean values may include substantial variation.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, and triacetin.

"Prevent" or "prevention" when used in the context of a gastric acid related disorder means no gastrointestinal disorder or disease development if none had occurred, or no further gastrointestinal disorder or disease development if there had already been development of the gastrointestinal disorder or disease. Also considered is the ability of one to prevent some or all of the symptoms associated with the gastrointestinal disorder or disease.

A "prodrug" refers to a drug or compound in which the pharmacological action results from conversion by metabolic processes within the body. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs may be designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:G210-218 (1995); McLoed et al., *Gastroenterol,* 106: 405-413 (1994); Hochhaus et al., *Biomed. Chrom.*, 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987.

"Proton pump inhibitor product" refers to a product sold on the market. Proton pump inhibitor products include, for example, Priolosec®, Nexium®, Prevacid®, Protonix®, and Aciphex®.

"Serum concentration" refers to the concentration of a substance such as a therapeutic agent, in blood plasma or blood serum of a subject. It is understood that the serum concentration of a therapeutic agent may vary many-fold between subjects, due to variability with respect to metabolism of therapeutic agents. In accordance with one aspect of the present invention, the serum concentration of a proton pump inhibitors and/or prokinetic agent may vary from subject to subject. Likewise, values such as maximum serum concentration ($C_{max}$) or time to reach maximum serum concentration ($T_{max}$), or total area under the serum concentration time curve (AUC) may vary from subject to subject. Due to this variability, the amount necessary to constitute "a therapeutically effective amount" of proton pump inhibitor, prokinetic agent, or other therapeutic agent, may vary from subject to subject. It is understood that when mean serum concentrations are disclosed for a population of subjects, these mean values may include substantial variation.

"Solubilizers" include compounds such as citric acid, succinic acid, fumaric acid, malic acid, tartaric acid, maleic acid, glutaric acid, sodium bicarbonate, sodium carbonate and the like.

"Stabilizers" include compounds such as any antioxidation agents, buffers, acids, and the like.

"Suspending agents" or "thickening agents" include compounds such as polyvinylpyrrolidone, e.g., polyvinylpyrrolidone K12, polyvinylpyrrolidone K17, polyvinylpyrrolidone K25, or polyvinylpyrrolidone K30; polyethylene glycol, e.g., the polyethylene glycol can have a molecular weight of about 300 to about 6000, or about 3350 to about 4000, or about 7000 to about 5400; sodium carboxymethylcellulose; methylcellulose; hydroxypropylmethylcellulose; polysorbate-80; hydroxyethylcellulose; sodium alginate; gums, such as, e.g., gum tragacanth and gum acacia; guar gum; xanthans, including xanthan gum; sugars; cellulosics, such as, e.g., sodium carboxymethylcellulose, methylcellulose, sodium carboxymethylcellulose, hydroxypropylmethylcellulose, hydroxyethylcellulose; polysorbate-80; sodium alginate; polyethoxylated sorbitan monolaurate; polyethoxylated sorbitan monolaurate; povidone and the like.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

A "therapeutically effective amount" or "effective amount" is that amount of a pharmaceutical agent to achieve a pharmacological effect. The term "therapeutically effective amount" includes, for example, a prophylactically effective amount. An "effective amount" of a proton pump inhibitor is an amount effective to achieve a desired pharmacologic effect or therapeutic improvement without undue adverse side effects. For example, an effective amount of a proton pump inhibitor refers to an amount of proton pump inhibitor that reduces acid secretion, or raises gastrointestinal fluid pH, or reduces gastrointestinal bleeding, or reduces the need for blood transfusion, or improves survival rate, or provides for a more rapid recovery from a gastric acid related disorder. The effective amount of a pharmaceutical agent will be selected by those skilled in the art depending on the particular patient and the disease level. It is understood that "an effect amount" or "a therapeutically effective amount" can vary from subject to subject, due to variation in metabolism of therapeutic agents such as proton pump inhibitors and/or prokinetic agents, age, weight, general condition of the subject, the condition being treated, the severity of the condition being treated, and the judgment of the prescribing physician.

"Total intensity of aroma" is the overall immediate impression of the strength of the aroma and includes both aromatics and nose feel sensations.

"Total intensity of flavor" is the overall immediate impression of the strength of the flavor including aromatics, basic tastes and mouth feel sensations.

"Treat" or "treatment" as used in the context of a gastric acid related disorder refers to any treatment of a disorder or disease associated with a gastrointestinal disorder, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder. Thus, as used herein, the term "treat" is used synonymously with the term "prevent."

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, and the like.

Proton Pump Inhibitors

The terms "proton pump inhibitor," "PPI," and "proton pump inhibiting agent" can be used interchangeably to describe any acid labile pharmaceutical agent possessing pharmacological activity as an inhibitor of H+/K+-ATPase. A proton pump inhibitor may, if desired, be in the form of free base, free acid, salt, ester, hydrate, anhydrate, amide, enantiomer, isomer, tautomer, prodrug, polymorph, derivative, or the like, provided that the free base, salt, ester, hydrate, amide, enantiomer, isomer, tautomer, prodrug, or any other pharmacologically suitable derivative is therapeutically active.

In various embodiments, the proton pump inhibitor can be a substituted bicyclic aryl-imidazole, wherein the aryl group can be, e.g., a pyridine, a phenyl, or a pyrimidine group and is attached to the 4- and 5-positions of the imidazole ring. Proton pump inhibitors comprising a substituted bicyclic aryl-imidazoles include, but are not limited to, omeprazole, hydroxyomeprazole, esomeprazole, lansoprazole, pantoprazole, rabeprazole, dontoprazole, habeprazole, perprazole, tenatoprazole, ransoprazole, pariprazole, leminoprazole, or a free base, free acid, salt, hydrate, ester, amide, enantiomer, isomer, tautomer, polymorph, prodrug, or derivative thereof. See, e.g., *The Merck Index*, Merck & Co. Rahway, N.J. (2001).

Other proton pump inhibitors include but are not limited to: soraprazan (Altana); ilaprazole (U.S. Pat. No. 5,703,097) (Il-Yang); AZD-0865 (AstraZeneca); YH-1885 (PCT Publication WO 96/05177) (SB-641257) (2-pyrimidinamine, 4-(3,4-dihydro-1-methyl-2(1H)-isoquinolinyl)-N-(4-fluorophenyl)-5,6-dimethyl-monohydrochloride)(YuHan); BY-112 (Altana); SPI-447 (Imidazo(1,2-a)thieno(3,2-c)pyridin-3-amine,5-methyl-2-(2-methyl-3-thienyl) (Shinnippon); 3-hydroxymethyl-2-methyl-9-phenyl-7H-8,9-dihydro-pyrano(2,3-c)-imidazo(1,2-a)pyridine (PCT Publication WO 95/27714) (AstraZeneca); Pharmaprojects No. 4950 (3-hydroxymethyl-2-methyl-9-phenyl-7H-8,9-dihydro-pyrano(2,3-c)-imidazo(1,2-a)pyridine) (AstraZeneca, ceased) WO 95/27714; Pharmaprojects No. 4891 (EP 700899) (Aventis); Pharmaprojects No. 4697 (PCT Publication WO 95/32959) (AstraZeneca); H-335/25 (AstraZeneca); T-330 (Saitama 335) (Pharmacological Research Lab); Pharmaprojects No. 3177 (Roche); BY-574 (Altana); Pharmaprojects No. 2870 (Pfizer); AU-1421 (EP 264883) (Merck); AU-2064 (Merck); AY-28200 (Wyeth); Pharmaprojects No. 2126 (Aventis); WY-26769 (Wyeth); pumaprazole (PCT Publication WO 96/05199) (Altana); YH-1238 (YuHan); Pharmaprojects No. 5648 (PCT Publication WO 97/32854) (Dainippon); BY-686 (Altana); YM-020 (Yamanouchi); GYKI-34655 (Ivax); FPL-65372 (Aventis); Pharmaprojects No. 3264 (EP 509974) (AstraZeneca); nepaprazole (To a Eiyo); HN-11203 (Nycomed Pharma); OPC-22575; pumilacidin A (BMS); saviprazole (EP 234485) (Aventis); SKand F-95601 (GSK, discontinued); Pharmaprojects No. 2522 (EP 204215) (Pfizer); S-3337 (Aventis); RS-13232A (Roche); AU-1363 (Merck); SKand F-96067 (EP 259174) (Altana); SUN 8176 (Daiichi Phama); Ro-18-5362 (Roche); ufiprazole (EP 74341) (AstraZeneca); and Bay-p-1455 (Bayer); or a free base, free acid, salt, hydrate, ester, amide, enantiomer, isomer, tautomer, polymorph, prodrug, or derivative of these compounds.

Still other proton pump inhibitors contemplated by the present invention include those described in the following U.S. Pat. Nos. 4,628,098; 4,689,333; 4,786,505; 4,853,230; 4,965,269; 5,021,433; 5,026,560; 5,045,321; 5,093,132; 5,430,042; 5,433,959; 5,576,025; 5,639,478; 5,703,110; 5,705,517; 5,708,017; 5,731,006; 5,824,339; 5,855,914; 5,879,708; 5,948,773; 6,017,560; 6,123,962; 6,187,340; 6,296,875; 6,319,904; 6,328,994; 4,255,431; 4,508,905; 4,636,499; 4,738,974; 5,690,960; 5,714,504; 5,753,265; 5,817,338; 6,093,734; 6,013,281; 6,136,344; 6,183,776; 6,328,994; 6,479,075; 6,559,167.

Other substituted bicyclic aryl-imidazole compounds as well as their salts, hydrates, esters, amides, enantiomers, isomers, tautomers, polymorphs, prodrugs, and derivatives may be prepared using standard procedures known to those skilled in the art of synthetic organic chemistry. See, e.g., March, *Advanced Organic Chemistry: Reactions, Mechanisms and Structure*, 4th Ed. (New York: Wiley-Interscience, 1992); Leonard et al., *Advanced Practical Organic Chemistry* (1992); Howarth et al., *Core Organic Chemistry* (1998); and Weisermel et al., *Industrial Organic Chemistry* (2002).

"Pharmaceutically acceptable salts," or "salts," include, e.g., the salt of a proton pump inhibitor prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, β-hydroxybutyric, galactaric and galacturonic acids.

In one embodiment, acid addition salts are prepared from the free base using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

In other embodiments, an acid addition salt is reconverted to the free base by treatment with a suitable base. In a further embodiment, the acid addition salts of the proton pump inhibitors are halide salts, which are prepared using hydrochloric or hydrobromic acids. In still other embodiments, the basic salts are alkali metal salts, e.g., sodium salt.

Salt forms of proton pump inhibiting agents include, but are not limited to: a sodium salt form such as esomeprazole sodium, omeprazole sodium, rabeprazole sodium, pantoprazole sodium; or a magnesium salt form such as esomeprazole magnesium or omeprazole magnesium, described in U.S. Pat. No. 5,900,424; a calcium salt form; or a potassium salt form such as the potassium salt of esomeprazole, described in U.S. patent application No. 02/0198239 and U.S. Pat. No. 6,511, 996. Other salts of esomeprazole are described in U.S. Pat. No. 4,738,974 and U.S. Pat. No. 6,369,085. Salt forms of pantoprazole and lansoprazole are discussed in U.S. Pat. Nos. 4,758,579 and 4,628,098, respectively.

In one embodiment, preparation of esters involves functionalizing hydroxyl and/or carboxyl groups that may be present within the molecular structure of the drug. In one embodiment, the esters are acyl-substituted derivatives of free alcohol groups, e.g., moieties derived from carboxylic acids of the formula $RCOOR_1$ where $R_1$ is a lower alkyl group. Esters can be reconverted to the free acids, if desired, by using conventional procedures such as hydrogenolysis or hydrolysis.

"Amides" may be prepared using techniques known to those skilled in the art or described in the pertinent literature. For example, amides may be prepared from esters, using suitable amine reactants, or they may be prepared from an anhydride or an acid chloride by reaction with an amine group such as ammonia or a lower alkyl amine.

"Tautomers" of substituted bicyclic aryl-imidazoles include, e.g., tautomers of omeprazole such as those described in U.S. Pat. Nos. 6,262,085; 6,262,086; 6,268,385; 6,312,723; 6,316,020; 6,326,384; 6,369,087; and 6,444,689; and U.S. Patent Publication No. 02/0156103.

An exemplary "isomer" of a substituted bicyclic aryl-imidazole is the isomer of omeprazole including but not limited to isomers described in: Oishi et al., Acta Cryst. (1989), C45, 1921-1923; U.S. Pat. No. 6,150,380; U.S. patent Publication No. 02/0156284; and PCT Publication No. WO 02/085889.

Exemplary "polymorphs" include, but are not limited to, those described in PCT Publication No. WO 92/08716, and U.S. Pat. Nos. 4,045,563; 4,182,766; 4,508,905; 4,628,098; 4,636,499; 4,689,333; 4,758,579; 4,783,974; 4,786,505; 4,808,596; 4,853,230; 5,026,560; 5,013,743; 5,035,899; 5,045,321; 5,045,552; 5,093,132; 5,093,342; 5,433,959; 5,464,632; 5,536,735; 5,576,025; 5,599,794; 5,629,305; 5,639,478; 5,690,960; 5,703,110; 5,705,517; 5,714,504; 5,731,006; 5,879,708; 5,900,424; 5,948,773; 5,997,903; 6,017,560; 6,123,962; 6,147,103; 6,150,380; 6,166,213; 6,191,148; 5,187,340; 6,268,385; 6,262,086; 6,262,085; 6,296,875; 6,316,020; 6,328,994; 6,326,384; 6,369,085; 6,369,087; 6,380,234; 6,428,810; 6,444,689; and 6,462,0577.

Micronized Proton Pump Inhibitor

Particle size of the proton pump inhibitor can affect the solid dosage form in numerous ways. Because decreased particle size increases in surface area (S), the particle size reduction provides an increase in the rate of dissolution (dM/dt) as expressed in the Noyes-Whitney equation below:

$$dM/dt = DS/H(Cs-C)$$

M=mass of drug dissolved; t=time; D=diffusion coefficient of drug; S=effective surface area of drug particles; H=stationary layer thickness; Cs=concentration of solution at saturation; and C=concentration of solution at time t.

Because omeprazole, as well as other proton pump inhibitors, has poor water solubility, to aid the rapid absorption of the drug product, various embodiments of the present invention use micronized proton pump inhibitor in the microencapsulation. In some embodiments, the average particle size of at least about 90% the micronized proton pump inhibitor is less than about 200 µm, 150 µm, 100 µm, 80 µm, 60 µm, 40 µm, or less than about 35 µm, or less than about 30 µm, or less than about 25 µm, or less than about 20 µm, or less than about 15 µm, or less than about 10 µm. In other embodiments, at least 80% of the micronized proton pump inhibitor has an average particle size of less than about 200 µm, 150 µm, 100 µm, 80 µm, 60 µm, 40 µm, or less than about 35 µm, or less than about 30 µm, or less than about 25 µm, or less than about 20 µm, or less than about 15 µm, or less than about 10 µm. In still other embodiments, at least 70% of the micronized proton pump inhibitor has an average particle size of less than about 200 µm, 150 µm, 100 µm, 80 µm, 60 µm, 40 µm, or less than about 35 µm, or less than about 30 µm, or less than about 25 µm, or less than about 20 µm, or less than about 15 µm, or less than about 10 µm.

In other embodiments, the micronized proton pump inhibitor is of a size that allows greater than 50% of the proton pump inhibitor to be released within about 1 hour or 50 minutes, 40 minutes, 30 minutes, 20 minutes or 10 minutes of dissolution testing. In other embodiments, the micronized proton pump inhibitor allows greater than 25% of the proton pump inhibitor to be released within about 45 minutes, 30 minutes, or 15 minutes of dissolution testing.

Compositions are provided wherein the micronized proton pump inhibitor is of a size which allows greater than 75% of the proton pump inhibitor to be released within about 1.5 hours, or within about 1.25 hours, or within about 1 hour, or within about 50 minutes, or within about 40 minutes, or within about 30 minutes, or within about 20 minutes, or within about 10 minutes, or within about 5 minutes of dissolution testing. In another embodiment of the invention, the micronized proton pump inhibitor is of a size which allows greater than 90% of the proton pump inhibitor to be released within about 1.5 hours, or within about 1.25 hours, or within about 1 hour, or within about 50 minutes, or within about 40 minutes, or within about 30 minutes, or within about 20 minutes, or within about 10 minutes, or within about 5 minutes of dissolution testing. See U.S. application Ser. No. 10/893,092, filed Jul. 16, 2004, which claims priority to U.S. Provisional Application No. 60/488,324 filed Jul. 18, 2003, and any subsequent application claiming priority to these applications, all of which are incorporated by reference in their entirety.

Particle Size of Ingredients

The particle size of the proton pump inhibitor, antacid and excipients is an important factor which can effect bioavailability, blend uniformity, segregation, and flow properties. In general, smaller particle sizes of a drug increases the bioabsorption rate of the drug with substantially poor water solubility by increasing the surface area. The particle size of the drug and excipients can also affect the suspension properties of the pharmaceutical formulation. For example, smaller particles are less likely to settle and therefore form better suspensions.

In various embodiments, the average particle size of the dry powder (which can be administered directly, as a powder for suspension, or used in a solid dosage form) is less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In other embodiments, the average particle size of the aggregates is between about 25 microns in diameter to about 300 microns in diameter. In still other embodiments, the average particle size of the aggregates is between about 25 microns in diameter to about 150 microns in diameter. And, in still further embodiments, the average particle size of the aggregates is between about 25 microns in diameter to about 100 microns in diameter. The term "average particle size" is intended to describe the average diameter of the particles and/or agglomerates used in the pharmaceutical formulation.

In another embodiment, the average particle size of the insoluble excipients is between about 5 µm to about 500 µm, or less than about 400 µm, or less than about 300 µm, or less than about 200 µm, or less than about 150 µm, or less than about 100 µm, or less than about 90 µm, or less than about 80 µm, or less than about 70 µm, or less than about 60 µm, or less than about 50 µm, or less than about 40 µm, or less than about 30 µm, or less than about 25 µm, or less than about 20 µm, or less than about 15 µm, or less than about 10 µm, or less than about 5 µm.

In other embodiments of the present invention, at least about 80% of the particles have a particle size of less than about 300 µm, or less than about 250 µm, or less than about 200 µm, or less than about 150 µm, or less than about 100 µm, or less than about 500 µm. In another embodiment, at least about 85% of the dry powder particles have a particle size of less than about 300 µm, or less than about 250 µm, or less than about 200 µm, or less than about 150 µm, or less than about 100 µm, or less than about 50 µm. In still other embodiments of the present invention, at least about 90% of the dry powder particles have a particle size of less than about 300 µm, or less than about 250 µm, or less than about 200 µm, or less than about 150 µm, or less than about 100 µm, or less than about 50 µm. In yet another embodiment, at least about 95% of the dry powder particles have a particle size of less than about 300 µm, or less than about 250 µm, or less than about 200 µm, or less than about 150 µm, or less than about 100 µm, or less than about 50 µm.

In other embodiments, the average particle size of the insoluble material is between about 5 µm to about 250 µm in diameter. In other embodiments, the average particle size of the insoluble excipients is between about 5 µm to about 100 µm, or between about 5 µm to about 80 µm, or between about 5 µm to about 50 µm in diameter.

In another embodiment, the particle size of other excipients is chosen to be about the same as the particle size of the antacid. In yet another embodiment, the particle size of the insoluble excipients is chosen to be about the same as the particle size of the proton pump inhibitor.

Several factors can be considered in choosing both the proper excipient and its quantity. For example, the excipient should be pharmaceutically acceptable. Also, in some examples, rapid dissolution and neutralization of gastric acid to maintain the gastric pH at about 6.5 for at least one hour. The excipients which will be in contact with the proton pump inhibitor, if any, should also be chemically compatible with the proton pump inhibitor. "Chemically compatible" is intended to mean that the material does not lead to more than 10% degradation of the proton pump inhibitor when stored at room temperature for at least about 1 year.

Parietal cell activators are administered in an amount sufficient to produce the desired stimulatory effect without causing untoward side effects to patients. In one embodiment, the parietal cell activator is administered in an amount of about 5 mg to about 2.5 grams per 20 mg dose of the proton pump inhibitor.

Antacids

The pharmaceutical composition of the invention comprises one or more antacids. A class of antacids useful in the present invention include, e.g., antacids possessing pharmacological activity as a weak base or a strong base. In one embodiment, the antacid, when formulated or delivered with an proton pump inhibiting agent, functions to substantially prevent or inhibit the acid degradation of the proton pump inhibitor by gastrointestinal fluid for a period of time, e.g., for a period of time sufficient to preserve the bioavailability of the proton pump inhibitor administered. The antacid can be delivered before, during, and/or after delivery of the Proton Pump Inhibitor. In one aspect of the present invention, the antacid includes a salt of a Group IA metal, including, e.g., a bicarbonate salt of a Group IA metal (alkali metal), a carbonate salt of a Group IA metal, an alkali earth metal antacid (Group IIA metal), an aluminum antacid, a calcium antacid, or a magnesium antacid.

Other antacids suitable for the present invention include, e.g., alkali metal (a Group IA metal including, but not limited to, lithium, sodium, potassium, rubidium, cesium, and francium) or alkaline earth metal (Group IIA metal including, but not limited to, beryllium, magnesium, calcium, strontium, barium, radium) carbonates, phosphates, bicarbonates, citrates, borates, acetates, phthalates, tartrate, succinates and the like, such as sodium or potassium phosphate, citrate, borate, acetate, bicarbonate and carbonate.

In various embodiments, an antacid includes, e.g., an amino acid, an alkali salt of an amino acid, aluminum hydroxide, aluminum hydroxide/magnesium carbonate/calcium carbonate co-precipitate, aluminum magnesium hydroxide, aluminum hydroxide/magnesium hydroxide co-precipitate, aluminum hydroxide/sodium bicarbonate co-precipitate, aluminum glycinate, calcium acetate, calcium bicarbonate, calcium borate, calcium carbonate, calcium citrate, calcium gluconate, calcium glycerophosphate, calcium hydroxide, calcium lactate, calcium phthalate, calcium phosphate, calcium succinate, calcium tartrate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometamol. (Based in part upon the list provided in *The Merck Index*, Merck & Co. Rahway, N.J. (2001)). In addition, due to the ability of proteins or protein hydrolysates to react with stomach acids, they too can serve as antacids in the present invention. Furthermore, combinations of the above mentioned antacids can be used in the pharmaceutical formulations described herein.

The antacids useful in the present invention also include antacids or combinations of antacids that interact with HCl (or other acids in the environment of interest) faster than the proton pump inhibitor interacts with the same acids. When placed in a liquid phase, such as water, these antacids produce and maintain a pH greater than the pKa of the proton pump inhibitor. In various embodiments, the antacid is selected from sodium bicarbonate, sodium carbonate, calcium carbonate, magnesium oxide, magnesium hydroxide, magnesium carbonate, aluminum hydroxide, and mixtures thereof. In other embodiments, the antacid is present in the pharmaceutical formulations of the present invention in an amount greater than about 5 mEq of antacid. In other embodiments, the antacid is present in the pharmaceutical formulations of the present invention in an amount greater than about 7 mEq of antacid. In other embodiments, the antacid is present in the pharmaceutical formulations of the present invention in an amount greater than about 10 mEq of antacid. In other embodiments, the antacid is present in the pharmaceutical formulations of the present invention in an amount greater than about 15 mEq of antacid. In other embodiments, the antacid is present in the pharmaceutical formulations of the present invention in an amount greater than about 20 mEq of antacid.

In another embodiment, the antacid comprises sodium bicarbonate in about 0.1 mEq/mg proton pump inhibitor to about 5 mEq/mg proton pump inhibitor. In yet another embodiment, the antacid comprises a mixture of sodium bicarbonate and magnesium hydroxide, wherein the sodium bicarbonate and magnesium hydroxide are each present in about 0.1 mEq/mg proton pump inhibitor to about 5 mEq/ng proton pump inhibitor. In still another embodiment, the antacid comprises a mixture of sodium bicarbonate, calcium carbonate, and magnesium hydroxide, wherein the sodium bicarbonate, calcium carbonate, and magnesium hydroxide are each present in about 0.1 mEq/mg proton pump inhibitor to about 5 mEq/mg of the proton pump inhibitor. In another embodiment, the antacid comprises a mixture of sodium bicarbonate and magnesium oxide, wherein the sodium bicarbonate and magnesium oxide are each present in about 0.1 mEq/mg proton pump inhibitor to about 5 mEq/mg proton pump inhibitor.

In various other embodiments of the present invention, the antacid is present in an amount of about 0.1 mEq/mg to about 5 mEq/mg of the proton pump inhibitor, or about 0.5 mEq/mg to about 3 mEq/mg of the proton pump inhibitor, or about 0.6 mEq/mg to about 2.5 mEq/mg of the proton pump inhibitor, or about 0.7 mEq/mg to about 2.0 mEq/mg of the proton pump inhibitor, or about 0.8 mEq/mg to about 1.8 mEq/mg of the proton pump inhibitor, or about 1.0 mEq/mg to about 1.5 mEq/mg of the proton pump inhibitor, or at least 0.5 mEq/mg of the proton pump inhibitor.

In other embodiments, the antacid is present in the pharmaceutical formulations of the present invention in an amount from about 5 to about 50 mEq of antacid. In other embodiments, the antacid is present in the pharmaceutical formulations of the present invention in an amount from about 5 to about 40 mEq of antacid. In other embodiments, the antacid is present in the pharmaceutical formulations of the present invention in an amount from about 10 to about 30 mEq of antacid. In other embodiments, the antacid is present in the pharmaceutical formulations of the present invention in an amount from about 10 to about 20 mEq of antacid. In other embodiments, the antacid is present in the pharmaceutical formulations of the present invention in an amount from about 5 to about 15 mEq of antacid.

In another embodiment, the antacid is present in the pharmaceutical formulations of the present invention in an amount of about 0.1 mEq to about 15 mEq/mg of proton pump inhibitor, or about 0.1 mEq/mg of proton pump inhibitor, or about 0.5 mEq/mg of proton pump inhibitor, or about 1 mEq/mg of proton pump inhibitor, or about 2 mEq/mg of proton pump inhibitor, or about 2.5 mEq/mg of proton pump inhibitor, or about 3 mEq/mg of proton pump inhibitor, or about 3.5 mEq/mg of proton pump inhibitor, or about 4 mEq/mg of proton pump inhibitor, or about 4.5 mEq/mg of proton pump inhibitor, or about 5 mEq/mg of proton pump inhibitor, or about 6 mEq/mg of proton pump inhibitor, or about 7 mEq/mg of proton pump inhibitor, or about 8 mEq/mg of proton pump inhibitor, or about 9 mEq/mg of proton pump inhibitor, or about 10 mEq/mg of proton pump inhibitor, or about 11 mEq/mg of proton pump inhibitor, or about 12 mEq/mg of proton pump inhibitor, or about 13 mEq/mg of proton pump inhibitor, or about 14 mEq/mg of proton pump inhibitor, or about 15 mEq/mg of proton pump inhibitor.

In one embodiment, the antacid is present in the pharmaceutical formulations of the present invention in an amount of about 1 mEq to about 160 mEq per dose, or about 1 mEq, or about 5 mEq, or about 10 mEq, or about 15 mEq, or about 20 mEq, or about 25 mEq, or about 30 mEq, or about 35 mEq, or about 40 mEq, or about 45 mEq, or about 50 mEq, or about 60 mEq, or about 70 mEq, or about 80 mEq, or about 90 mEq, or about 100 mEq, or about 110 mEq, or about 120 mEq, or about 130 mEq, or about 140 mEq, or about 150 mEq, or about 160 mEq per dose.

In another embodiment, the antacid is present in an amount of more than about 5 times, or more than about 10 times, or more than about 20 times, or more than about 30 times, or more than about 40 times, or more than about 50 times, or more than about 60 times, or more than about 70 times, or more than about 80 times, or more than about 90 times, or more than about 100 times the amount of the proton pump inhibiting agent on a weight to weight basis in the composition.

In another embodiment, the amount of antacid present in the pharmaceutical formulation is between 200 and 3500 mg. In other embodiments, the amount of antacid present in the pharmaceutical formulation is about 200 mgs, or about 300 mgs, or about 400 mgs, or about 500 mgs, or about 600 mgs, or about 700 mgs, or about 800 mgs, or about 900 mgs, or about 1000 mgs, or about 1100 mgs, or about 1200 mgs, or about 1300 mgs, or about 1400 mgs, or about 1500 mgs, or about 1600 mgs, or about 1700 mgs, or about 1800 mgs, or about 1900 mgs, or about 2000 mgs, or about 2100 mgs, or about 2200 mgs, or about 2300 mgs, or about 2400 mgs, or about 2500 mgs, or about 2600 mgs, or about 2700 mgs, or about 2800 mgs, or about 2900 mgs, or about 3000 mgs, or about 3200 mgs, or about 3500 mgs.

In some embodiments, if the at least one buffering agent is a combination of two or more buffering agents, the combination comprises at least two non-amino acid buffering agents, wherein the combination of at least two non-amino acid buffering agents comprises substantially no aluminum hydroxide-sodium bicarbonate co-precipitate. In other embodiments, if the pharmaceutical composition comprises an amino acid buffering agent, the total amount of buffering agent present in the pharmaceutical composition is less than about 5 mEq, or less than about 4 mEq, or less than about 3 mEq. The phrase "amino acid buffering agent" as used herein includes amino acids, amino acid salts, and amino acid alkali salts. including: glycine, alanine, threonine, isoleucine, valine, phenylalanine, glutamic acid, asparagininic acid, lysine, aluminum glycinate and/or lysine glutamic acid salt, glycine hydrochloride, L-alanine, DL-alanine, L-threonine, DL-threonine, L-isoleucine, L-valine, L-phenylalanine, L-glutamic acid, L-glutamic acid hydrochloride, L-glutamic acid sodium salt, L-asparaginic acid, L-asparaginic acid sodium salt, L-lysine and L-lysine-L-glutamic acid salt. The term "non-amino acid buffering agent" herein includes buffering agents as defined hereinabove but does not include amino acid buffering agents.

In other embodiments, the pharmaceutical composition comprises substantially no or no poly[phosphoryl/sulfon]-ated carbohydrate and is in the form of a solid dosage unit. In still another related embodiment, if such a composition comprises a poly[phosphoryl/sulfon]-ated carbohydrate (e.g. sucralfate or sucrose octasulfate), the weight ratio of poly[phosphoryl/sulfon]-ated carbohydrate to buffering agent is less than 1:5 (0.2), less than 1:10 (0.1) or less than 1:20 (0.05). Alternatively, the poly[phosphoryl/sulfon]-ated carbohydrate is present in the composition, if at all, in an amount less than 50 mg, less than 25 mg, less than 10 mg or less than 5 mg.

Also provided herein are pharmaceutical formulations comprising at least one soluble antacid. For example, in one embodiment, the antacid is sodium bicarbonate and is present in about 0.1 mEq/mg proton pump inhibitor to about 5 mEq/mg proton pump inhibitor. In another embodiment, the antacid is a mixture of sodium bicarbonate and magnesium hydroxide, wherein the sodium bicarbonate and magnesium hydroxide are each present in about 0.1 mEq/mg proton pump inhibitor to about 5 mEq/mg proton pump inhibitor. Yet in another embodiment, the antacid is a mixture of sodium bicarbonate and magnesium oxide, wherein the sodium bicarbonate and magnesium oxide are each present in about 0.1 mEq/mg proton pump inhibitor to about 5 mEq/mg proton pump inhibitor. The term "soluble antacid" as used herein refers to an antacid that has a solubility of at least 500 mg/mL, or 300 mg/mL, or 200 mg/mL, or 100 mg/mL, or 50 mg/mL in the gastrointestinal fluid. In some embodiments, the soluble antacid is sodium bicarbonate.

Particle Size of Antacids

Particle size of the buffer, especially that an insoluble buffer can affect the onset of in-vivo neutralization of the stomach acid. Since decreased particle size increases in surface area, the particle size reduction provides an increase in the rate of acid neutralization, leading to superior protection of PPI from gastric acid degradation. On the other hand, extremely fine particle size of buffer will result in the powder mixture that is difficult to manufacture in commercial scale due to their poor flow and difficulties in processing (i.e., compression and encapsulation).

In some embodiments of the present invention, the antacid is a specific particle size. For example, in some embodiments, the average particle size is no greater than 20 μm, or no greater than 30 μm, or no greater than 40 μm, or no greater than 50 μm, or no greater than 60 μm or no greater than 70 μm, or no greater than 80 μm, or no greater than 90 μm or no greater than 100 μm in diameter. In various embodiments, at least about 70% of the antacid is no greater than 20 μm, or no greater than 30 μm, or no greater than 40 μm, or no greater than 50 μm, or no greater than 60 μm, or no greater than 70 μm, or no greater than 80 μm, or no greater than 90 μm, or no greater than 100 μm in diameter. In other embodiments, at least about 85% of the antacid is no greater than 20 μm, or no greater than 30 μm, or no greater than 40 μm, or no greater than 50 μm, or no greater than 60 μm, or no greater than 70 μm, or no greater than 80 μm, or no greater than 90 μm or no greater than 100 μm in diameter.

In various embodiments of the present invention, the antacid is micronized. In some embodiments, particle size of at least 90% of antacid ($D_{90}$) is lees than about 300 μm, or less than about 250 μm, or less than about 200 μm, or less than about 150 μm, or less than about 100 μm. In other embodiments, at least 75% of the antacid ($D_{75}$) has particle size of less than about 300 μm, or less than about 250 μm, or less than about 200 μm, or less than about 150 μm, or less than about 100 μm. In still other embodiments, at least 50% of the antacid ($D_{50}$) has particle size of less than about 300 μm, or less than about 250 μm, or less than about 200 μm, or less than about 150 μm, or less than about 100 μm.

Spray dried antacid can also facilitate the speed of neutralization by fast reacting with acid upon contact. Sprayed dried antacid typically has spherical particle shape which aids with achieving homogeneous blend during manufacturing process. In one embodiment the antacid is spray dried with at least 15% of coating material such as maltodextrin or starch. In still other embodiment the antacid is spray dried with at least 10% of coating material such as maltodextrin or starch. Yet another embodiment the antacid is spray dried with at least 5% of coating material such as maltodextrin or starch. In still other embodiments, the antacid is spray dried with between about 1% to about 10% of a coating material. In yet other embodiments, the antacid is spray dried with about 5% of a coating material such as maltodextrin or starch.

Shelf Life Enhancing Materials

Materials useful for enhancing the shelf-life of the pharmaceutical formulations of the present invention include materials compatible with the proton pump inhibitor of the pharmaceutical formulations which sufficiently isolate the proton pump inhibitor from other non-compatible excipients. Materials compatible with the proton pump inhibitors of the present invention are those that enhance the shelf-life of the proton pump inhibitor, i.e., by slowing or stopping degradation of the proton pump inhibitor.

A pharmaceutical formulation of the present invention may have an enhanced shelf-life stability if, e.g., the microencapsulated proton pump inhibitor has less than about 0.5% degradation after one month of storage at room temperature, or less than about 1% degradation after one month at room temperature, or less than about 1.5% degradation after one month of storage at room temperature, or less than about 2% degradation after one month storage at room temperature, or less than about 2.5% degradation after one month of storage at room temperature, or less than about 3% degradation after one month of storage at room temperature.

In other embodiments, a pharmaceutical formulation of the present invention may have an enhanced shelf-life stability if the pharmaceutical formulation contains less than about 5% total impurities after about 3 years of storage, or after about 2.5 years of storage, or about 2 years of storage, or about 1.5 years of storage, or about 1 year of storage, or after 11 months of storage, or after 10 months of storage, or after 9 months of storage, or after 8 months of storage, or after 7 months of storage, or after 6 months of storage, or after 5 months of storage, or after 4 months of storage, or after 3 months of storage, or after 2 months of storage, or after 1 month of storage.

In further embodiments, pharmaceutical formulations of the present invention may have enhanced shelf-life stability if the pharmaceutical formulation contains less degradation of the proton pump inhibitor than proton pump inhibitor in the same formulation which is not microencapsulated or dry coated, or "bare". For example, if bare proton pump inhibitor in the pharmaceutical formulation degrades at room temperature by more than about 2% after one month of storage and the microencapsulated or dry coated material degrades at room temperature by less than about 2% after one month of storage, then the proton pump inhibitor has been microencapsulated or dry coated with a compatible material that enhances the shelf-life of the pharmaceutical formulation.

In some embodiments, the material useful for enhancing the shelf-life of the pharmaceutical formulations increases the shelf-life stability of the pharmaceutical formulation for at least about 5 days at room temperature, or at least about 10 days at room temperature, or at least about 15 days at room temperature, or at least about 20 days at room temperature, or at least about 25 days at room temperature, or at least about 30 days at room temperature or at least about 2 months at room temperature, or at least about 3 months at room temperature, or at least about 4 months at room temperature, or at least about 5 months at room temperature, or at least about 6 months at room temperature, or at least about 7 months at room temperature, or at least about 8 months at room temperature, or at least about 9 months at room temperature, or at least about 10 months at room temperature, or at least about 11 months at room temperature, or at least about one year at room temperature, or at least about 1.5 years at room temperature, or at least about 2 years at room temperature, or at least about 2.5 years at room temperature, or about 3 years at room temperature.

Microencapsulating Materials

Exemplary microencapsulation materials useful for enhancing the shelf-life of pharmaceutical formulations comprising a proton pump inhibitor include, e.g., cellulose hydroxypropyl ethers (HPC) such as EF Klucel®, Nisso HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aqualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD 100, and Eudragit® E100; cellulose acetate phthalate; sepifilms such as mixtures of HPMC and stearic acid, cyclodextrins, and mixtures of these materials. In other embodiments, the microencapsulation material is selected from hydroxypropylcellulose and cellulose ethers. In still other embodiments, the microencapsulation material is selected from Klucel EF, Klucel EXF, Methocel E5, Methocel E15, and Methocel A15. In other embodiments, the material that enhances the shelf-life has a viscosity of 100-800 cps at 10% solution; or a viscosity of 200-600 cps at 10% solution; or a viscosity of 300-400 cps at 10% solution.

In various embodiments, a buffering agent such as sodium bicarbonate is incorporated into the microencapsulation material. In other embodiments, an antioxidant such as BHT or BHA is incorporated into the microencapsulation material. In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for enhancing the shelf-life of the pharmaceutical formulations is from the USP or the National Formulary (NF).

In further embodiments, one or more other compatible materials are present in the microencapsulation material. Exemplary materials include, e.g., parietal cell activators, organic solvents, erosion facilitators, diffusion facilitators, anti-adherents, anti-foaming agents, antioxidants, sweetening agents, flavoring agents, and carrier materials such as binders, suspending agents, disintegration agents, filing agents, surfactants, solubilizers, stabilizers, lubricants, wetting agents, and diluents.

In some embodiments of the present invention, the final formulation of the pharmaceutical formulation will be in the form of a tablet and at least about 50%, or at least about 55%, or at least about 60%, or at least about 65%, or at least about 70%, or at least about 75%, or at least about 80%, or at least about 85% or at least about 90%, or at least about 92%, or at least about 95%, or at least about 98%, or at least about 99% of the microspheres survive the tableting process, wherein microspheres that have survived the tableting process are those which provide the desired properties described herein.

In other embodiments, the final formulation of the pharmaceutical formulation is in the form of a powder for oral suspension and the microencapsulation material surrounding the proton pump inhibitor will sufficiently dissolve in water, with or without stirring, in less than 1 hour, or less than 50 minutes, or less than 40 minutes, or less than 30 minutes, or less than 25 minutes, or less than 20 minutes, or less than 15 minutes, or less than 10 minutes or less than 5 minutes, or less than 1 minute. Sufficiently dissolves means that at least about 50% of the encapsulation material has dissolved.

In various embodiments the microencapsulating material useful for enhancing the shelf-life of the pharmaceutical formulation sufficiently disintegrates to release the proton pump inhibitor into the gastrointestinal fluid of the stomach within less than about 1.5 hours, or within about 10 minutes, or within about 20 minutes, or within about 30 minutes, or within about or within about 40 minutes, or within about 50 minutes, or within about 1 hour, or within about 1.25 hours, or within about 1.5 hours after exposure to the gastrointestinal fluid. Sufficiently disintegrates means that at least about 50% of the microencapsulation material has dissolved.

In various embodiments, the average particle sizes of the microencapsulated drugs range from submicron to less than about 1,000 microns in diameter, or less than about 900 microns in diameter, or less than about 800 microns in diameter, or less than about 700 microns in diameter, or less than about 600 microns in diameter, or less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In other embodiments, the average particle size of the aggregates is between about 25 microns in diameter to about 300 microns in diameter. In still other embodiments, the average particle size of the aggregates is between about 100 microns in diameter to about 200 microns in diameter. And in still further embodiments, the average particle size of the aggregates is between about 25 microns in diameter to about 100 microns in diameter. The term "average particle size" is intended to describe the average diameter of the particles and/or agglomerates used in the pharmaceutical formulation.

Taste-Masking Materials

Proton pump inhibitors are inherently bitter tasting and in one embodiment of the present invention, these bitter proton pump inhibitors are microencapsulated with a taste-masking material. Materials useful for masking the taste of pharmaceutical formulations include those materials capable of microencapsulating the proton pump inhibitor, thereby protecting the senses from its bitter taste. Taste-masking materials of the present invention provide superior pharmaceutical formulations by e.g., creating a more palatable pharmaceutical formulation as compared to pharmaceutical formulations and/or by creating a dosage form requiring less of the traditional flavoring or tastemasking agents.

The "flavor leadership" criteria used to develop a palatable product include (1) immediate impact of identifying flavor, (2) rapid development of balanced, full flavor, (3) compatible mouth feel factors, (4) no "off" flavors, and (5) short aftertaste. See, e.g., Worthington, *A Matter of Taste, Pharmaceutical Executive* (April 2001). The pharmaceutical formulations of the present invention improve upon one or more of these criteria.

There are a number of known methods to determine the effect of a taste-masking material such as discrimination tests for testing differences between samples and for ranking a series of samples in order of a specific characteristic; scaling tests used for scoring the specific product attributes such as flavor and appearance; expert tasters used to both quantitatively and qualitatively evaluate a specific sample; affective tests for either measuring the response between two products, measuring the degree of like or dislike of a product or specific attribute, or determine the appropriateness of a specific attribute; and descriptive methods used in flavor profiling to provide objective description of a product are all methods used in the field.

Different sensory qualities of a pharmaceutical formulation such as aroma, flavor, character notes, and aftertaste can be measured using tests know in the art. See, e.g., Roy et al., *Modifying Bitterness: Mechanism, Ingredients, and Applications* (1997). For example, aftertaste of a product can be measured by using a time vs. intensity sensory measurement. And recently, modern assays have been developed to alert a processor of formulations to the bitter taste of certain substances. Using information known to one of ordinary skill in the art, one would readily be able to determine whether one or more sensory qualities of a pharmaceutical formulation of the present invention have been improved by the use of the taste-masking material.

Taste of a pharmaceutical formulation is important for both increasing patient compliance as well as for competing with other marketed products used for similar diseases, conditions and disorders. Taste, especially bitterness, is particularly important in pharmaceutical formulations for children since, because they cannot weigh the positive benefit of getting better against the immediate negative impact of the bitter taste in their mouth, they are more likely to refuse a drug that tastes bad. Thus, for pharmaceutical formulations for children, it becomes even more important to mask the bitter taste.

Microencapsulation of the proton pump inhibitor can (1) lower the amount of flavoring agents necessary to create a palatable product and/or (2) mask the bitter taste of the proton pump inhibitor by separating the drug from the taste receptors.

Taste-masking materials include, e.g., cellulose hydroxypropyl ethers (HPC) such as Klucel®, Nisswo HPC and PrimaFlo HP22; low-substituted hydroxypropyl ethers (L-HPC); cellulose hydroxypropyl methyl ethers (HPMC) such as Seppifilm-LC, Pharmacoat®, Metolose SR, Opadry YS, PrimaFlo, MP3295A, Benecel MP824, and Benecel MP843; methylcellulose polymers such as Methocel® and Metolose®; Ethylcelluloses (EC) and mixtures thereof such as E461, Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials.

In other embodiments of the present invention, additional taste-masking materials contemplated are those described in U.S. Pat. Nos. 4,851,226, 5,075,114, and 5,876,759. For further examples of taste-masking materials, see, e.g., *Remington: The Science and Practice of Pharmacy*, Nineteenth Ed. (Easton, Pa.: Mack Publishing Company, 1995); Hoover, John E., *Remington's Pharmaceutical Sciences* (Mack Publishing Co., Easton, Pa. 1975); Liberman, H. A. and Lachman, L., Eds., *Pharmaceutical Dosage Forms* (Marcel Decker, New York, N.Y., 1980); and *Pharmaceutical Dosage Forms and Drug Delivery Systems*, Seventh Ed. (Lippincott Williams & Wilkins 1999).

In various embodiments, a pH modifier such as sodium carbonate or sodium bicarbonate is incorporated into the microencapsulation material. In other embodiments, an anti-oxidant such as BHT or BHA is incorporated into the microencapsulation material. In yet another embodiment, sucrose or sucralose is incorporated into the taste masking material. In still other embodiments, plasticizers such as polyethylene glycol and/or stearic acid are incorporated into the microencapsulation material.

In further embodiments, one or more other compatible materials are present in the microencapsulation material. Exemplary materials include, e.g., parietal cell activators, organic solvents, erosion facilitators, diffusion facilitators, anti-adherents, anti-foaming agents, antioxidants, flavoring agents, and carrier materials such as binders, suspending agents, disintegration agents, filing agents, surfactants, solubilizers, stabilizers, lubricants, wetting agents, diluents.

In addition to microencapsulating the proton pump inhibitors with a taste-masking material or a material that enhances the shelf-life of the formulation as described herein, the pharmaceutical formulations of the present invention may also comprise one or more flavoring agents.

"Flavoring agents" or "sweeteners" useful in the pharmaceutical formulations of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In other embodiments, sodium chloride is incorporated into the pharmaceutical formulation.

Based on the proton pump inhibitor, antacid, and excipients, as well as the amounts of each one, one of skilled in the art would be able to determine the best combination of flavors to provide the optimally flavored product for consumer demand and compliance. See, e.g., Roy et al., Modifying Bitterness: Mechanism, Ingredients, and Applications (1997).

In one embodiment, one or more flavoring agents are mixed with the taste-masking material prior to microencapsulating the proton pump inhibitor and, as such, are part of the taste-masking material. In other embodiments, the flavoring agent is mixed with the non-compatible excipients during the formulation process and is therefore not in contact with the proton pump inhibitor, and not part of the microencapsulation material.

In another embodiment, an antacid, such as sodium bicarbonate, is also microencapsulated with one or more taste-masking materials.

In another embodiment, the weight fraction of the taste masking material is, e.g., about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

In other embodiments of the present invention, the amount of flavoring agent necessary to create a palatable product, as compared to a pharmaceutical formulation comprising non-microencapsulated proton pump inhibitor, is decreased by 5% or less, or by 5% to 10%, or by 10% to 20%, or by 20% to 30%, or by 30% to 40%, or by 40% to 50%, or by 50% to 60%, or by 60% to 70%, or by 70% to 80%, or by 80% to 90%, or by 90% to 95%, or by greater than 95%. In still other embodiments, no flavoring agent is necessary to create a more palatable pharmaceutical formulation as compared to a similar pharmaceutical formulation comprising non-microencapsulated proton pump inhibitor.

In various embodiments of the invention, the total amount of flavoring agent present in the pharmaceutical formulation is less than 20 grams, or less than 15 grams, or less than 10 grams, or less than 8 grams, or less than 5 grams, or less than 4 grams, or less than 3.5 grams, or less than 3 grams, or less than 2.5 grams or less than 2 grams, or less than 1.5 grams, or less than 1 gram, or less than 500 mg, or less than 250 mg, or less than 150 mg, or less than 100 mg, or less than 50 mg.

In particular embodiments, the formulation comprises a microencapsulated omeprazole having approximately 37% omeprazole, the remainder being the immediate release coating designed to protect the micronized omeprazole from degradation by flavor components and other excipients. The shelf life of a chewable product is thus improved. Additionally the flavor of the product can be enhanced, as the immediate release coating provides protection against a wide variety of acidic excipients.

Methods of Microencapsulation

The proton pump inhibitor may be microencapsulated by methods known by one of ordinary skill in the art. Such known methods include, e.g., spray drying processes, spinning disk processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as dry granulation (i.e., roller compaction and slugging), extrusion/spheronization, or nano particle coating may also be used.

The spinning disk method allows for: 1) an increased production rate due to higher feed rates and use of higher solids loading in feed solution, 2) the production of more spherical particles, 3) the production of a more even coating, and 4) limited clogging of the spray nozzle during the process.

Spray drying is often more readily available for scale-up to a commercial scale. In various embodiments, the material used in the spray-dry encapsulation process is emulsified or dispersed into the core material in a concentrated form, e.g., 10-60% solids. In some embodiments of the present invention, the solid loading is between about 10-20%, or between about 10-40%, or between about 40-60%. The microencapsulation material is, in one embodiment, is emulsified until about 1 to 3 μm droplets are obtained. In other embodiments, the microencapsulation material is emulsified until about 1 to 200 μm droplets are obtained, or until about 1 to 100 μm droplets are obtained. In still other embodiments, the median droplet size of the microencapsulation material is between about 1 to about 300 μm, or between about 1 to about 200 μm, or between about 50 to about 150 μm. Once a dispersion of proton pump inhibitor and encapsulation material are obtained, the emulsion is fed as droplets into the heated chamber of the pray drier. In some embodiments, the droplets are sprayed into the chamber or spun off a rotating disk. The microspheres are then dried in the heated chamber and fall to the bottom of the spray drying chamber where they are harvested.

Coacervation involves microencapsulation of materials such as active pharmaceutical ingredients and involves a three part process of particle or droplet formation, coacerate wall formation, and capsule isolation. This method can produce very small particle size microcapsules (10-70 microns).

Extrusion/spheronization is another method that involves wet massing of active pharmaceutical ingredients, followed by the extrusion of the wet mass through a perforated plate to produce short cylindrical rods. These rods are subsequently placed into a rapidly rotating spheronizer to shape the cylindrical rods into uniform spheres. The spheres are subsequently dried using a fluid bed drier and then coated with a functional coating using a fluid bed equipped with a Wurster insert and spray nozzle. This method produces smooth, uniform spheres that are ideal for receiving a functional coating. Drug loadings as high as 80% are possible (depending on drug characteristics).

In some embodiments of the present invention, the microspheres have irregular geometries. In other embodiments, the microspheres are aggregates of smaller particles. In various embodiments, the drug loading of the proton pump inhibitor in the microspheres is greater than 1%, greater than 2.5%, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80% weight percent of the proton pump inhibitor to the microencapsulated drug. In other embodiments, the drug loading of the proton pump inhibitor in the microspheres is between about 5-60 wt %, or about 5-50 wt-%, or about 10-40 wt-%.

Methods of Dry Coating

In addition to microencapsulation, the stability of the proton pump inhibitors used in the present invention may be increased by alternative methods such as dry coating and nano-particle coating. Dry coating involves the formation of granules of coated proton pump inhibitor which are then mixed with other components. Dry granulation is achieved by forming dense compacts which are subsequently milled to a desired particle size and then blended with other components of the pharmaceutical composition. Dry granulation and nano-particle coating can provide enhanced stability and tastemasking characteristics to active pharmaceutical by diluting and isolating such components in a granulated matrix of compatible ingredients that can enhance the shelf life of proton pump inhibitor products as well as tastemask the bitterness if sweetener or flavors are used in coating material.

Typical technique for dry granulation is to use slugging or roller compaction. During slugging process, the dry powders are compressed using a conventional tablet machine, or more usually, a large heavy duty rotary press. The resulting compacts or "slug" are then milled to a desired particle size. Roller compaction is an alternative gentler method, the powder mix being squeezed between two rollers to form a compressed sheet. The sheet normally is weak and brittle and breaks immediately into flakes. These flakes need gentler treatment to break them into granules, and this can be usually be achieved by screening alone. Parikh, D. M., *Handbook of Pharmaceutical Granulation Technology*, (Marcel Dekker ed. 1997).

Nano particle coating is another method that involves a nano particle deposited onto the drug core using Physical Vapour Deposition (PVD) methods. See, e.g., Lu, Y. Chen, S. C., *Advanced Drug Delivery Review: Micro and Nano-Fabrication of Biodegradable Polymers for Drug Delivery* 56, 1621-33 (2004) and Mark W. Horn et al., *Blending of Nanoscale and Microscale in Uniform Large-Area Sculptured Thin-Film Architectures* NANOTECHNOLOGY 15, 303-310 (2004). This method can coat a 10-20 micro drug core with various thickness of metal, or metal salt (e.g., SB, MgO, MgOH, $CaCO_3$, etc.).

In various embodiments, the average particle sizes of the dry coated proton pump inhibitor ranges from submicron to less than about 1,000 microns in diameter, or less than about 900 microns in diameter, or less than about 800 microns in diameter, or less than about 700 microns in diameter, or less than about 600 microns in diameter, or less than about 500 microns in diameter, or less than about 450 microns in diameter, or less than about 400 microns in diameter, or less than about 350 microns in diameter, or less than about 300 microns in diameter, or less than about 250 microns in diameter, or less than about 200 microns in diameter, or less than about 150 microns in diameter, or less than about 100 microns in diameter, or less than about 75 microns in diameter, or less than about 50 microns in diameter, or less than about 25 microns in diameter, or less than about 15 microns in diameter. In other embodiments, the average particle size of the aggregates is between about 25 microns in diameter to about 300 microns in diameter. In still other embodiments, the average particle size of the aggregates is between about 100 microns in diameter to about 200 microns in diameter. And in still further embodiments, the average particle size of the aggregates is between about 25 microns in diameter to about 100 microns in diameter. The term "average particle size" is intended to describe the average diameter of the particles and/or agglomerates used in the pharmaceutical formulation.

In some embodiments, the dry coated proton pump inhibitor granules are less than about 2000 microns, or less than about 1500 microns, or less than about 1000 microns. In some embodiments, the average particle size of the dry coated proton pump inhibitor granules is between about 100 to about 2000 microns, or between about 100 to about 1000 microns, or between about 200 to about 800 microns, or between about 300 to about 600 microns.

In other embodiments, the dry coated proton pump inhibitor granules comprise antacid, binder, lubricant and/or sweeteners. In some embodiments, the antacid is sodium bicarbonate. In other embodiments, the binder is hydroxypropyl cellulose. In still other embodiments, the sweetener is sucralose and/or xylitab. In yet other embodiments, the lubricant is magnesium stearate.

In various embodiments, the dry coated proton pump inhibitor is combined with additional antacid. In some embodiments, the additional antacid is the same antacid as used in the material used to dry coat the proton pump inhibitor. In other embodiments, the antacid is a different antacid. In still other embodiments, the antacid is a combination of two or more antacids.

In yet other embodiments, one or more pharmaceutically acceptable excipients are mixed with the dry coated proton pump inhibitor to form the pharmaceutical composition. In some embodiments the additional pharmaceutical excipients include one or more flavors.

In further embodiments, one or more other compatible materials are present in the dry coating material. Exemplary materials include, e.g., parietal cell activators, organic solvents, erosion facilitators, diffusion facilitators, anti-adherents, anti-foaming agents, antioxidants, flavoring agents, and carrier materials such as binders, suspending agents, disintegration agents, filing agents, surfactants, solubilizers, stabilizers, lubricants, wetting agents, diluents. In some embodiments, the additional compatible materials are binders, lubricants and sweeteners.

In some embodiments, one or more sweeteners are incorporated into the material used to dry coat the proton pump inhibitor. In other embodiments, one or more flavoring agents are incorporated into the material used to dry coat the proton pump inhibitor. In still other embodiments, the material used to dry coat the proton pump inhibitor comprises a sweetener and/or a flavoring agent. In some embodiments, this dry coated proton pump inhibitor is then mixed with additional sweeteners and/or flavoring agents. "Flavoring agents" or "sweeteners" useful in the pharmaceutical formulations of the present invention include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, neotame, acesulfame potassium, mannitol, talin, xylitol, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In other embodiments, sodium chloride is incorporated into the pharmaceutical formulation.

In some embodiments, the weight percent of the proton pump inhibitor in the dry coated granules is about 2-70%. In some embodiments, the weight percent of the proton pump inhibitor in the dry coated granules is about 5-50%, or about 5-30%. In yet other embodiments, the weight percent of the proton pump inhibitor in the granules is about 5%, or about 7%, or about 10%, or about 15%, or about 20%, or about 25%, or about 30%, or about 35%, or about 40%.

It should be noted that the compositions and methods described herein as containing microencapsulated proton pump inhibitors can, in addition to or in the alternative, contain dry coated proton pump inhibitors.

Kinetic Stomach Model

The acid neutralizing capacity and pH profile of various antacid combinations can be evaluated by using an in-vitro stomach model. Several of these simulated dynamic models are known in the art. See, e.g., Smyth et al., Correlation of In-Vivo Methodology for Evaluation of Antacids, J. Pharm. Sci. Vol. 65, 1045 (1976); Hobert, Fordham et al., In-Vivo Evaluation of Liquid Antacids, New England Journal of Med. 288, 923 (1973); Johnson et al., The Chemical Testing of Antacids, Gut 5, 585 (1964); Clain et al., In-Vitro Neutralizing Capacity of Commercially Available Antacid Mixtures and Their Role in the Treatment of Peptic Ulcer, S. Afr. Med. J., 57, 158 (1980); Rossett et al., In-Vitro Evaluation of Efficacy of More Frequently Used Antacids with Particular Attention to Tablets, Gastroentrology, 26, 490; Decktor et al., Comparative Effects of Liquid Antacids on Esophageal and Gastric pH in Patients with Heartburn, Am. J. of Therapeutics, 2, 481 (1995); Charles Fuchs, Antacids: Their Function, Formulation and Evaluation, Drug and Cosmetic Industry, 49, 692; Stewart M. Beekman, Preparation and Properties of New Gastric Antacids I, Aluminum Hydroxide-Magnesium Carbonate Dried Gels, J. Am Pharm. Assoc., 49, 191 (1960). For example, a modified Fuch's model where the continuous influx of 0.5 mEq of acid is added to initial 5.0 mEq of acid to simulate a fasting state of stomach can be used with the present invention.

In various embodiments of the present invention, the antacid increases the gastric pH to at least about 3.5 for no more than about 90 minutes as measured by a simulated stomach model such as Fuch's kinetic in-vitro pH model. In other embodiments, the antacid increases the pH to at least about 3.5 for no more than about 60 minutes. In still other embodiments, the antacid increases the pH to at least about 3.5 for no more than 45 minutes. Depending on the buffer system used (i.e., type of antacid and amount) some embodiments of the present invention, the antacid increases the gastric pH to at least about 3.5 for no more than about 30 minutes as measured by a simulated stomach model such as Fuchs' kinetic in-vitro pH model. In other embodiments, the antacid increases the gastric pH to at least about 3.5 for less than about 25 minutes as measured by a simulated stomach model such as Fuch's kinetic in-vitro pH model. In yet other embodiments, the antacid increases the gastric pH to at least about 3.5 for less than about 20 minutes, or less than about 15 minutes, or less than about 10 minutes as measured by a stimulated stomach model such as Fuch's kinetic in-vitro pH model.

In each of these embodiments, the antacid protects at least some of the proton pump inhibitor and a therapeutically effective amount of the proton pump inhibitor is delivered to the subject.

Dosage

The proton pump inhibiting agent is administered and dosed in accordance with good medical practice, taking into account the clinical condition of the individual patient, the site and method of administration, scheduling of administration, and other factors known to medical practitioners. In human therapy, it is important to provide a dosage form that delivers the required therapeutic amount of the drug in vivo, and renders the drug bioavailable in a rapid manner. In addition to the dosage forms described herein, the dosage forms described by Phillips et al. in U.S. Pat. Nos. 5,840,737, 6,489,346, 6,699,885, and 6,645,988 are incorporated herein by reference.

The percent of intact drug that is absorbed into the bloodstream is not narrowly critical, as long as a therapeutic-disorder-effective amount, e.g., a gastrointestinal-disorder-effective amount of a proton pump inhibiting agent, is absorbed following administration of the pharmaceutical composition to a subject. It is understood that the amount of proton pump inhibiting agent and/or antacid that is administered to a subject is dependent on, e.g., the sex, general health, diet, and/or body weight of the subject.

Illustratively, administration of a substituted bicyclic aryl-imidazole to a young child or a small animal, such as a dog, a relatively low amount of the proton pump inhibitor, e.g., about 1 mg to about 30 mg, will often provide blood serum concentrations consistent with therapeutic effectiveness. Where the subject is an adult human or a large animal, such as a horse, achievement of a therapeutically effective blood serum concentration will require larger dosage units, e.g., about 10 mg, about 15 mg, about 20 mg, about 30 mg, about 40 mg, about 80 mg, or about 120 mg dose for an adult human, or about 150 mg, or about 200 mg, or about 400 mg, or about 800 mg, or about 1000 mg dose, or about 1500 mg dose, or about 2000 mg dose, or about 2500 mg dose, or about 3000 mg dose, or about 3200 mg dose, or about 3500 mg dose for an adult horse.

In various other embodiments of the present invention, the amount of proton pump inhibitor administered to a subject is, e.g., about 1-2 mg/Kg of body weight, or about 0.5 mg/Kg of body weight, or about 1 mg/Kg of body weight, or about 1.5 mg/Kg of body weight, or about 2 mg/Kg of body weight.

Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of gastrointestinal disorders or diseases in accordance with the present invention. In terms of treatment protocols, it should be appreciated that the dosage to be administered will depend on several factors, including the particular agent that is administered, the route chosen for administration, the condition of the particular subject.

In various embodiments, unit dosage forms for humans contain about 1 mg to about 120 mg, or about 1 mg, or about 5 mg, or about 10 mg, or about 15 mg, or about 20 mg, or about 30 mg, or about 40 mg, or about 50 mg, or about 60 mg, or about 70 mg, or about 80, mg, or about 90 mg, or about 100 mg, or about 110 mg, or about 120 mg of a proton pump inhibitor.

In a further embodiment of the present invention, the pharmaceutical formulation is administered in an amount to achieve a measurable serum concentration of a non-acid degraded proton pump inhibiting agent greater than about 100 ng/ml within about 30 minutes after administration of the pharmaceutical formulation. In another embodiment of the present invention, the pharmaceutical formulation is administered to the subject in an amount to achieve a measurable serum concentration of a non-acid degraded or non-acid reacted proton pump inhibiting agent greater than about 100 ng/ml within about 15 minutes after administration of the pharmaceutical formulation. In yet another embodiment, the pharmaceutical formulation is administered to the subject in an amount to achieve a measurable serum concentration of a non-acid degraded or non-acid reacted proton pump inhibiting agent greater than about 100 ng/ml within about 10 minutes after administration of the pharmaceutical formulation.

In another embodiment of the present invention, the composition is administered to the subject in an amount to achieve a measurable serum concentration of the proton pump inhibiting agent greater than about 150 ng/ml within about 15 minutes and to maintain a serum concentration of the proton pump inhibiting agent of greater than about 150 ng/ml from about 15 minutes to about 1 hour after administration of the composition. In yet another embodiment of the present invention, the composition is administered to the subject in an amount to achieve a measurable serum concentration of the proton pump inhibiting agent greater than about 250 ng/ml within about minutes and to maintain a serum concentration of the proton pump inhibiting agent of greater than about 150 ng/ml from about 15 minutes to about 1 hour after administration of the composition. In another embodiment of the present invention, the composition is administered to the subject in an amount to achieve a measurable serum concentration of the proton pump inhibiting agent greater than about 350 ng/ml within about 15 minutes and to maintain a serum concentration of the proton pump inhibiting agent of greater than about 150 ng/ml from about 15 minutes to about 1 hour after administration of the composition. In another embodiment of the present invention, the composition is administered to the subject in an amount to achieve a measurable serum concentration of the proton pump inhibiting agent greater than about 450 ng/ml within about 15 minutes and to maintain a serum concentration of the proton pump inhibiting agent of greater than about 150 ng/ml from about 15 minutes to about 1 hour after administration of the composition.

In another embodiment of the present invention, the composition is administered to the subject in an amount to achieve a measurable serum concentration of the proton pump inhibiting agent greater than about 150 ng/ml within about 30 minutes and to maintain a serum concentration of the proton pump inhibiting agent of greater than about 150 ng/ml from about 30 minutes to about 1 hour after administration of the composition. In yet another embodiment of the present invention, the composition is administered to the subject in an amount to achieve a measurable serum concentration of the proton pump inhibiting agent greater than about 250 ng/ml within about 30 minutes and to maintain a serum concentration of the proton pump inhibiting agent of greater than about 150 ng/ml from about 30 minutes to about 1 hour after administration of the composition. In another embodiment of the present invention, the composition is administered to the subject in an amount to achieve a measurable serum concentration of the proton pump inhibiting agent greater than about 350 ng/ml within about 30 minutes and to maintain a serum concentration of the proton pump inhibiting agent of greater than about 150 ng/ml from about 30 minutes to about 1 hour after administration of the composition. In another embodiment of the present invention, the composition is administered to the subject in an amount to achieve a measurable serum concentration of the proton pump inhibiting agent greater than about 450 ng/ml within about 30 minutes and to maintain a serum concentration of the proton pump inhibiting agent of greater than about 150 ng/ml from about 30 minutes to about 1 hour after administration of the composition.

In still another embodiment of the present invention, the composition is administered to the subject in an amount to achieve a measurable serum concentration of a non-acid degraded or non-acid reacted proton pump inhibiting agent greater than about 500 ng/ml within about 1 hour after administration of the composition. In yet another embodiment of the present invention, the composition is administered to the subject in an amount to achieve a measurable serum concentration of a non-acid degraded or non-acid reacted proton pump inhibiting agent greater than about 300 ng/ml within about 45 minutes after administration of the composition.

In another embodiment of the present invention, the composition is administered to the subject in an amount sufficient to achieve a maximum serum concentration (Cmax) at a time (Tmax) that is within about 90, 70, 60, 50, 40, 30 or 20 minutes after administration of the composition according to the present invention.

In still another embodiment of the invention, the composition is administered to the subject in an amount sufficient to achieve a maximum serum concentration (Cmax) at a time (Tmax) that is between about 10 and about 90 minutes, between about 10 to about 60 minutes, between about 15 to about 60 minutes or between about 20 to about 60 minutes after administration of the composition according to the present invention. In some specific embodiments, the values of Cmax and Tmax are averages over a test population. In other specific embodiments, the values of Cmax and Tmax are the values for an individual.

In still another embodiment, the composition is administered in an amount sufficient to achieve a maximum serum concentration (Cmax) of from about 400 to about 3000 ng/mL, from about 400 to about 2500 ng/mL, from about 400 to about 2000 ng/mL, from about 400 to about 1500 ng/mL, from about 1000 to about 1500 ng/mL, from about 400 to about 1000 ng/mL or from about 400 to about 700 ng/mL. In some specific embodiments, the values of Cmax and Tmax are averages over a test population. In other specific embodiments, the values of Cmax and Tmax are the values for an individual.

In a further embodiment, the composition is administered in an amount sufficient to achieve a maximum serum concentration (Cmax) of greater than 400 ng/mL, greater than 600 ng/mL, greater than 1000 ng/mL. In some specific embodiments, the values of Cmax and Tmax are averages over a test population. In other specific embodiments, the values of Cmax and Tmax are the values for an individual.

Contemplated compositions of the present invention provide a therapeutic effect as proton pump inhibiting agent medications over an interval of about 5 minutes to about 24 hours after administration, enabling, for example, once-a-day, twice-a-day, three times a day, etc. administration if desired. Generally speaking, one will desire to administer an amount of the compound that is effective to achieve a serum level commensurate with the concentrations found to be effective in vivo for a period of time effective to elicit a therapeutic effect. Determination of these parameters is well within the skill of the art. These considerations are well known in the art and are described in standard textbooks.

In one embodiment of the present invention, the composition is administered to a subject in a gastrointestinal-disorder-effective amount, that is, the composition is administered in an amount that achieves a therapeutically-effective dose of a proton pump inhibiting agent in the blood serum of a subject for a period of time to elicit a desired therapeutic effect. Illustratively, in a fasting adult human (fasting for generally at least 10 hours) the composition is administered to achieve a therapeutically-effective dose of a proton pump inhibiting agent in the blood serum of a subject within about 45 minutes after administration of the composition. In another embodiment of the present invention, a therapeutically-effective dose of the proton pump inhibiting agent is achieved in the blood serum of a subject within about 30 minutes from the time of administration of the composition to the subject. In yet another embodiment, a therapeutically-effective dose of the proton pump inhibiting agent is achieved in the blood serum of a subject within about 20 minutes from the time of administration to the subject. In still another embodiment of the present invention, a therapeutically-effective dose of the proton pump inhibiting agent is achieved in the blood serum of a subject at about 15 minutes from the time of administration of the composition to the subject.

In further embodiments, greater than about 98%; or greater than about 95%; or greater than about 90%; or greater than about 75%; or greater than about 50% of the drug absorbed into the bloodstream is in a non-acid degraded or a non-acid reacted form.

In other embodiments, the pharmaceutical formulations provide a release profile of the proton pump inhibitor, using USP dissolution methods, whereby greater than about 50% of the proton pump inhibitor is released from the composition within about 2 hours; or greater than 50% of the proton pump inhibitor is released from the composition within about 1.5 hours; or greater than 50% of the proton pump inhibitor is released from the composition within about 1 hour after exposure to gastrointestinal fluid. In another embodiment, greater than about 60% of the proton pump inhibitor is released from the composition within about 2 hours; or greater than 60% of the proton pump inhibitor is released from the composition within about 1.5 hours; or greater than 60% of the proton pump inhibitor is released from the composition within about 1 hour after exposure to gastrointestinal fluid. In yet another embodiment, greater than about 70% of the proton pump inhibitor is released from the composition within about 2 hours; or greater than 70% of the proton pump inhibitor is released from the composition within about 1.5 hours; or greater than 70% of the proton pump inhibitor is released from the composition within about 1 hour after exposure to gastrointestinal fluid.

Dosage Forms

The pharmaceutical formulations of the present invention contain desired amounts of microencapsulated proton pump inhibitor and/or dry coated proton pump inhibitor and antacid can be in the form of, e.g., a tablet; including a suspension tablet, a chewable tablet, an effervescent tablet or caplet; a pill; a powder such as a sterile packaged powder, a dispensable powder, and an effervescent powder; a capsule including both soft or hard gelatin capsules such as HPMC capsules; a lozenge; a sachet; a troche; pellets; granules; or aerosol. These pharmaceutical formulations of the present invention can be manufactured by conventional pharmacological techniques.

The amount and types of buffers, proton pump inhibitors, and other excipients useful in each of these dosage forms are described throughout the specification and examples. It should be recognized that where a combination of buffer, proton pump inhibitor and/or excipient, including specific amounts of these components, is described with one dosage form that the same combination could be used for any other suitable dosage form. Moreover, it should be understood that one of skill in the art would, with the teachings found within this application, be able to make any of the dosage forms listed above by combining the components (i.e., amounts and types of PPIs, buffers, and other excipients) described in the different sections of the specification.

Moreover, each of the dosage forms may comprise one or more additional materials such as a pharmaceutically compatible carrier, binder, filling agent, suspending agent, flavoring agent, sweetening agent, disintegrating agent, surfactant, preservative, lubricant, colorant, diluent, solubilizer, moistening agent, stabilizer, wetting agent, anti-adherent, parietal cell activator, anti-foaming agent, antioxidant, chelating agent, antifungal agent, antibacterial agent, or one or more combination thereof.

Parietal cell activators are administered in an amount sufficient to produce the desired stimulatory effect without causing untoward side effects to patients. In one embodiment, the parietal cell activator is administered in an amount of about 5 mg to about 2.5 grams per 20 mg dose of the proton pump inhibitor.

The pharmaceutical compositions of the present invention can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., prilling, spray drying, pan coating, melt granulation, granulation, wurster coating, tangential coating, top spraying, extruding, coacervation and the like.

In one embodiment, the proton pump inhibitor is microencapsulated or dry coated prior to being formulated into one of the above forms. In another embodiment, some or all of the antacid is also microencapsulated prior to being further formulated into one of the above forms. In still other embodiments, using standard coating procedures, such as those described in *Remington's Pharmaceutical Sciences,* 20th Edition (2000), a film coating is provided around the pharmaceutical formulation.

Provided herein are pharmaceutical formulations wherein some or all of the proton pump inhibitor and some or all of the antacid are microencapsulated or dry coated. In some embodiments, only some of the proton pump inhibitor is microencapsulated or dry coated. In other embodiments, all of the proton pump inhibitor is microencapsulated or dry coated. In still other embodiments, only some of the antacid is microencapsulated or dry coated.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, e.g., diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Exemplary Solid Compositions

In some embodiments, the pharmaceutical compositions of the present invention contain desired amounts of proton pump inhibiting inhibitor and antacid and are in a solid dosage form.

In other embodiments, the pharmaceutical compositions of the present invention contain desired amounts of proton pump inhibitor and antacid and are administered in the form of a capsule (including both soft or hard capsules, e.g., capsules made from animal-derived gelatin or plant-derived HPMC).

Solid compositions, e.g., tablets, chewable tablets, effervescent tablets, and capsules, are prepared by mixing the microencapsulated proton pump inhibitor or dry coated proton pump inhibitor with one or more antacid and pharmaceutical excipients to form a bulk blend composition. When using dry coated proton pump inhibitor, mixing with additional antacid is optional. When referring to these bulk blend compositions as homogeneous, it is meant that the microencapsulated or dry coated proton pump inhibitor and antacid are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluent.

Compressed tablets are solid dosage forms prepared by compacting the bulk blend compositions described above. In various embodiments, compressed tablets of the present invention will comprise one or more flavoring agents. In other embodiments, the compressed tablets will comprise a film surrounding the final compressed tablet. In other embodiments, the compressed tablets comprise one or more excipients and/or flavoring agents.

A capsule may be prepared, e.g., by placing the bulk blend composition, described above, inside of a capsule. In some embodiments, the pharmaceutical compositions of the present invention contain desired amounts of proton pump inhibiting inhibitor and antacid and are in a solid dosage form. In other embodiments, the pharmaceutical compositions of the present invention contain desired amounts of proton pump inhibitor and antacid and are administered in the form of a capsule (including both soft and hard capsules, e.g., capsules made from animal-derived gelatin or plant-derived HPMC). The pharmaceutical compositions of the present invention can be manufactured by conventional pharmacological techniques.

A chewable tablet may be prepared by compacting bulk blend compositions, described above. In one embodiment, the chewable tablet comprises a material useful for enhancing the shelf-life of the pharmaceutical formulation. In some embodiments, the proton pump inhibitor is dry coated. In another embodiment, microencapsulated material has taste-masking properties. In various other embodiments, the chewable tablet comprises one or more flavoring agents and one ore more taste-masking materials. In yet other embodiments the chewable tablet comprises both a material useful for enhancing the shelf-life of the pharmaceutical formulation and one or more flavoring agents.

In various embodiments, the microencapsulated or dry coated proton pump inhibitor, antacid, and optionally one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the antacid and the proton pump inhibitor into the gastrointestinal fluid. When at least 50% of the pharmaceutical composition has disintegrated, the compressed mass has substantially disintegrated.

In specific embodiments, chewable tablets are prepared using micronized proton pump inhibitor that has been combined with various combinations of potential excipients. In particular embodiments, micronized omeprazole is combined with various colorants, flavorings and other taste masking excipients. In specific embodiments, acidity in particular colorants, flavorings or other taste masking excipients can give rise to instability of the proton pump inhibitor.

In order to provide enhanced stability, some embodiments provide for encapsulation of micronized proton pump inhibitor in an immediate release coating. The immediate release coating is designed to protect the micronized proton pump inhibitor from degradation by acidic excipients, such as flavor components.

Exemplary Powder Compositions

A powder for suspension may be prepared by combining microencapsulated proton pump inhibitor and one or more antacid. In various embodiments, the powder may comprise one or more pharmaceutical excipients. In some embodiments, the proton pump inhibitor is micronized. Other embodiments of the present invention also comprise a suspending agent and/or a wetting agent.

Effervescent powders are also prepared in accordance with the present invention. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6 or higher.

The method of preparation of the effervescent granules of the present invention employs three basic processes: wet granulation, dry granulation and fusion. The fusion method is used for the preparation of most commercial effervescent powders. It should be noted that, although these methods are intended for the preparation of granules, the formulations of effervescent salts of the present invention could also be prepared as tablets, according to known technology for tablet preparation.

Wet granulation is one of the oldest methods of granule preparation. The individual steps in the wet granulation process of tablet preparation include milling and sieving of the ingredients, dry powder mixing, wet massing, granulation, and final grinding. In various embodiments, the microencapsulated omeprazole is added to the other excipients of the pharmaceutical formulation after they have been wet granulated.

Dry granulation by slugging involves compressing a powder mixture into a rough tablet or "slug" on a heavy-duty rotary tablet press. The slugs are then broken up into granular particles by a grinding or milling operation, usually by passage through an oscillation granulator. The individual steps include mixing of the powders, compressing (slugging) and grinding (slug reduction or granulation). In a larger scale operation, roller compaction can be used instead of "slugging". Roller compaction procedure is well-known to ones skilled in the art. No wet binder or moisture is involved in any of the dry granulation steps. In some embodiments, the microencapsulated omeprazole is dry granulated with other excipients in the pharmaceutical formulation. In other embodiments, the microencapsulated omeprazole is added to other excipients of the pharmaceutical formulation after they have been dry granulated.

Other Exemplary Compositions

Pharmaceutical compositions suitable for buccal (sublingual) administration include, e.g., lozenges in a flavored base, such as sucrose, acacia, tragacanth, and pastilles comprising microencapsulated proton pump inhibitor in an inert base such as gelatin, glycerin, sucrose, and acacia are also provided herein.

Many other types of release delivery systems are available and known to those of ordinary skill in the art. Examples of such delivery systems include, e.g., polymer-based systems, such as polylactic and polyglycolic acid, plyanhydrides and polycaprolactone; nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings; compressed tablets using conventional binders and excipients partially fused implants and the like. See, e.g., Liberman et al., *Pharmaceutical Dosage Forms,* 2 Ed., Vol. 1, pp. 209-214 (1990).

In some embodiments, the pharmaceutical composition comprises (a) microencapsulated proton pump inhibitor; and (b) at least one antacid; wherein the pharmaceutical composition is made by the process of (a) microencapsulating some or all of the proton pump inhibitor; and (b) dry blending the microencapsulated material with some or all of the at least one antacid. In other embodiments, the pharmaceutical composition comprises (a) microencapsulated proton pump inhibitor, and (b) at least one antacid, wherein the microencapsulated proton pump inhibitor is made by the process of spray drying the proton pump inhibitor with a microencapsulating material. In still other embodiments, the pharmaceutical composition comprises (a) microencapsulated proton pump inhibitor, and (b) at least one antacid, wherein the pharmaceutical composition is made by the process of (a) microencapsulating some or all of the proton pump inhibitor, and (b) blending the microencapsulated material with some or all of the at least one antacid.

Treatment

Initial treatment of a subject suffering from a disease, condition or disorder where treatment with an inhibitor of $H^+/K^+$-ATPase is indicated can begin with the dosages indicated above. Treatment is generally continued as necessary over a period of hours, days, or weeks to several months or years until the disease, condition or disorder has been controlled or eliminated. Subjects undergoing treatment with the compositions disclosed herein can be routinely monitored by any of the methods well known in the art to determine the effectiveness of therapy. Continuous analysis of such data permits modification of the treatment regimen during therapy so that optimal effective amounts of compounds of the present invention are administered at any point in time, and so that the duration of treatment can be determined as well. In this way, the treatment regimen/dosing schedule can be rationally modified over the course of therapy so that the lowest amount of an inhibitor of $H^+/K^+$-ATPase exhibiting satisfactory effectiveness is administered, and so that administration is continued only so long as is necessary to successfully treat the disease, condition or disorder.

In one embodiment, the pharmaceutical formulations are useful for treating a condition, disease or disorder where treatment with a proton pump inhibitor is indicated. In other embodiments, the treatment method comprises oral administration of one or more compositions of the present invention to a subject in need thereof in an amount effective at treating the condition, disease, disorder. In another embodiment, the disease, condition or disorder is a gastrointestinal disorder. The dosage regimen to prevent, give relief from, or ameliorate the disease, condition or disorder can be modified in accordance with a variety of factors. These factors include the type, age, weight, sex, diet, and medical condition of the subject and the severity of the disorder or disease. Thus, the dosage regimen actually employed can vary widely and therefore can deviate from the dosage regimens set forth herein.

In some embodiments, the pharmaceutical formulation is administered post meal. In further embodiments, the pharmaceutical formulation administered post meal is in the form of a chewable tablet.

The present invention also includes methods of treating, preventing, reversing, halting or slowing the progression of a gastrointestinal disorder once it becomes clinically evident, or treating the symptoms associated with, or related to the gastrointestinal disorder, by administering to the subject a composition of the present invention. The subject may already have a gastrointestinal disorder at the time of administration, or be at risk of developing a gastrointestinal disorder. The symptoms or conditions of a gastrointestinal disorder in a subject can be determined by one skilled in the art and are described in standard textbooks. The method comprises the oral administration a gastrointestinal-disorder-effective amount of one or more compositions of the present invention to a subject in need thereof.

Gastrointestinal disorders include, e.g., duodenal ulcer disease, gastrointestinal ulcer disease, gastroesophageal reflux disease, erosive esophagitis, poorly responsive symptomatic gastroesophageal reflux disease, pathological gastrointestinal hypersecretory disease, Zollinger Ellison Syndrome, and acid dyspepsia. In one embodiment of the present invention, the gastrointestinal disorder is heartburn.

Besides being useful for human treatment, the present invention is also useful for other subjects including veterinary animals, reptiles, birds, exotic animals and farm animals, including mammals, rodents, and the like. Mammals include primates, e.g., a monkey, or a lemur, horses, dogs, pigs, or cats. Rodents includes rats, mice, squirrels, or guinea pigs.

In various embodiments of the present invention, the compositions are designed to produce release of the proton pump inhibitor to the site of delivery (typically the stomach), while substantially preventing or inhibiting acid degradation of the proton pump inhibitor.

In various embodiments of the present invention, the compositions are designed to produce release of the proton pump inhibitor for immediate release in vitro dissolution profile, which is well accepted to by those in the arts to mean drug release of greater than 70% (Q70) in 45 minutes in a USP dissolution test.

In vitro dissolution rate contemplated by the present invention include drug release of greater than 70% (Q70) in 15 minutes in a media with a wide pH range of 1-8.

Combination Therapy

The present pharmaceutical compositions can also be used in combination ("combination therapy") with another pharmaceutical agent that is indicated for treating or preventing a gastrointestinal disorder, such as, e.g., an anti-bacterial agent, an alginate, a prokinetic agent, a H2 antagonist, an antacid, or sucralfate, which are commonly administered to minimize the pain and/or complications related to this disorder.

Combination therapies contemplated by the present invention include administration of a pharmaceutical formulation of the present invention in conjunction with another pharmaceutically active agent that is indicated for treating or preventing a gastrointestinal disorder in a subject, as part of a specific treatment regimen intended to provide a beneficial effect from the co-action of these therapeutic agents for the treatment of a gastrointestinal disorder. The beneficial effect of the combination includes, but is not limited to, pharmacokinetic or pharmacodynamic co-action resulting from the combination of therapeutic agents. Administration of these therapeutic agents in combination typically is carried out over a defined time period (usually substantially simultaneously, minutes, hours, days, weeks, months or years depending upon the combination selected).

Combination therapies of the present invention are also intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, e.g., by administering to the subject a single tablet or capsule having a fixed ratio of each therapeutic agent or in multiple, single capsules, or tablets for each of the therapeutic agents. Sequential or substantially simultaneous administration of each therapeutic agent can be effected by any appropriate route.

The composition of the present invention can be administered orally or nasogastrointestinal, while the other therapeutic agent of the combination can be administered by any appropriate route for that particular agent, including, but not limited to, an oral route, a percutaneous route, an intravenous route, an intramuscular route, or by direct absorption through mucous membrane tissues. For example, the composition of the present invention is administered orally or nasogastrointestinal and the therapeutic agent of the combination may be administered orally, or percutaneously. The sequence in which the therapeutic agents are administered is not narrowly critical. Combination therapy also can embrace the administration of the therapeutic agents as described above in further combination with other biologically active ingredients, such as, but not limited to, a pain reliever, such as a steroidal or nonsteroidal anti-inflammatory drug, or an agent for improving stomach motility, e.g., and with non-drug therapies, such as, but not limited to, surgery.

The therapeutic compounds which make up the combination therapy may be a combined dosage form or in separate dosage forms intended for substantially simultaneous administration. The therapeutic compounds that make up the combination therapy may also be administered sequentially, with either therapeutic compound being administered by a regimen calling for two step administration. Thus, a regimen may call for sequential administration of the therapeutic compounds with spaced-apart administration of the separate, active agents. The time period between the multiple administration steps may range from, e.g., a few minutes to several hours to days, depending upon the properties of each therapeutic compound such as potency, solubility, bioavailability, plasma half-life and kinetic profile of the therapeutic compound, as well as depending upon the effect of food ingestion and the age and condition of the subject. Circadian variation of the target molecule concentration may also determine the optimal dose interval.

The therapeutic compounds of the combined therapies contemplated by the present invention, whether administered simultaneously, substantially simultaneously, or sequentially, may involve a regimen calling for administration of one therapeutic compound by oral route and another therapeutic compound by an oral route, a percutaneous route, an intravenous route, an intramuscular route, or by direct absorption through mucous membrane tissues, for example. Whether the therapeutic compounds of the combined therapy are administered orally, by inhalation spray, rectally, topically, buccally, sublingually, or parenterally (e.g., subcutaneous, intramuscular, intravenous and intradermal injections, or infusion techniques), separately or together, each such therapeutic compound will be contained in a suitable pharmaceutical formulation of pharmaceutically-acceptable excipients, diluents or other formulations components.

In one embodiment, the pharmaceutical formulations of the present invention are administered with low strength enteric coated Aspirin. In another embodiment, the second active pharmaceutical, e.g., Aspirin or an NSAID, used in combination with the pharmaceutical formulations of the present invention, is enteric coated. In other embodiments, antacid present in the pharmaceutical formulations of the present invention increase the pH level of the gastrointestinal fluid, thereby allowing part or all of the enteric coating on the second active pharmaceutical to dissolve in the stomach.

For the sake of brevity, all patents and other references cited herein are incorporated by reference in their entirety.

EXAMPLES

The present invention is further illustrated by the following examples, which should not be construed as limiting in any way. The experimental procedures to generate the data shown are discussed in more detail below. For all formulations herein, multiple doses may be proportionally compounded as is known in the art. The coatings, layers and encapsulations are applied in conventional ways using equipment customary for these purposes.

The invention has been described in an illustrative manner, and it is to be understood that the terminology used is intended to be in the nature of description rather than of limitation.

Example 1A

Microencapsulation Materials and Methods

Microencapsulation Process Using Spinning Disk Atomization

The basic operation for the spinning disk process used (microencapsulation by spray drying) was as follows: An encapsulation solution or suspension was prepared by dissolving the encapsulation (or shell) material in the appropriate solvent. Omeprazole (or the proton pump inhibitor) was dispersed in the coating solution and fed onto the center of the spinning disk or spray dryer which is pre-heated. One of three atomization methods can be used to make droplets of the feed solution/suspension. The microspheres were formed by removal of the solvent using heated airflow inside the drying chamber and collected as a powder using a cyclone separator.

Atomization of the feed solution/suspension can be achieved by major methods in a spray dryer, by rotary atomization using a spinning disc, by high pressure-nozzle, or by two fluid nozzles. A thin film was produced across the surface of the disk and atomization occurs as the coating material left the periphery of the disk in a rotary atomization process. The microspheres were formed by removal of the solvent using heated airflow inside the atomization chamber and collected as a free-flowing powder using a cyclone separator. High pressure nozzle utilizes a high pressure pump to feed the solution/suspension through a various size nozzle so droplets form when injected into the drying chamber. The pressure energy is converted to kinetic energy and the feed issues form the orifice as a high speed film that readily disintegrates into droplets. For the two fluid nozzle, the atomization is created due to high frictional shearing forces between the liquid surface and the air having a high velocity even at sonic velocities and sometimes rotated to obtain maximum atomization.

Spray Drying Microencapsulation Process

The basic operation for the microencapsulation by spray drying was as follows: An encapsulation solution or suspension was prepared by dissolving the shell material in the appropriate solvent. Proton pump inhibitor was dispersed in the coating solution and fed onto the spray dryer which is pre-heated. One of the three atomization method can be used to make droplet of the feed solution/suspension. The microspheres were formed by removal of the solvent using heated airflow inside the drying chamber and collected as a powder using a cyclone separator.

A spray dryer with attached fluid-bed dryer for sizing of dried particles and/or agglomeration if desired can be also used. Recycling of the super-fine particles from the cyclones back to the spray dryer inlet would allow the agglomeration to form desired particle size distribution.

The dissolution profiles of the microencapsulated omeprazole were determined by a method similar to the HPLC method outlined in Example 10, described below. The size of the microspheres was determined by using a microscopic optical method similar to the one outlined in Example 11.

TABLE 1A

| Sample | OME load (wt %) Theoretical/ Analytical | Material | Method | Size | % Omeprazole Released (wt %) | | | |
|---|---|---|---|---|---|---|---|---|
| | | | | | 5 min | 30 min | 45 min | 2 hour |
| 4 | 25%/22% | KLX BHT (0.1% of KLX) | Disk-hot melt | 25-125 micron | -1.1 1.5 | 10.3 10.1 | 22.2 17.3 | 36.5 34.6 |
| 5 | 25%/23% | Methocel A15LV PEG 3350 (5%) | Spray dry | 5-30 micron | 103.7 113.1 | 100.7 103.7 | 99.2 102.7 | 98.3 101.0 |
| 6 | 25%/26% | Methocel A15LV PEG 300 (5%) BHT (0.1%) | Spray dry | 5-30 micron | 77.5 120.3 | 85.6 87.3 | 85.0 90.4 | 86.1 86.3 |
| 7 | 25%/39% | Methocel A15LV Span 20 (5%) BHT (0.1%) | Spray dry | 5-30 micron | 29.8 33.8 | 37.7 30.7 | 41.5 28.2 | 51.7 38.0 |
| 8 | 25%/24% | Methocel A15LV BHT (0.1%) | Spray dry | 5-30 micron | 89.8 93.1 | 97.2 82.5 | 95.1 83.9 | 90.4 84.8 |
| 10 | 3%/2% | Methocel A15LV PEG 3350 (5%) BHT (0.1%) Sodium bicarbonate | Spray dry | 5-30 micron | 94.4 104.6 | 104.7 99.2 | 102.7 98.2 | 97.9 93.2 |
| 11 | 25%/20% | Opadry YS-1-7003 PEG 3350 (5%) BHT (0.1%) | Spray dry | 5-30 micron | 91.4 99.3 | 103.1 98.8 | 100.1 95.8 | 94.8 91.0 |
| 12 | 25%/27% | Methocel K4M PEG 3350 (10%) BHT | Spray dry | 5-30 micron | 134.1 73.2 | 92.9 88.4 74.5 78.7 | 86.9 85.3 75.3 77.2 | 85.0 84.2 73.5 74.1 |
| 13 | 25%/26% | Kollicoat IR PEG 3350 (5%) BHT | Spray dry | 5-30 micron | 99.1 89.7 | 94.7 87.7 | 94.2 84.9 | 91.9 84.6 |
| 14 | 25%/21% | Eudragit RD 100 PEG 3350 (5%) BHT (0.1%) | Spray dry | 5-30 micron | 111.5 48.9 | 72.6 73.1 | 76.9 74.1 | 73.0 73.7 |
| 15 | 25%/26% | Klucel (HPC) PEG 3350 (5%) BHT (0.1%) | Spray dry | 5-30 micron | | 76.8 69.6 | 82.1 71.7 | 83.1 73.1 |
| 16 | 25%/25% | Ethocel #7 | Disk-solvent | 25-125 micron | 5.4 14 | 9.3 9.7 | 13.8 12.4 | 23.8 22.5 |
| 17 | 25%/25% | Ethocel (50%) Methocel E5 (50%) | Disk-solvent | 25-125 micron | 122.6 113.4 | 105.9 100.4 | 106.2 103.9 | 97.6 97.9 |
| 18 | 25%/25% | Ethocel (75%) Methocel (25%) | Disk-solvent | 25-125 micron | | 61.6 44.3 37.0 40.5 | 73.0 53.8 47.0 47.6 | 60.9 67.9 59.2 61.1 |
| 19 | 25%/25% | Methocel | Disk-solvent | 25-125 micron | | 78.7 84.8 78.0 79.0 | 80.5 84.8 80.3 75.2 | 78.1 78.7 78.1 77.0 |

TABLE 1A-continued

| Sample | OME load (wt %) Theoretical/ Analytical | Material | Method | Size | % Omeprazole Released (wt %) | | | |
|---|---|---|---|---|---|---|---|---|
| | | | | | 5 min | 30 min | 45 min | 2 hour |
| 20 | 2.4%/5% | Ethocel Sodium Bicarbonate | Disk-solvent | 25-125 micron, | | 25.0<br>23.2<br>19.3<br>16.1 | 28.8<br>33.3<br>20.6<br>17.4 | 33.6<br>30.3<br>27.4<br>22.6 |
| 21 | 25%/22% | Ethocel PEG 3350 (5%) | Disk-solvent | 25-125 micron | | 31.7<br>38.1 | 44.6<br>52.5 | 59.4<br>59.6 |
| 22 | 25%/22% | Ethocel (50%) Klucel EXAF (50%) | Disk-solvent | 25-125 micron | | 89.9<br>84.5 | 88.6<br>88.4 | 86.7<br>85.0 |
| 23 | 25%/22% | Klucel | Disk-solvent | 25-100 microns | | 88.1<br>83.2 | 90.2<br>82.9 | 88.1<br>82.3 |
| 24 | 25%/22% | Sepifilm LP | Disk-solvent | 25-100 micron | | 97.0<br>90.3 | 95.2<br>89.8 | 92.2<br>90.1 |
| 25 | 25%/23% | Eudragit E100 | Disk-solvent | 25-80 micron | | 13.2<br>8.2 | 17.0<br>12.1 | 24.8<br>20.2 |
| 26 | 40%/35% | Eudragit E100 | Disk-solvent | 25-80 micron | | 5.1<br>13.1 | 6.4<br>16.4 | 11.5<br>23.5 |
| 27 | 40%/38% | Eudragit E100 Span 20 (5%) | Disk-solvent | 25-80 micron | | 15.0<br>16.9 | 16.2<br>20.1 | 27.0<br>26.3 |
| 28 | 40%/35% | Eudragit E100 PEG 300 (5%) | Disk-solvent | 25-80 micron | | 16.3<br>16.0 | 19.5<br>12.9 | 28.8<br>28.5 |
| 29 | 25%/25% | Eudragit EPO | Disk-solvent | 25-80 micron | | 15.3<br>11.9 | 17.8<br>14.5 | 25.6<br>21.2 |
| 30 | 40%/36% | Eudragit EPO | Disk-solvent | 25-90 micron | | 15.2<br>17.5 | 17.8<br>17.5 | 27.1<br>30.9 |
| 31 | 25%/24% | Opadry AMB | Spray dry | <30 micron | | 105.8<br>105.8 | 104.0<br>103.8 | 77.5<br>98.6 |
| 34 | 25%/23% | Kollicoat IR | Spray dry | | | 99.4<br>101.6 | 94.0<br>99.5 | 83.4<br>96.3 |
| 35 | 25%/26% | Kollicoat IR Sodium bicarbonate | Spray dry | <30 micron | | 104.2<br>99.1 | 97.0<br>95.3 | 86.3<br>91.1 |
| 38 | 25%/26% | Klucel Sodium bicarbonate | Spray dry | <30 micron | | 81.3<br>93.8 | 77.3<br>90.5 | 72.1<br>85.8 |
| 39 | 25%/15% | Klucel(60%) Sucraolse (10%) Sodium bicarbonate (30%) | Spray dry | <50 micron | | 91.4<br>101.5 | 86.4<br>97.2 | 82.6<br>93.4 |
| 40 | 50%/47% | Eudragit EPO | Disk-solvent | 20-75 microns | | 10.2<br>10.6 | 14.0<br>13.6 | 23.5<br>24.3 |
| 41 | 60%/57% | Eudragit EPO | Disk-solvent | 20-90 microns | | 13.9<br>6.7 | 17.5<br>17.4 | 35.7<br>33.8 |
| 42 | 40%/39% | Eudragit EPO(67%) Sodium bicarb(33%) | Disk-solvent | 20-85 microns | | 17.0<br>16.4 | 20.2<br>19.4 | 34.3<br>20.2 |
| 43 | 48%/48% | EudragitEPO (61.5%) PEG 300(11.5%) PEG 3350 (3.8%) Sod bicarb(23.2%) | Disk-solvent | 20-110 microns | | 17.3<br>22.2<br>27.8(pH5)<br>22.4(pH5)<br>59.2(pH6)<br>55.8(pH6) | 28.0<br>24.9<br>1.9(pH5)<br>1.7(pH5)<br>41.4(pH6)<br>39.5(pH6) | 51.0<br>50.3<br>0(pH5)<br>0(pH5)<br>25.2(pH6)<br>23.9(pH6) |
| 44 | 70%/66% | Eudragit EPO | Disk-solvent | 20-100 microns | | 21.7<br>21.3<br>27.8(pH5)<br>17.8(pH5)<br>59.1(pH6)<br>31.6(pH6) | 27.1<br>25.2<br>0.9(pH5)<br>0.5(pH5)<br>39.0(pH6)<br>38.4(pH6) | 43.6<br>54.4<br>0(pH5)<br>0(pH5)<br>23.6(pH6)<br>22.8(pH6) |
| 45 | 25%/26% | Opadry AMB (No TiO$_2$) | Spray dry | | | 90.0<br>87.1 | 84.1<br>84.6 | 79.8<br>79.6 |
| 46 | 25%/24% | Opadry AMB (No TiO$_2$) | Spray dry | | | 56.2<br>90.0 | 85.0<br>85.8 | 81.6<br>81.7 |
| 47 | 25%/24% | Opadry AMB (No TiO$_2$) BHT (0.1%) | Spray dry | | | 93.4<br>88.9 | 90.0<br>87.5 | 86.8<br>82.7 |
| 51 | 66%/ | Eudragit EPO | Disk-solvent | 20-100 microns | | 21.7<br>21.3 | 27.1<br>25.2 | 43.6<br>54.4 |
| 52 | 24%/ | Opadry AMB BHT | Spray Dry (aqueous) | 5-30 microns | | 93.4<br>88.9 | 90.0<br>87.5 | 86.8<br>82.7 |

Example 1B

Microencapsulation of Omeprazole with Klucel-EF—37 wt-%

A suspension containing Klucel EF, sodium bicarbonate and omeprazole was prepared (total solid content of 16.23%) and spray dried using a rotary atomizer. The pH of the suspension was 8.1. Spray rate was 35 Kg/hour and the resulting outlet temperature was 70-85° C. Atomizer speed was 22,000 rpm. The viscosity of the suspension was 680 cps and the pumping system had no difficulty in delivering the suspension to the atomizer. White, fine particles were collected. The median particle size of sample was approximately 80-110 μm. U.S. patent No. 2 in vitro dissolution test showed drug release of >90% in 15 minutes. The amounts of each component are shown below:

| Raw Material | Actual Amount Weighed out (Kg) | Calculated Wt. % in Dried Sample |
| --- | --- | --- |
| Klucel ® EF, NF | 50 | 61.61 |
| Omeprazole, USP | 30 | 36.97 |
| Sodium Bicarbonate (NaHCO$_3$), USP | 1.15 | 1.42 |
| USP Purified Water* | 418.85 | — |
| Total | 500.00 | 100.00 |

Example 1C

Microencapsulation of Omeprazole with Klucel-EF—28 wt-%

A suspension containing Klucel EF, sodium bicarbonate and omeprazole was prepared (total solid content of 16.23%) and spray dried using a rotary atomizer. The pH of the suspension was 8.1. The inlet temperature was 130° C. and the outlet temperature was 84-85° C. Atomizer speed was 27,000 rpm. The viscosity of the suspension was 680 cps and the pumping system had no difficulty in delivering the suspension to the atomizer. White, fine particles were collected. The median particle size of sample was approximately 35-40 μm. U.S. patent No. 2 in vitro dissolution test showed drug release of >35% in 30 minutes. The amounts of each component are shown below:

| Raw Material | Actual Amount Weighed out (Kg) | Calculated Wt. % in Dried Sample |
| --- | --- | --- |
| Klucel ® EF, NF | 10.0 | 70.37 |
| Omeprazole, USP | 4.0 | 28.15 |
| Sodium Bicarbonate (NaHCO$_3$), USP | 0.21 | 1.48 |
| USP Purified Water* | 85.79 | — |
| Total | 100.00 | 100.00 |

Example 1D

Microencapsulation of Omeprazole with Methocel E5

The microencapsulation of omeprazole consisted of two main steps: 1) suspension preparation and 2) spray drying operation. Methocel E5 was weighed out and added into water extremely slowly until a clear, homogeneous. PEG400 was added to the Methocel E5 polymer solution. Omeprazole and sodium bicarbonate were added to the polymer solution with agitation until a milky white, homogeneous suspension was formed. The finished omeprazole suspension was agitated at a minimum speed to prevent settling. The omeprazole suspension was then sprayed using the parameter shown below.

| | |
| --- | --- |
| Inlet Temperature | 135° C. |
| Outlet Temperature | 85° C. |
| Atomizer Rotational Speed | 27,000 rpm |

White, fine particles were collected. The average particle size of sample was approximately 35-54 μm. U.S. Pat. No. 2 in vitro dissolution test showed drug release of >70% in 15 minutes. The amount of each component is shown below:

| Raw Material | Actual Amount Weighed out (Kg) | Calculated Wt. % in Dried Sample |
| --- | --- | --- |
| Methocel ® E5, NF | 3.80 | 60.03 |
| Omeprazole, USP | 1.60 | 25.28 |
| PolyEthylene Glycol 400 (PEG400), NF | 0.80 | 12.64 |
| Sodium Bicarbonate (NaHCO$_3$), USP | 0.13 | 2.05 |
| USP Purified Water | 33.70 | — |
| Total | 40.03 | 100.00 |

Example 1E

Microencapsulation of Omeprazole Using High Pressure Nozzle Spray Drying

A suspension containing hydroxypropyl cellulose, sodium bicarbonate and omeprazole was prepared (total solid content of 15.0%) and spray dried using a high pressure nozzle. The pH of the suspension was 8.5. The inlet temperature was 140-150° C. and the outlet temperature was 79-85° C. Core and the Nozzle size (SK value) used in the spray drying was 72 and 17, respectively. The viscosity of the suspension was in the range of 600-700 cps and the pumping system had no difficulty in delivering the suspension to the atomizer. White, fine particles were collected. The median particle size of sample was approximately 60 μm. The amounts of each component are shown below:

| Raw Material | Actual Amount Weighed out (Kg) | Calculated Wt. % in Dried Sample |
| --- | --- | --- |
| Klucel ®-EF, NF | 70.00 | 61.6 |
| Omeprazole, USP | 42.00 | 37.0 |
| Sodium Bicarbonate (NaHCO$_3$), USP | 1.61 | 1.4 |
| USP Purified Water | 644.00 | — |
| Total | 757.61 | 100.00 |

Example 2A

Preparation of Microencapsulated Omeprazole

The chart below summarizes the wt %, the feed rates used, and the inlet/outlet temperatures for eleven different omeprazole microspheres.

TABLE 2A

| Sample | Method and Solvent | Omeprazole payload in microcapsule (Theoretical/ Analytical) | Microencapsulation Material | Wt % of material | Feed Rate (g/min) | Inlet/ Outlet Temp(° C.) |
|---|---|---|---|---|---|---|
| 53 | Spray dry* Water | 25%/23.3% | Omeprazole (25%) Methocel A15 LV (70%) PEG 3350 (5%) | 5% | 4.2 | 125/70 |
| 54 | Spray dry Water | 25%/24.8% | Omeprazole (25%) Methocel A15 LV (74.9%) BHT (0.1%) | 5% | 4.0 | 125/70 |
| 55 | Spray dry Water | 25%/20.5% | Omeprazole (25%) Opadry YS-1-7003 (70.9%) PEG 3350 (5%) BHT (0.1%) | 5% | 4.2 | 126/60 |
| 56 | Spray dry Water | 25%/26.2% | Omeprazole (25%) Kollicoat IR (70.9%) PEG 3350 (5%) BHT (0.1%) | 10% | 3.0 | 128/85 |
| 57 | Spray dry Water | 25%/21.3% | Omeprazole (25%) Eudragit RD100 (70.9%) PEG 3350 (5%) BHT (0.1%) | 5% | 4.0 | 127/87 |
| 58 | Spray dry Water | 25%/26.0% | Omeprazole (25%) Klucel (70.9%) PEG 3350 (5%) BHT (0.1%) | 5% | 4.2 | 126/83 |
| 59 (not made into tablets) | Spinning disk** 75% Methanol 25% Acetone | | Klucel | 10% | 90 | /52 |
| 60 | Spray dry Water | 25%/26.0% | Omeprazole (25%) Kollicoat (73%) Sodium Bicarb (2%) | 5% | 4.5 | 129/86 |
| 61 | Spray dry Water | 25%/26.3% | Omeprazole (25%) Klucel (73%) Sodium Bicarb (2%) | 5% | 4.5 | 122/84 |
| 62 | Spinning disk 75% Methanol 25% Acetone | 70%/66.1% | Omeprazole (70%) Eudragit EPO (30%) | 10% | 90 | /50 |
| 63 | Spray dry Water | 25%/24.7% | Omeprazole (25%) Opadry AMB (74.9%) BHT (0.1%) | 10% | 4.4 | 124/79 |

*Used a concentric nozzle with 0.055 inch air opening and a 0.028 inch fluid opening.
**Used a 3-inch stainless steel disk rotating at approximately 4,500 rpm.

The amount of encapsulated omeprazole used in each tablet batch varies based on the actual payload of each set of microcapsules to achieve the theoretical dose of 40 mg. The omeprazole was microencapsulated in a similar manner as that described in Example 1. All ingredients are mixed well to achieve a homogeneous blend.

Tablets containing omeprazole microspheres were prepared using a high-speed rotary tablet press (TBCB Pharmaceutical Equipment Group, Model ZPY15). Round, convex tablets with diameters of about 10 mm and an average weight of approximately 600 mg per tablet were prepared.

Chewable tablets were manufactured using the following materials: Encapsulated omeprazole (varied based on payload, to deliver 40 mg potency), sodium bicarbonate (1260 mg), calcium carbonate (790 mg), croscarmellose sodium (64 mg), Klucel (160 mg), Xylitab 100 (380 mg), microcrystalline cellulose (128 mg), sucralose (162 mg), peppermint flavor (34 mg), peach flavor (100 mg), masking powder (60 mg), FD&C Lake No. Red (3 mg), and magnesium stearate (32 mg).

Example 2B

Preparation of Microencapsulated PPIs

Table 2B below summarizes various drug wt %, shell materials, and in-vitro dissolution data for eighteen different proton pump inhibitor microspheres. The atomization method for the spray drying is also listed and is performed in a manner analogous to that listed in Example 1 above.

TABLE 2B

Materials used in Chewable Tablets

| No. | PPI | Shell Material | pH Modifier (Buffer) | Atomization | In Vitro Dissolution |
|---|---|---|---|---|---|
| 2B-2 | Lansoprazole-30% | HPC (Klucel-EF)-69.0% | SC 1% | High Pressure | Q70 in 30 min |
| 2B-3 | Pentoprazole- sodium 45% | HPC (Klucel-EF)-54.0% | SB 1% | High Pressure | Q70 in 30 min |

TABLE 2B-continued

Materials used in Chewable Tablets

| No. | PPI | Shell Material | pH Modifier (Buffer) | Atomization | In Vitro Dissolution |
|---|---|---|---|---|---|
| 2B-4 | Omeprazole-Mg 45% | HPC (Klucel-EF)-54.0% | SB 1% | High Pressure | Q70 in 30 min |
| 2B-5 | Rabeprazole-Na-40% | HPC (Klucel-EF)-59% | SB 1% | Spinning disc | Q70 in 30 min |
| 2B-7 | Lansoprazole-30% | HPMC(Methocel-E5)-64.0% PEG400 5% | SC 1% | Spinning disc | Q70 in 45 min |
| 2B-8 | Pentoprazole-sodium 45% | HPMC (Methocel-E5)-44% PEG400 10% | SC 1% | High Pressure | Q70 in 30 min |
| 2B-9 | Omeprazole-Mg 45% | HPMC (Methocel-E5)-54.9% PEG 400 10% | SB 1% | High Pressure | Q70 in 30 min |
| 2B-10 | Rabeprazole-Na-40% | HPMC (Methocel-E5)-51% PEG400 8% | SC 1% | High Pressure | Q70 in 15 min |
| 2B-11 | Omeprazole-37% | MC (Methocel-A15)-52% PEG400 10% | SB 3% | Spinning disc | Q70 in 30 min |
| 2B-12 | Lansoprazole-30% | MC (Methocel-A15)-57% PEG400 12% | SC 1% | Spinning disc | Q70 in 30 min |
| 2B-13 | Pentoprazole-sodium 45% | MC (Methocel-A15)-54% | SC 1% | High Pressure | Q70 in 30 min |
| 2B-14 | Omeprazole-Mg 45% | MC (Methocel-A15)-54% | SB 1% | High Pressure | Q70 in 30 min |
| 2B-15 | Rabeprazole-Na-40% | MC (Methocel-A15)-59% | SC 1% | High Pressure | Q70 in 30 min |
| 2B-16 | Omeprazole-37% | Klucel-EF 30% MC (Methocel-A15)-22% PEG400 3% | SB 3% | High Pressure | Q70 in 30 min |
| 2B-17 | Omeprazole-37% | Klucel-EF 30% HPMC (Methocel-E5)-22% PEG400 3% | SB 3% | High Pressure | Q70 in 30 min |
| 2B-18 | Lansoprazole-40% | Klucel-EF 30% HPMC (Methocel-E5)-22% PEG400 4% | SC 2% | High Pressure | Q70 in 30 min |

Example 2C

Preparation of Lansoprazole Chewable Tablets

Lansoprazole chewable tablets are manufactured using the following materials: Microencapsulated lansoprazole (30% drug loading-Entry 2B-2 in Table 2B, 100 mg to deliver 30 mg drug potency), sodium bicarbonate (420 mg), direct-compression grade magnesium hydroxide (contains 5% starch, 526 mg to deliver 500 mg magnesium hydroxide), [total buffer=24.1 mEq], croscarmellose sodium (45 mg), Klucel (80 mg), Xylitab 300 (200 mg), sucralose (70 mg), fruit flavor crystals (52 mg), masking powder (30 mg), Lake FD & C Red #40 (2 mg), and magnesium stearate (20 mg).

The amount of microencapsulated lansoprazole used in each tablet batch is based on the actual payload of microcapsules to achieve the theoretical dose of 30 mg lansoprazole per tablet. Lansoprazole is microencapsulated in a similar manner as that described in Example 1 and 2. All ingredients are mixed well to achieve a homogenous bulk blend which is then compressed to round tablets.

Example 2D

Preparation of Omeprazole Salt Caplets

Omeprazole magnesium tablets are manufactured using the following materials: Microencapsulated Omeprazole-Mg salt (45% drug loading-Entry 2B-14 in Table 2B, 89 mg to deliver 40 mg omeprazole), sodium bicarbonate (420 mg), direct-compression grade magnesium hydroxide (contains 5% starch, 337 mg to deliver 320 mg magnesium hydroxide), croscarmellose sodium (50 mg), Klucel-EXF (50 mg), and magnesium stearate (7 mg) [total 16 mEq in swallowable tablet or caplet].

The amount of microencapsulated omeprazole used in each tablet batch is based on the actual payload of microcapsules to achieve the theoretical dose of 40 mg omeprazole per tablet (44.5 mg of omeprazole magnesium salt trihydrate). Omeprazole magnesium salt is microencapsulated in a similar manner as that described in Example 1 and 2. All ingredients are mixed well to achieve a homogenous bulk blend which is then compressed to capsule shaped tablets.

Example 2E

Preparation of Pantoprazole Chewable Tablets

Pantoprazole chewable tablets are manufactured using the following materials: Microencapsulated pentoprazole (45% drug loading-Entry 2B-8 in Table 2B, 89 mg to deliver 40 mg drug potency), sodium bicarbonate (336 mg), potassium bicarbonate (200 mg) direct-compression grade magnesium hydroxide (contains 5% starch, 430 mg to deliver 408 mg magnesium hydroxide) [total buffer=20 mEq], Klucel (70 mg), Xylitab 100 (200 mg), sucralose (70 mg), mint flavor crystals (52 mg), masking powder (30 mg), Lake FD & C Blue #2 (2 mg), and magnesium stearate (15 mg).

The amount of microencapsulated pantoprazole used in each tablet batch is based on the actual payload of microcapsules to achieve the theoretical dose of 40 mg pentoprazole per tablet. Pantoprazole is microencapsulated in a similar manner as that described in Example 1 and 2. All ingredients are mixed well to achieve a homogenous bulk blend which is then compressed to round tablets.

Example 2F

Preparation of Rabeprazole Sodium Salt Caplets

Rabeprazole sodium caplets (capsule-shaped tablets) are manufactured using the following materials: Microencapsulated Rabeprazole sodium salt (40% drug loading-Entry 2B-10 Table 2B, 106 mg to deliver 40 mg rabeprazole), sodium bicarbonate (336 mg), Direct-compression grade magnesium hydroxide (contains 5% starch, 307 mg to deliver 292 mg magnesium hydroxide), magnesium oxide (101 mg), croscarmellose sodium (50 mg), Klucel-EXF (40 mg), and magnesium stearate (7 mg) [total 14 mEq in swallowable tablet or caplet].

The amount of microencapsulated rabeprazole sodium used in each tablet batch is based on the actual payload of microcapsules to achieve the theoretical dose of 40 mg rabeprazole per tablet (42.5 mg of rabeprazole sodium salt). Rabeprazole sodium salt is microencapsulated in a similar manner as that described in Example 1 and 2. All ingredients are mixed well to achieve a homogenous bulk blend which is then compressed to tablets.

Example 2G

Preparation of Capsules Containing Lansoprazole Capsule

The capsule product is manufactured using the following materials: Microencapsulated lansoprazole (40% drug loading-Entry 2B-18 in Table 2B, 75 mg, to deliver 30 mg potency), sodium bicarbonate (420 mg), magnesium hydroxide (218 mg), magnesium oxide (151 mg) (total buffer=23.3 mEq), croscarmellose sodium (50 mg), and magnesium stearate (5 mg).

The amount of encapsulated omeprazole used in each capsule batch varies based on the actual payload of each set of microcapsules to achieve the theoretical dose of 30 mg. Lansoprazole was microencapsulated in a similar manner as that described in Example 1 and 2. All ingredients are mixed well to achieve a homogenous bulk blend which is then filled into a capsule such as a size (O) hard gelatin capsule.

Example 2H

Preparation of Capsules Containing Lansoprazole Microspheres

The capsule product is manufactured using the following materials: Microencapsulated lansoprazole (40% drug loading-Entry 2B-18 in Table 2B, 75 mg, to deliver 30 mg potency), sodium bicarbonate (600 mg), magnesium hydroxide (270 mg), [total buffer=18.4], croscarmellose sodium (50 mg), and magnesium stearate (7 mg).

The amount of encapsulated omeprazole magnesium salt used in each capsule batch varies based on the actual payload of each set of microcapsules to achieve the theoretical dose of 30 mg lansoprazole per capsule. Omeprazole magnesium salt was microencapsulated in a similar manner as that described in Example 1 and 2. All ingredients are mixed well to achieve a homogenous bulk blend which is then filled into a capsule such as a size zero (0) hard gelatin capsule.

Example 2I

Preparation of Capsules Containing Omeprazole Magnesium Salt Microspheres

The capsule product is manufactured using the following materials: Microencapsulated omeprazole magnesium salt (45% drug loading-Entry 2B-4 in Table 2B, 88 mg to deliver 40 mg potency), sodium bicarbonate (504 mg), magnesium oxide (220 mg) [total buffer=17], croscarmellose sodium (40 mg), and magnesium stearate (7 mg).

The amount of encapsulated omeprazole used in each capsule batch varies based on the actual payload of each set of microcapsules to achieve the theoretical dose of 30 mg per capsule. Omeprazole magnesium salt was microencapsulated in a similar manner as that described in Example 1 and 2. All ingredients are mixed well to achieve a homogenous bulk blend which is then filled into a capsule such as a size zero (0) hard gelatin capsule.

Example 2J

Preparation of Capsules Containing Pentoprazole Microspheres

The capsule product is manufactured using the following materials: Microencapsulated pentoprazole sodium salt (45% drug loading-Entry 2B-13 in Table 2B, 88 mg, to deliver 40 mg potency), sodium bicarbonate (336 mg) (total buffer=15), magnesium oxide (222 mg), croscarmellose sodium (35 mg), and magnesium stearate (7 mg).

The amount of encapsulated pentoprazole sodium salt used in each capsule batch varies based on the actual payload of each set of microcapsules to achieve the theoretical dose of 40 mg neutral pentoprazole per capsule. Pentoprazole sodium salt was microencapsulated in a similar manner as that described in Example 1 and 2. All ingredients are mixed well to achieve a homogenous bulk blend which is then filled into a capsule such as a size one hard gelatin capsule.

Example 3

Preparation of Chewable Tablets

Various chewable tablets are manufactured using the microencapsulate materials described in Examples 1 and 2. The amount of microencapsulated omeprazole used in each chewable tablet batch is based on the actual payload of each set of microcapsules to achieve the theoretical dose. All ingredients are mixed well to achieve a homogenous bulk blend which is then compressed to chewable tablets.

| PPI | Buffering Agent | Sleep Aid | Excipient |
|---|---|---|---|
| 20 mg per chewable tablet (microencapsulated) | 20.6 mEq or 600 mg Mg(OH)₂<br>5.0 mEq or 420 mg NaHCO₃<br>25.6 mEq or 1020 mg total buffer | 0.125 triazolam mg per tablet | 170 mg Xylitab<br>30 mg Ac-Di-Sol<br>100 mg Klucel<br>25 mg cherry flavor<br>15 mg magnesium sterate<br>3 mg Red #40 Lake |
| 40 mg per chewable tablet (microencapsulated) | 24.0 mEq or 700 mg Mg(OH)₂<br>7.2 mEq or 600 mg NaHCO₃<br>31.1 mEq or 1300 mg total buffer | 5 mg zolpidem per tablet | 170 mg Dipac sugar<br>30 mg Ac-Di-Sol<br>120 mg Klucel<br>27 mg grape flavor<br>15 mg magnesium sterate<br>1 mg Red #40 Lake<br>1 mg Blue #2 Lake |
| 15 mg lansoprazole per chewable tablet | 17.1 mEq or 500 mg Mg(OH)₂<br>3.0 mEq or 250 mg NaHCO₃<br>20.1 mEq or 750 mg total buffer | 5 mg zaleprone per tablet | 170 mg Dipac sugar<br>30 mg Ac-Di-Sol<br>120 mg Klucel<br>27 mg grape flavor<br>15 mg magnesium sterate<br>1 mg red #40 lake<br>1 mg blue #2 lake |
| 30 mg lansoprazole per chewable tablet (microencapsulated) | 24.0 mEq or 700 mg Mg(OH)₂<br>5 mEq or 420 mg NaHCO₃<br>29.0 mEq or 1120 mg total buffer | 25 mg diphenhydramine per tablet | 170 mg Xylitab<br>30 mg Ac-Di-Sol<br>100 mg Klucel<br>25 mg cherry flavor<br>15 mg magnesium stearate<br>3 mg Red #40 Lake |

| PPI | Buffering Agent | Prokinetic Agent | Excipient |
|---|---|---|---|
| 20 mg microencapsulated omeprazole per chewable tablet | 20.6 mEq or 600 mg Mg(OH)₂<br>5.0 mEq or 420 mg NaHCO₃<br>25.6 mEq or 1020 mg total buffer | 5 mg Mosapride per tablet | 170 mg Xylitab<br>30 mg Ac-Di-Sol<br>100 mg Klucel<br>40 mg Sucralose<br>25 mg cherry flavor<br>15 mg magnesium stearate<br>3 mg Red #40 Lake |
| 40 mg microencapsulated omeprazole per chewable tablet | 24.0 mEq or 700 mg Mg(OH)₂<br>7.1 mEq or 600 mg NaHCO₃<br>31.1 mEq or 1300 mg total buffer | 10 mg Domperidone per tablet | 170 mg Dipac sugar<br>30 mg Ac-Di-Sol<br>120 mg Klucel<br>27 mg grape flavor<br>15 mg magnesium stearate<br>1 mg Red #40 Lake<br>1 mg Blue #2 Lake |
| 30 mg microencapsulated lansoprazole per chewable tablet | 24.0 mEq or 700 mg Mg(OH)₂<br>5.0 mEq or 420 mg NaHCO₃<br>29.0 mEq or 1120 mg total buffer | 20 mg Clebopride per tablet | 170 mg Xylitab<br>30 mg Ac-Di-Sol<br>100 mg Klucel<br>25 mg cherry flavor<br>15 mg magnesium stearate<br>3 mg Red #40 Lake |
| 60 mg microencapsulated omeprazole per chewable tablet | 15 mEq or 750 mg Ca(OH)₂<br>15 mEq or 1260 mg NaHCO₃<br>30 mEq or 2010 mg total buffer | 10 mg Norcisapride per tablet | 170 mg Xylitab<br>30 mg Ac-Di-Sol<br>100 mg Klucel<br>25 mg cherry flavor<br>15 mg magnesium stearate<br>3 mg Red #40 Lake |
| 40 mg microencapsulated omprazole per chewable tablet | 15 mEq or 750 mg Ca(OH)₂<br>10 mEq or 840 mg NaHCO₃<br>25 mEq or 1590 mg total buffer | 10 mg Cisapride per tablet | 170 mg Xylitab<br>30 mg Ac-Di-Sol<br>100 mg Klucel<br>15 mg mint flavor<br>15 mg magnesium stearate |
| 40 mg microencapsulated omeprazole per bite-disintegration chewable tablet | 24.0 mEq or 700 mg Mg(OH)₂<br>7.1 mEq or 600 mg NaHCO₃<br>31.1 mEq or 1300 mg total buffer | 10 mg Cisapride per tablet | 60 mg sucralose<br>60 mg Ac-Di-Sol<br>60 mg pregelatinized starch<br>30 mg Klucel<br>27 mg grape flavor<br>15 mg magnesium stearate<br>1 mg Red #40 Lake<br>1 mg Blue #2 Lake |
| 30 mg microencapsulated lansoprazole per bite-disintegration chewable tablet | 17.1 mEq or 500 mg Mg(OH)₂<br>5 mEq or 420 mg NaHCO₃<br>22.1 mEq or 920 mg total buffer | 2.5 mg Mosapride per tablet | 60 mg sucralose<br>60 mg Ac-Di-Sol<br>70 mg pregelatinized starch<br>30 mg Klucel<br>25 mg cherry flavor<br>15 mg magnesium stearate<br>3 mg Red #40 Lake |

| | | | |
|---|---|---|---|
| 60 mg microencapsulated omeprazole per bite-disintegration chewable tablet | 15 mEq or 750 mg Ca(OH)$_2$<br>15 mEq or 1260 mg NaHCO$_3$<br>30 mEq or 2010 mg total buffer | 10 mg Domperidone per tablet | 60 mg sucralose<br>60 mg Ac-Di-Sol<br>60 mg pregelatinized starch<br>30 mg Klucel<br>25 mg cherry flavor<br>15 mg magnesium stearate<br>3 mg Red #40 Lake |
| 40 mg microencapsulated omprazole per bite-disintegration chewable tablet | 15 mEq or 750 mg Ca(OH)$_2$<br>10 mEq or 840 mg NaHCO$_3$<br>25 mEq or 1590 mg total buffer | 10 mg Norcisapride | 60 mg sucralose<br>60 mg Ac-Di-Sol<br>60 mg pregelatinized starch<br>30 mg Klucel<br>15 mg mint flavor<br>15 mg magnesium stearate |

| PPI | Antacid | Excipient |
|---|---|---|
| 40 mg microencapsulated omeprazole per chewable tablet | 5.1 mEq or 150 mg Mg(OH)$_2$<br>3.0 mEq or 250 mg NaHCO$_3$<br>8.1 mEq or 400 mg total antacid | 20 mg Ac-Di-Sol<br>40 mg Microcrystalline cellulose (MCC, PH102)<br>7 mg magnesium stearate |
| 15 mg microencapsulated lansoprazole per chewable tablet | 8.6 mEq or 250 mg Mg(OH)$_2$<br>2.4 mEq or 200 mg NaHCO$_3$<br>11.0 mEq or 450 mg total antacid | 30 mg Ac-Di-Sol<br>55 mg Plasdone<br>8 mg magnesium stearate |
| 10 mg microencapsulated omeprazole per c chewable tablet | 3.4 mEq or 100 mg Mg(OH)$_2$<br>3.0 mEq or 250 mg NaHCO$_3$<br>6.4 mEq or 350 mg total antacid | 15 mg Ac-Di-Sol<br>40 mg Klucel<br>6 mg magnesium stearate |
| 40 mg microencapsulated omeprazole per chewable tablet | 5.1 mEq or 150 mg Mg(OH)$_2$<br>3.8 mEq or 315 mg NaHCO$_3$<br>8.9 mEq or 465 mg total antacid | 20 mg Ac-Di-Sol<br>50 mg Microcrystalline Cellulose (MCC, PH102)<br>10 mg magnesium stearate |
| 20 mg microencapsulated omeprazole per chewable tablet | 5.1 mEq or 150 mg Mg(OH)$_2$<br>3.8 mEq or 315 mg NaHCO$_3$<br>8.9 mEq or 465 mg total antacid | 100 mg Xylitab<br>30 mg Ac-Di-Sol<br>80 mg Klucel<br>20 mg Sucralose<br>10 mg cherry flavor<br>10 mg magnesium stearate<br>1 mg Red #40 Lake |
| 40 mg microencapsulated omeprazole per chewable tablet | 7.5 mEq or 220 mg Mg(OH)$_2$<br>2.4 mEq or 200 mg NaHCO$_3$<br>9.9 mEq or 420 mg total antacid | 100 mg Dipac sugar<br>20 mg Ac-Di-Sol<br>80 mg Klucel<br>17 mg grape flavor<br>11 mg magnesium stearate<br>1 mg Red #40 Lake<br>1 mg Blue #2 Lake |
| 30 mg microencapsulated lansoprazole per chewable tablet | 5.1 mEq or 150 mg Mg(OH)$_2$<br>3.8 mEq or 315 mg NaHCO$_3$<br>8.9 mEq or 465 mg total antacid | 70 mg Destab Sugar<br>30 mg Ac-Di-Sol<br>100 mg Klucel<br>20 mg Asulfame-K<br>15 mg cherry flavor<br>9 mg magnesium stearate<br>1 mg Red #40 Lake |
| 60 mg microencapsulated omeprazole per chewable tablet | 4.4 mEq or 220 mg Ca(OH)$_2$<br>3.6 mEq or 300 mg NaHCO$_3$<br>8.0 mEq or 520 mg total antacid | 80 mg Xylitab<br>30 mg Ac-Di-Sol<br>100 mg Klucel<br>35 mg Sucralose<br>10 mg cherry flavor<br>9 mg magnesium stearate<br>2 mg Red #40 Lake |
| 40 mg microencapsulated omeprazole per chewable tablet | 7.0 mEq or 350 mg Ca(OH)$_2$<br>3.0 mEq or 250 mg NaHCO$_3$<br>10.0 mEq or 600 mg total antacid | 70 mg Xylitab<br>30 mg Ac-Di-Sol<br>10 mg Sucralose<br>80 mg Klucel<br>10 mg mint flavor<br>8 mg magnesium stearate |
| 40 mg microencapsulated omeprazole per chewable tablet | 8.0 mEq or 400 mg Ca(OH)$_2$<br>3.6 mEq or 300 mg NaHCO$_3$<br>11.6 mEq or 700 mg total | 20 mg sucralose<br>40 mg Ac-Di-Sol<br>35 mg pregelatinized starch<br>25 mg Klucel<br>15 mg cherry flavor<br>8 mg magnesium stearate<br>1 mg Red #40 Lake |
| 30 mg microencapsulated lansoprazole per chewable tablet | 5.1 mEq or 150 mg Mg(OH)$_2$<br>3.8 mEq or 315 mg NaHCO$_3$<br>8.9 mEq or 465 mg total antacid | 27 mg sucralose<br>40 mg Ac-Di-Sol<br>35 mg pregelatinized starch<br>30 mg Microcrystalline Cellulose (PH101)<br>20 mg cherry flavor |

-continued

| | | |
|---|---|---|
| 60 mg microencapsulated omeprazole per chewable tablet | 7.9 mEq or 230 mg Mg(OH)$_2$<br>3.0 mEq or 250 mg NaHCO$_3$<br>10.9 mEq or 480 mg total antacid | 10 mg magnesium stearate<br>2 mg Red #40 Lake<br>34 mg sucralose<br>30 mg Ac-Di-Sol<br>35 mg pregelatinized starch<br>30 mg Klucel<br>25 mg cherry flavor<br>10 mg magnesium stearate<br>2 mg Red #40 Lake |
| 40 mg microencapsulated omeprazole per chewable tablet | 8.0 mEq or 400 mg Ca(OH)$_2$<br>2.9 mEq or 240 mg NaHCO$_3$<br>10.9 mEq or 640 mg total antacid | 30 mg sucralose<br>40 mg Ac-Di-Sol<br>30 mg pregelatinized starch<br>30 mg Klucel<br>40 mg Xylitab<br>7 mg mint flavor<br>10 mg magnesium stearate |

Example 4

Preparation of Caplets

Various caplets are manufactured using the microencapsulate materials described in Examples 1 and 2. The amount of microencapsulated omeprazole used in each caplet batch is based on the actual payload of each set of microcapsules to achieve the theoretical dose. All ingredients are mixed well to achieve a homogenous bulk blend which is then compressed to caplets.

| PPI | Buffering Agent | Prokinetic Agent | Excipient |
|---|---|---|---|
| 40 mg microencapsulated omeprazole per caplet | 17.1 mEq or 500 mg Mg(OH)$_2$<br>3.0 mEq or 250 mg NaHCO$_3$<br>20.1 mEq or 750 mg total buffer | 20 mg Clebopride per tablet | 20 mg Ac-Di-Sol<br>80 mg Klucel<br>10 mg magnesium stearate |
| 15 mg microencapsulated lansoprazole per caplet | 17.1 mEq or 500 mg Mg(OH)$_2$<br>3.0 mEq or 250 mg NaHCO$_3$<br>20.1 mEq or 750 mg total buffer | 10 mg Clebopride per tablet | 20 mg Ac-Di-Sol<br>80 mg Klucel<br>10 mg magnesium stearate |
| 10 mg microencapsulated omeprazole per caplet | 13.7 mEq or 400 mg Mg(OH)$_2$<br>3.0 mEq or 250 mg NaHCO$_3$<br>16.7 mEq or 650 mg total buffer | 10 mg Cisapride pre tablet | 20 mg Ac-Di-Sol<br>80 mg Klucel<br>10 mg magnesium stearate |
| 40 mg microencapsulated omeprazole per caplet | 20.6 mEq or 600 mg Mg(OH)$_2$<br>3.0 mEq or 250 mg NaHCO$_3$<br>23.6 mEq or 850 mg total buffer | 10 mg Metoclopramide per tablet | 20 mg Ac-Di-Sol<br>80 mg Klucel<br>10 mg magnesium stearate |

| PPI | Buffering Agent | NSAID | Excipient |
|---|---|---|---|
| 40 mg microencapsulated omeprazole per caplet | 17.1 mEq or 500 mg Mg(OH)$_2$<br>3.0 mEq or 250 mg NaHCO$_3$<br>20.1 mEq or 750 mg total buffer | 81 mg aspirin per tablet | 20 mg Ac-Di-Sol<br>80 mg Klucel<br>10 mg magnesium stearate |
| 15 mg microencapsulated lansoprazole per caplet | 17.1 mEq or 500 mg Mg(OH)$_2$<br>3.0 mEq or 250 mg NaHCO$_3$<br>20.1 mEq or 750 mg total buffer | 75 mg indomethacin per tablet | 20 mg Ac-Di-Sol<br>80 mg Klucel<br>10 mg magnesium stearate |
| 10 mg microencapsulated omeprazole per caplet | 13.7 mEq or 400 mg Mg(OH)$_2$<br>3.0 mEq or 250 mg NaHCO$_3$<br>16.7 mEq or 650 mg total buffer | 200 mgs Ibupropene per tablet | 20 mg Ac-Di-Sol<br>80 mg Klucel<br>10 mg magnesium stearate |
| 40 mg microencapsulated omeprazole per caplet | 20.6 mEq or 600 mg Mg(OH)$_2$<br>3.0 mEq or 250 mg NaHCO$_3$<br>23.6 mEq or 850 mg total buffer | 100 mgs aspirin per tablet | 20 mg Ac-Di-Sol<br>80 mg Klucel<br>10 mg magnesium stearate |
| 20 mg microencapsulated omeprazole per caplet | 20.6 mEq or 600 mg Mg(OH)$_2$<br>5.0 mEq or 420 mg NaHCO$_3$<br>25.6 mEq or 1020 mg total buffer | 25 mg rofecoxib per tablet | 170 mg Xylitab<br>30 mg Ac-Di-Sol<br>100 mg Klucel<br>40 mg Sucralose<br>25 mg cherry flavor |

| | | | 15 mg magnesium stearate |
| | | | 3 mg Red #40 Lake |
| 40 mg microencapsulated omeprazole per caplet | 24.0 mEq or 700 mg Mg(OH)$_2$<br>7.1 mEq or 600 mg NaHCO$_3$<br>31.1 mEq or 1300 mg total buffer | 100 mg diclofenac per tablet | 170 mg Dipac sugar<br>30 mg Ac-Di-Sol<br>120 mg Klucel<br>27 mg grape flavor<br>15 mg magnesium stearate<br>1 mg Red #40 Lake<br>1 mg Blue #2 Lake |
| 30 mg microencapsulated lansoprazole per caplet | 24.0 mEq or 700 mg Mg(OH)$_2$<br>5.0 mEq or 420 mg NaHCO$_3$<br>29.0 mEq or 1120 mg total buffer | 400 mg aspirin and 400 mg enteric coated aspirin per tablet | 170 mg Xylitab<br>30 mg Ac-Di-Sol<br>100 mg Klucel<br>25 mg cherry flavor<br>15 mg magnesium stearate<br>3 mg Red #40 Lake |
| 60 mg microencapsulated omeprazole per caplet | 15 mEq or 750 mg Ca(OH)$_2$<br>15 mEq or 1260 mg NaHCO$_3$<br>30 mEq or 2010 mg total buffer | 600 mg oxaprozin per tablet | 170 mg Xylitab<br>30 mg Ac-Di-Sol<br>100 mg Klucel<br>25 mg cherry flavor<br>15 mg magnesium stearate<br>3 mg Red #40 Lake |
| 40 mg microencapsulated omprazole per caplet | 15 mEq or 750 mg Ca(OH)$_2$<br>10 mEq or 840 mg NaHCO$_3$<br>25 mEq or 1590 mg total buffer | 100 mg aspirin per tablet | 170 mg Xylitab<br>30 mg Ac-Di-Sol<br>100 mg Klucel<br>15 mg mint flavor<br>15 mg magnesium stearate |
| 40 mg microencapsulated omeprazole per caplet | 24.0 mEq or 700 mg Mg(OH)$_2$<br>7.1 mEq or 600 mg NaHCO$_3$<br>31.1 mEq or 1300 mg total buffer | 100 mg diclofenac per tablet | 60 mg sucralose<br>60 mg Ac-Di-Sol<br>60 mg pregelatinized starch<br>30 mg Klucel<br>27 mg grape flavor<br>15 mg magnesium stearate<br>1 mg Red #40 Lake<br>1 mg Blue #2 Lake |
| 30 mg microencapsulated lansoprazole per caplet | 17.1 mEq or 500 mg Mg(OH)$_2$<br>5 mEq or 420 mg NaHCO$_3$<br>22.1 mEq or 920 mg total buffer | 200 mg microencapsulated asprin per tablet | 60 mg sucralose<br>60 mg Ac-Di-Sol<br>70 mg pregelatinized starch<br>30 mg Klucel<br>25 mg cherry flavor<br>15 mg magnesium stearate<br>3 mg Red #40 Lake |
| 60 mg microencapsulated omeprazole per caplet | 15 mEq or 750 mg Ca(OH)$_2$<br>15 mEq or 1260 mg NaHCO$_3$<br>30 mEq or 2010 mg total buffer | 100 mg ketoprofen per tablet | 60 mg sucralose<br>60 mg Ac-Di-Sol<br>60 mg pregelatinized starch<br>30 mg Klucel<br>25 mg cherry flavor<br>15 mg magnesium stearate<br>3 mg Red #40 Lake |
| 40 mg microencapsulated omprazole per tablet | 15 mEq or 750 mg Ca(OH)$_2$<br>10 mEq or 840 mg NaHCO$_3$<br>25 mEq or 1590 mg total buffer | 100 mg aspirin per tablet | 60 mg sucralose<br>60 mg Ac-Di-Sol<br>60 mg pregelatinized starch<br>30 mg Klucel<br>15 mg mint flavor<br>15 mg magnesium stearate |

Example 5

Preparation of Capsule Containing Microencapsulated Omeprazole

Various capsules are manufactured using the microencapsulate materials described in Examples 1 and 2. The amount of microencapsulated omeprazole used in each capsule batch is based on the actual payload of each set of microcapsules to achieve the theoretical dose. All ingredients are mixed well to achieve a homogenous bulk blend which is then filled into a hard gelatin capsule such as a size 00 hard gelatin capsule from Capsugel.

| PPI | Buffering Agent | Prokinetic Agent | Excipient |
|---|---|---|---|
| 15 mg microencapsulated lansoprazole per capsule | 17.1 mEq or 500 mg Mg(OH)$_2$<br>3.0 mEq or 250 mg NaHCO$_3$<br>20.1 mEq or 750 mg total buffer | 5 mg Mosapride per capsule | 30 mg Ac-Di-Sol<br>15 mg Klucel<br>7 mg magnesium stearate |
| 40 mg microencapsulated omeprazole per capsule | 15.4 mEq or 450 mg Mg(OH)$_2$<br>2.4 mEq or 200 mg NaHCO$_3$ | 10 mg Norcisapride per capsule | 30 mg Ac-Di-Sol<br>7 mg magnesium stearate |

-continued 17.8 mEq or 650 mg total buffer

| PPI | Antacid | Excipient |
|---|---|---|
| 40 mg microencapsulated omeprazole per capsule | 600 mg Mg(OH)$_2$<br>200 mg NaHCO$_3$<br>23.0 mEq or 800 mg total buffer | 50 mg Ac-Di-Sol<br>50 mg Klucel<br>5 mg magnesium stearate |
| 15 mg microencapsulated lansoprazole per capsule | 17.1 mEq or 500 mg Mg(OH)$_2$<br>3.0 mEq or 250 mg NaHCO$_3$<br>20.1 mEq or 750 mg total buffer | 50 mg Ac-Di-Sol<br>15 mg Klucel<br>7 mg magnesium stearate<br>6.0% disintegrant |
| 20 mg microencapsulated omeprazole per capsule | 20.6 mEq or 600 mg Mg(OH)$_2$<br>3.0 mEq or 250 mg NaHCO$_3$<br>23.6 mEq or 850 mg total buffer | 50 mg Ac-Di-Sol<br>50 mg Klucel<br>10 mg magnesium stearate<br>5.1% disintegrant |
| 15 mg microencapsulated lansoprazole per capsule | 17.1 mEq or 500 mg Mg(OH)$_2$<br>3.0 mEq or 250 mg NaHCO$_3$<br>20.1 mEq or 750 mg total buffer | 60 mg Ac-Di-Sol<br>15 mg Klucel<br>7 mg magnesium stearate<br>7.1% disintegrant |
| 15 mg microencapsulated lansoprazole per capsule<br>Size 1 capsule | 6.9 mEq or 200 mg Mg(OH)$_2$<br>2.6 mEq or 220 mg NaHCO$_3$<br>9.5 mEq or 420 mg total buffer | 35 mg Ac-Di-Sol<br>20 mg Klucel<br>6 mg magnesium stearate<br>7.1% disintegrant |
| 40 mg microencapsulated omeprazole per capsule | 15.4 mEq or 450 mg Mg(OH)$_2$<br>2.4 mEq or 200 mg NaHCO$_3$<br>17.8 mEq or 650 mg total buffer | 30 mg Ac-Di-Sol<br>7 mg magnesium stearate |
| 15 mg microencapsulated lansoprazole per capsule | 6.9 mEq or 200 mg Mg(OH)$_2$<br>2.6 mEq or 220 mg NaHCO$_3$<br>9.5 mEq or 420 mg total antacid | 35 mg Ac-Di-Sol<br>20 mg Klucel<br>6 mg magnesium stearate<br>Size 1 capsule |
| 10 mg microencapsulated omeprazole per capsule | 3.4 mEq or 100 mg Mg(OH)$_2$<br>3.0 mEq or 250 mg NaHCO$_3$<br>6.4 mEq or 350 mg total antacid | 18 mg Ac-Di-Sol<br>15 mg Microcrystalline Cellulose (MCC, PH102)<br>7 mg magnesium stearate<br>Size 2 capsule |
| 40 mg microencapsulated omeprazole per capsule | 3.4 mEq or 100 mg Mg(OH)$_2$<br>2.4 mEq or 200 mg NaHCO$_3$<br>5.8 mEq or 300 mg total antacid | 20 mg Ac-Di-Sol<br>5 mg magnesium stearate<br>Size 2 capsule |

| PPI | Buffering Agent | NSAID | Excipient |
|---|---|---|---|
| 15 mg microencapsulated lansoprazole per capsule | 17.1 mEq or 500 mg Mg(OH)$_2$<br>3.0 mEq or 250 mg NaHCO$_3$<br>20.1 mEq or 750 mg total buffer | 75 mg ketoprofen per capsule | 30 mg Ac-Di-Sol<br>15 mg Klucel<br>7 mg magnesium stearate |
| 40 mg microencapsulated omeprazole per capsule | 15.4 mEq or 450 mg Mg(OH)$_2$<br>2.4 mEq or 200 mg NaHCO$_3$<br>17.8 mEq or 650 mg total buffer | 100 mg enteric coated aspirin per capsule | 30 mg Ac-Di-Sol<br>7 mg magnesium stearate |

Example 6

Analytical Assay for Determining the Amount of Omeprazole Present in Tablets Containing Omeprazole Microspheres The following procedure was used to determine the potency of omeprazole in the tablets. The tablet was accurately weighed and placed into 100 ml volumetric flask. To that, 1.0 ml of Nanopure water was added to wet and soften the tablet. The solution was allowed to stand for 30 minutes. After sitting, the sample was vortexed and sonicated for 30 minutes or until completely dissolved 1.0 ml of chloroform was then added and the sample was vortexed and sonicated for an additional 15 minutes. The solution was then brought to volume with methanol and vortexed again to mix solution. 10 ml was then decanted into a 10 cc syringe fitted with a 0.45-micron filter. The material was pushed through the filter and the first several milliliters were discarded. The remaining mixture was then collected for HPLC injection. A 5-point calibration curve was prepared in methanol ranging from 15 to 300 µg/ml. The following chromatographic conditions were used: mobile phase: 75.5% Na$_2$PO$_4$, pH=8.0, 24.5% acetonitrile; flow rate: 1.0 mL/min; injection volume: 20 µL; detector: UV, 280 nm; column: waters symmetry shield RP8.

Example 7

Stability Study of Microencapsulated Omeprazole

Microspheres that exhibited dissolution results with greater than 80% omeprazole release after 2 hours were placed on stability. The microspheres were stored in opened vials at 25° C. All samples showed degradation after 4 weeks at elevated temperatures. The open vials stored at 25° C. were analyzed after 6-8 weeks for potency and for impurities using the Omeprazole EP method. The stability results are summarized in the table 7A below.

TABLE 7A

| Sample | Omeprazole Loading (Initial) | 4-Week Potency Values (Omeprazole Loading) | AUC Purity* |
|---|---|---|---|
| 5 | 23.3 | 25.0(107% of initial) @25° C. | 95.65 |
| 6 | 26.0 | 24.9(95.8% of initial) @25° C. | 99.90 |
| 8 | 24.8 | 26.4(106.6% of initial) @25° C. | 99.95 |
| 10 | 2.2 | 2.3(106% of initial) @25° C. | 76.16 |
| 11 | 20.5 | 22.6(110% of initial) @25° C. | 100.0 |
| 13 | 26.2 | 23.8(90.8% of initial) @25° C. | 99.54 |
| 14 | 21.3 | 19.1(89.5% of initial) @25° C. | 98.88 |
| 15 | 26.0 | 22.8(87.8% of initial) @25° C. | 99.70 |
| 17 | 25.8 | 21.9(84.9% of initial) @25° C. | 98.22 (99.3@$T_0$) |
| 23 | 22.2 | 20.7(93.2% of initial) @25° C. | 97.69 |
| 35 | 26.0 | 21.7(83.6% of initial) @25° C. | 97.88 |

*AUC Purity = Area Under the Curve after 6-8 weeks at 25° C. in open container.

Example 8

Method for Determining Payload of Omeprazole Microspheres

The HPLC samples for the omeprazole assay of various microspheres were prepared as follows: 5 mg of the microsphere were accurately weighed into a screw cap culture tube. To that, 200 μL of chloroform was added. The microspheres were allowed to dissolve, sonicated and vortex for approximately one minute. Then, 10 ml of methanol was added and the sample was again vortexed for one minute. Once completed, an aliquot of the sample was removed for HPLC analysis.

A 5-point calibration curve was prepared in methanol ranging from 20 to 500 μg/mL to calculate payload. The chromatographic conditions were: Mobile phase: 75.5% $Na_2PO_4$ pH 8.0, 24.5% Acetonitrile; Flow Rate: 1.0 mL/min; Run Time: 15 min; Injection Volume: 20 μL; Detector: U.V., 280 nm; Column: Waters SymmetryShield RP8.

Example 9

Method for Determining the Amount of Impurities Present in the Microspheres

The HPLC samples for the omeprazole assay of various microspheres were prepared in the following manner: 5 mgs of the omeprazole microspheres were weighed into a screw cap culture tube. To that, 200 μL of chloroform were added. The microspheres were allowed to dissolve, sonicate and vortex for approximately one minute each. 10 mL of methanol was then added and the sample was again vortexed for 1 minute. Once complete, an aliquot was removed for HPLC analysis.

For standards, 100 μg/mL concentration of omeprazole in methanol for a marker was prepared. A 0.1 μg/mL concentration of omeprazole was then prepared to set one-half the minimal detection limit. Then, a 1 μg/mL concentration of omeprazole impurity D in methanol was prepared. The chromatographic conditions were: Mobile Phase: 75% $Na_2PO_4$ pH 7.6, 25% acetonitrile; Flow Rate: 1.0 mL/min; Run Time: 30 min; Injection Volume: 20 μL; Detector: U.V., 280 nm; Column: Waters SymmetryShield RP8.

Example 10

Method for Determining Dissolution of Omeprazole Microspheres

The omeprazole potency method was used for the dissolution testing. The HPLC samples for the omeprazole assay of various microspheres were prepared according to the following method. 5 mgs of the microspheres were accurately weighed into an 8 ounce amber bottle. To that, 100 ml of pH 7.4 monobasic phosphate buffer was added. The samples were placed in a 37° C. water bath and vigorously shaken until the end of the release study. Using an Eppendorf pipette, 100 μL was removed and the outside part of the tip was rinsed with 100 μL of buffer back into the sample bottle. The sample was then transferred into a limited insert for HPLC analysis using a 1 cc syringe fitted with a 45 micron filter. Samples were then taken at 30, 45, and 120 minutes.

A 6-point calibration curve was prepared in diluent (70% sodium phosphate pH 10.0/30% acetonitrile) ranging from 1 to 120 μg/mL to determine sample release rates. The chromatographic conditions were: Mobile phase: 75.5% $Na_2PO_4$ pH 8.0, 24.5% Acetonitrile; Flow Rate: 1.0 mL/min; Run Time: 15 min; Injection Volume: 20 μL; Detector: U.V., 280 nm; Column: Waters SymmetryShield RP8.

Example 11

Optical Microscopy

The omeprazole microspheres were observed using an Olympus BX60 optical microscope equipped with an Olympus DP10 digital camera to determine their particle size and morphology characteristics. The microspheres were observed at either 100× or 200× magnification.

The microspheres prepared by spray drying were in the size range of 5 to 30 microns. The microspheres prepared by spinning disk-solvent process were in the size range of 25 to 100 microns. The microspheres prepared by spinning disk-hot melt process were in the size range of 30 to 125 microns.

Example 12

Thermal Gravimetric Analysis (TGA)

Thermal Gravimetric Analysis was performed on neat omeprazole (Two lots from Uquifa and USP Standard) and the omeprazole microspheres using a TA Instruments Model 2950 equipped with Thermal Solutions Instrument Software and Universal Analysis Data Software. The neat omeprazole samples showed very little weight loss up to 150° C. at which temperature a dramatic weight loss begins. This weight loss occurs at the melting point of omeprazole which is in the range of 150-160° C.

For the omeprazole microspheres, the percent weight loss up to 140° C. was recorded to determine the amount of volatiles present. Most samples exhibit a weight loss of less than 1% up to 140° C. except the samples that contained sodium bicarbonate which have a greater weight loss, from 7-32%. The following TGA run conditions were used: nitrogen atmosphere; Isothermal for 5 minutes at 25° C.; ramp 10° C./minute to 250° C.; platinum sample pan.

Example 13A

Formulation of Placebo Antacid Tablet Used in Example 13G

Antacid tablet without any omeprazole was prepared using the components listed in the table below. All ingredients were blended homogeneously in 1 cubic feet V-blender. The resulting blend was compressed into a tablet using a Stokes 16 station rotary tablet press equipped with plain, round ¾", FFBE punches.

| Ingredients | % Level | Mg/tab |
|---|---|---|
| Sodium Bicarbonate, USP #2 | 39.9 | 850 |
| Magnesium Hydroxide, spray dried (95% w/w) | 29.6 | 632 |
| Hydroxypropyl Cellulose (Klucel ®) | 5.1 | 110 |
| Croscarmellose Sodium (Ac-Di-Sol ®) | 2.1 | 45 |
| Xylitab ® 100 | 12.7 | 270 |
| Sucralose ® | 5.4 | 115 |
| Peach Durarome | 2.5 | 53 |
| Masking Flavor | 1.6 | 35 |
| Magnesium Stearate | 1.0 | 22 |
| TOTALS: | 100.0 | 2132 |

Example 13B

Preparation of SAN-15A Used in Example 13G

Micronized, non-microencapsulated omeprazole chewable tablets were prepared using the components listed in the table. All ingredients were blended homogeneously in 1 cubic feet V-blender. The resulting blend was compressed into a tablet using a Stokes 16 station rotary tablet press equipped with plain, round ¾", FFBE punches.

| Ingredients | % Level | Mg/tab |
|---|---|---|
| Omeprazole, USP (micronized) | 1.9 | 40.8 |
| Sodium Bicarbonate, USP #2 | 39.1 | 850 |
| Magnesium Hydroxide, spray dried (95% w/w) | 29.0 | 632 |
| Hydroxypropyl Cellulose (Klucel ®) | 5.1 | 110 |
| Croscarmellose Sodium (Ac-Di-Sol ®) | 2.1 | 45 |
| Xylitab ® 100 | 12.2 | 270 |
| Sucralose ® | 5.3 | 115 |
| Peach Flavor | 2.4 | 53 |
| Masking Flavor | 1.6 | 35 |
| Magnesium Stearate | 1.0 | 22 |
| FD&C Red Lake #40 | 0.1 | 3 |
| TOTALS: | 100.0 | 2176 |

Example 13C

Preparation of SAN-15B Used in Example 13G

Microencapsulated omeprazole powder (40 mg) prepared in Example 1C was co-administered with the antacid chewable tablet prepared in Example 13A (total ANC of 30.7 mEq). The powder and the placebo chewable tablet were chewed together in the mouth to simulate administration of 40 mg of microencapsulated omeprazole incorporated in the said placebo tablet.

Example 13D

Preparation of SAN-15C Used in Example 13G

Microencapsulated omeprazole powder (40 mg) prepared in Example 1D was co-administered with an antacid chewable tablet prepared in Example 13A (total ANC of 30.7 mEq). The powder and the placebo chewable tablet were chewed together in the mouth to simulate administration of 40 mg of microencapsulated omeprazole incorporated in the said placebo tablet.

Example 13E

Preparation of SAN-20D Used in Example 13G

Microencapsulated omeprazole powder prepared in Example 1C was blended homogeneously with other ingredients shown in the table. The powder blend was then compressed into a capsule shaped tablet using a Stokes rotary press.

| | SAN-20D | |
|---|---|---|
| Ingredients | mg/cap | % |
| Microencapsulated Omeprazole (28% w/w) | 142.86 | 14.1% |
| Sodium Bicarbonate #2 | 280 | 27.7% |
| Magnesium Hydroxide (95%) | 473.68 | 46.9% |
| Croscarmellose Sodium | 50 | 4.9% |
| Hydroxypropyl Cellulose | 55 | 5.4% |
| Magnesium Stearate | 9 | 0.9% |
| Total Fill Wt: | 1010.5 | 100% |

Example 13F

Preparation of SAN-20E Used in Example 13G

Microencapsulated omeprazole powder prepared in Example 1C was blended homogeneously with other ingredients shown in the table. The powder blend was then compressed into a capsule shaped tablet using a Stokes rotary press.

| | SAN-20E | |
|---|---|---|
| Ingredients | mg/cap | % |
| Microencapsulated Omeprazole (28% w/w) | 142.86 | 13.7% |
| Sodium Bicarbonate #2 | 280 | 26.9% |
| Magnesium Hydroxide (95%) | 473.68 | 45.4% |
| Croscarmellose Sodium | 82 | 7.9% |
| Hydroxypropyl Cellulose | 55 | 5.3% |
| Magnesium Stearate | 9 | 0.9% |
| Total Fill Wt: | 1042.5 | 100% |

Example 13G

Pharmacokinetic Study of Non-Enteric Coated Omeprazole 40 mg Chewable Tablets and Prilosec® Delayed-Release Capsules 40 mg This trial was conducted as an open-label, single-dose, crossover trial, with each subject receiving up to twelve different oral omeprazole formulations, one in each of the twelve treatment periods. Each dose was followed by a minimum 7-day washout. Omeprazole was administered at a dose of 40 mg. The compositions administered are set forth in Examples 13A-13F and Table 13.G.1. All formulations were administered with about 120 ml (4 oz) of water after an overnight fast and 1 hour prior to a standardized, high-fat breakfast. Within a given treatment period, the same treatment was administered to all subjects. The non-enteric coated formulation study drugs were compared to Prilosec® which contained enteric-coated granules.

TABLE 13.G.1

The pharmacokinetic release trial with omeprazole dosage forms.
(All dosage forms contained 40 mg omeprazole)

| Period | Study Material |
|---|---|
| 1 | Prilosec (40 mg omeprazole) |
| 3 (SAN-15A) | SAN-15A Tablet, 30.7 mEq (850 mg SB & 600 mg MH) 40 mg "Non-microencapsulated" OME & MS95 MH |
| 5 (SAN-15B) | Placebo Antacid Tablet, 30.7 mEq (850 mg SB & 600 mg MH) with 40 mg microencapsulated omeprazole with Klucel shell material |
| 7 (SAN-15C) | Placebo Antacid Tablet, 30.7 mEq (850 mg SB & 600 mg MH) with 40 mg microencapsulated omeprazole with Methocel shell material |
| 10 (SAN-20D) | SAN-20D Caplet, 18.8 mEq (280 mg SB & 450 mg MH) 40 mg microencapsulated omeprazole |
| 12 (SAN-20E) | SAN-20E Caplet, 18.8 mEq (280 mg SB & 450 mg MH) 40 mg microencapsulated omeprazole |

Volunteers were screened for up to 14 days before baseline measurements of blood plasma levels of omeprazole. In each period, a standardized high-fat breakfast was given in the clinic 1 hour after dosing of omeprazole. Blood samples for determination of plasma omeprazole concentrations were collected for 12 hours post treatment.

This trial was designed to assess the pharmacokinetics of immediate-release omeprazole chewable tablets and caplets versus the Prilosec® 40 mg delayed-release formulation. The duration of the trial for each subject was approximately 24 weeks, including up to 14 days for screening and a minimum 7 day wash-out period between omeprazole doses. Data from 12 healthy male subjects were expected to provide adequate power to assess pharmacokinetics and safety using descriptive statistics. The descriptive statistics were assessed using the pharmacokinetic parameters: Tmax, Cmax, AUC(0-t), and AUC(0-inf).

The treatments administered to subjects in this trial are listed in Table 13.G.1, above. In general, the treatment protocol entailed a 14 day assessment period, followed by a first period (Period 1) in which Prilosec® 40 mg delayed release capsule was administered to the subjects, after an overnight fast, and 1 hour prior to a standardized high-fat breakfast. Plasma sampling was conducted for 6 hour post-dose. Period 1 was followed by a 7-14 day washout period, during which the plasma levels of omeprazole were expected to decrease to a steady baseline. The other periods listed in Tablet 13.G.1 were conducted in a similar manner to Period 1, except substituting a dosage form according to the invention for the delayed-release formulation used in Period 1.

Pharmacokinetic Sampling, Analytical Methods, and Parameters

Blood samples (3 mL) were obtained by venipuncture within 30 minutes before each dose and at 0, 5, 10, 15, 20, 30, 45, 60, 90, 120, 180, 240, 300, 360 minutes (6 hours) after delivery of each dose during each trial period. Zero time was the time that the subject swallowed a capsule, caplet or chewable tablet of trial drug.

Plasma omeprazole concentrations were measured using a previously validated liquid chromatography mass spectrometry (LC-MSIMS) assay (MDS Pharma Services, Lincoln, Nebr.). The linear assay range was 5.0 to 750 ng/mL. The following pharmacokinetic parameters were measured for each subject:

Plasma omeprazole concentration at each sampling time

Peak omeprazole plasma concentration (Cmax) and the time at which Cmax is observed (Tmax) obtained directly from the data without interpolation Terminal elimination rate constant (Kel) determined from a log-linear regression analysis of the terminal plasma omeprazole concentrations Half-life of drug elimination (T ½) calculated as 0.693/Kel Area under the plasma drug time-concentration curve calculated from 0 time to last time point evaluated [AUC (0-t)] calculated using the trapezoidal rule with the plasma concentration at time t being the last measurable concentration Area under the plasma drug time-concentration curve calculated from 0 time and extrapolated to infinity [AUC (0-inf)] calculated as AUC(0-t)+Ct/Kel, where Ct is the last measurable plasma concentration (at time t) and Kel is the terminal elimination rate constant defined above.

Pharmacokinetic Analysis

For the analysis of data collected on Day 1 of each period (pre-meal dosing), an analysis of variance (ANOVA) model was used to test the bioequivalence of each of the tested drug formulations. The model included the following factors: treatment, period, sequence, and subject nested within sequence. Ninety percent confidence intervals (CIs) for treatment differences were calculated; the endpoints of these CIs were then reverse transformed to represent CIs about the percent mean ratios on the original scale. With respect to AUC(0-inf) and Cmax, equivalence was declared for each parameter if the bounds of the 90% CIs for the percent mean ratio, comparing a composition according to the invention (Periods 2-12) with Prilosec, were between 80% and 125%.

Pharmacokinetic Results

Figure 3:
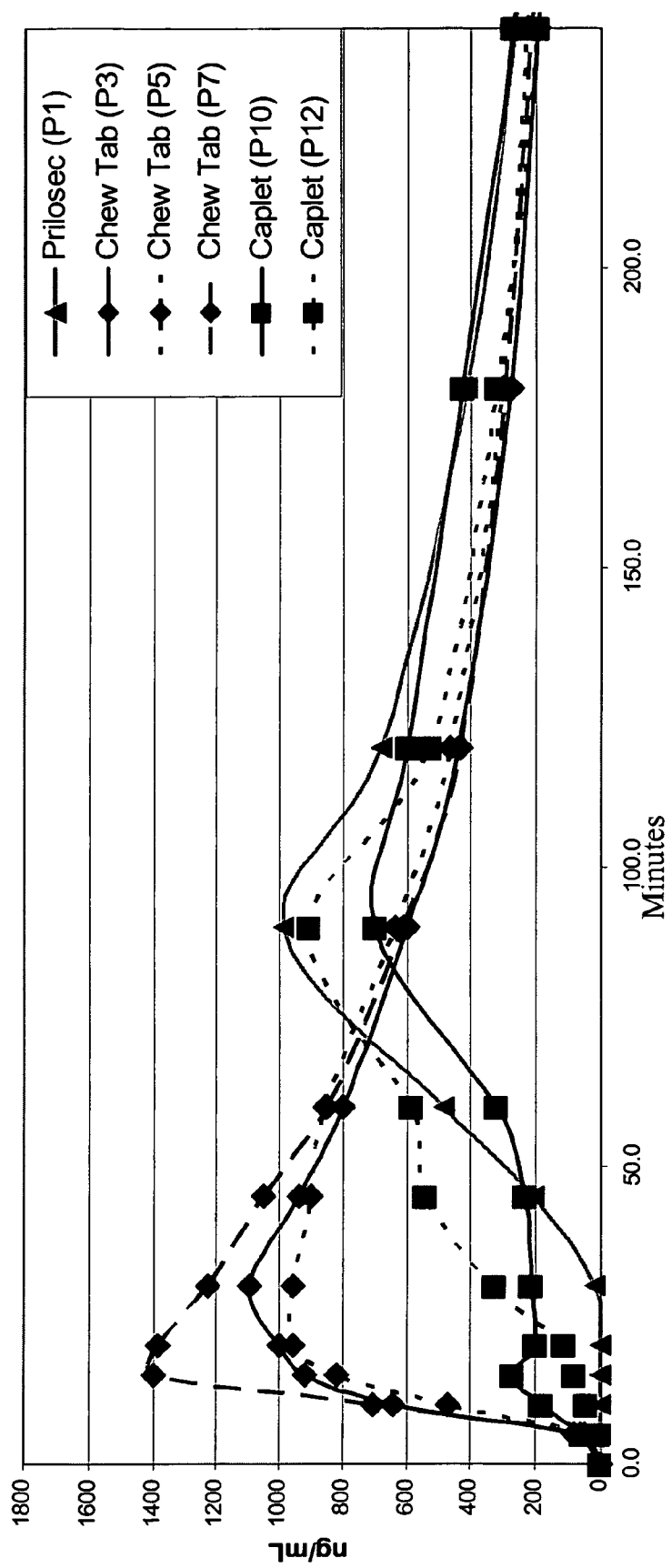
FIG. 3 is a graph comparing the average pharmacokinetic release profiles of SAN-15A, SAN-15B, SAN-15C, SAN-20D and SAN-20E as compared to Priolosec® brand enteric coated omeprazole 40 mg. Formulations were prepared as described in Example 13.
Figure 4:
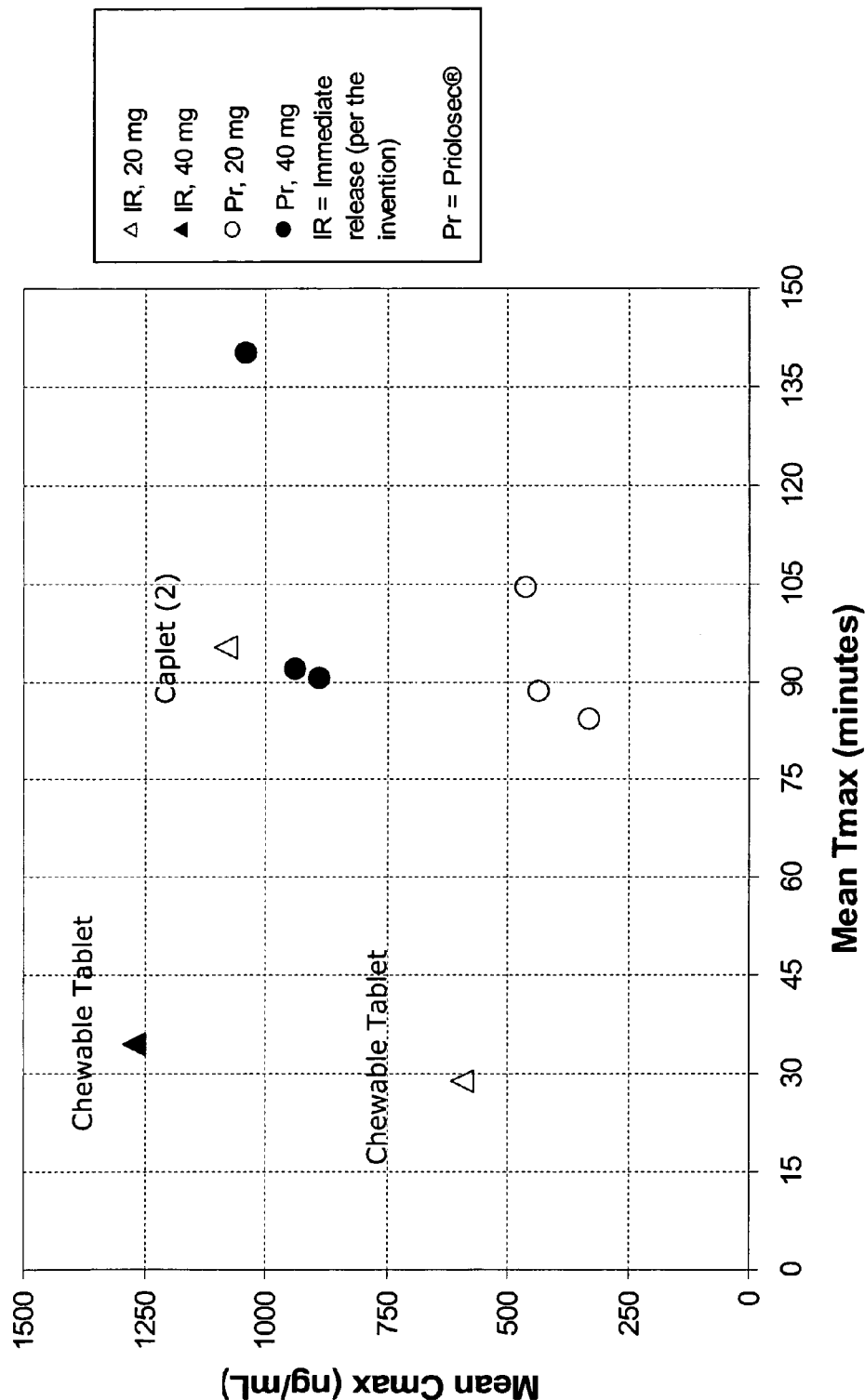
FIG. 4 is a graph comparing the mean peak plasma concentration (Cmax) versus the time at which Cmax is observed (Tmax) for SAN-15 (20 mg and 40 mg), SAN-20D, SAN-20E and Priolosec® brand enteric coated omeprazole 20 mg and 40 mg, Day 1. The data is from the human clinical trial described in Examples 14B and 15B.
Figure 5:
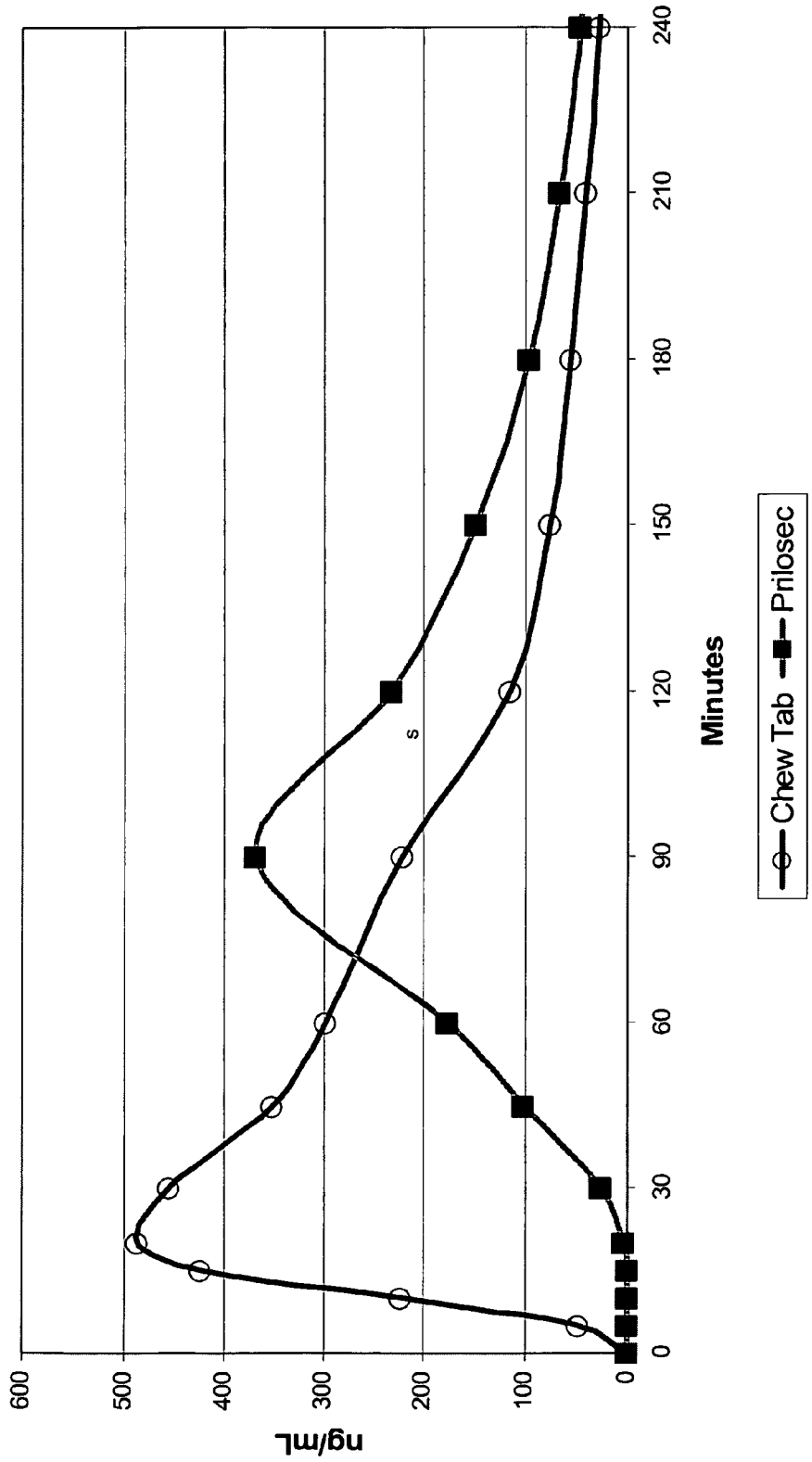
FIG. 5 is a graph comparing the average pharmacokinetic release profiles for SAN-15 20 mg and Priolosec® brand enteric coated omeprazole 20 mg, Day 1. The data is from the human clinical trial described in Examples 14B.
Figure 6:
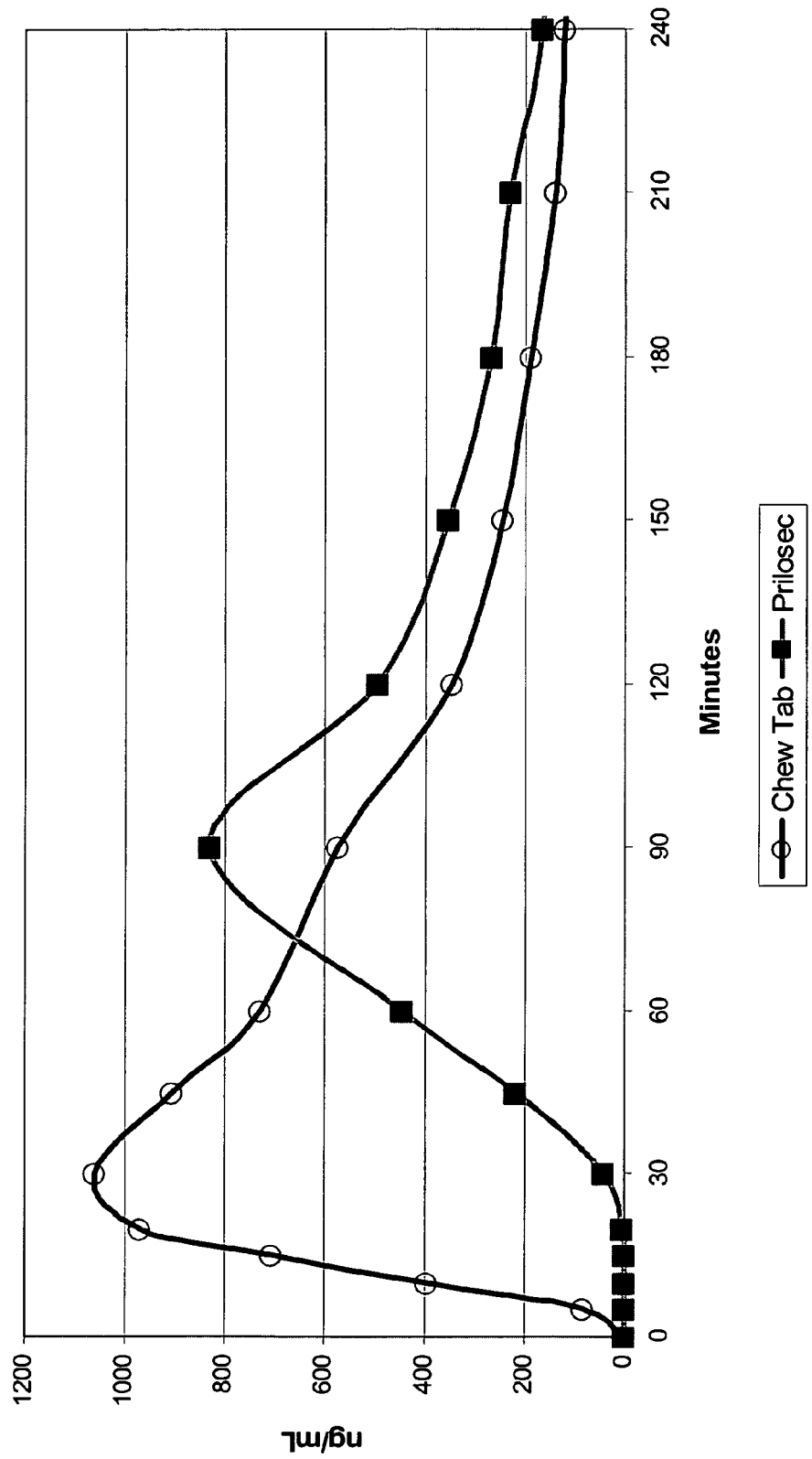
FIG. 6 is a graph comparing the average pharmacokinetic release profiles for SAN-15 40 mg and Priolosec® brand enteric coated omeprazole 40 mg, Day 1. The data is from the human clinical trial described in Examples 15B.
Figure 7:
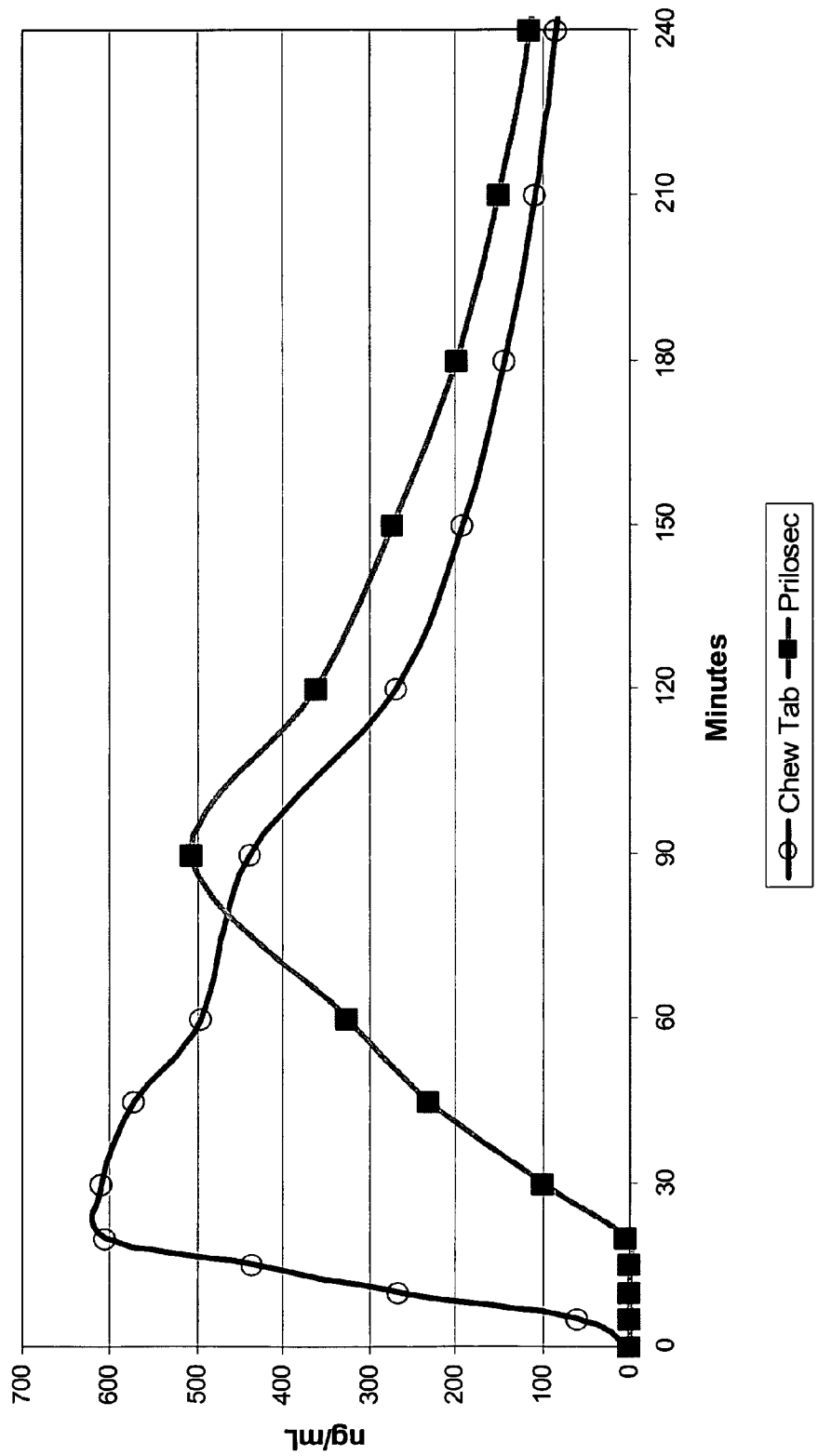
FIG. 7 is a graph comparing the average pharmacokinetic release profiles for SAN-15 20 mg and Priolosec® brand enteric coated omeprazole 20 mg, Day 7. The data is from the human clinical trial described in Examples 14B.
Figure 8:
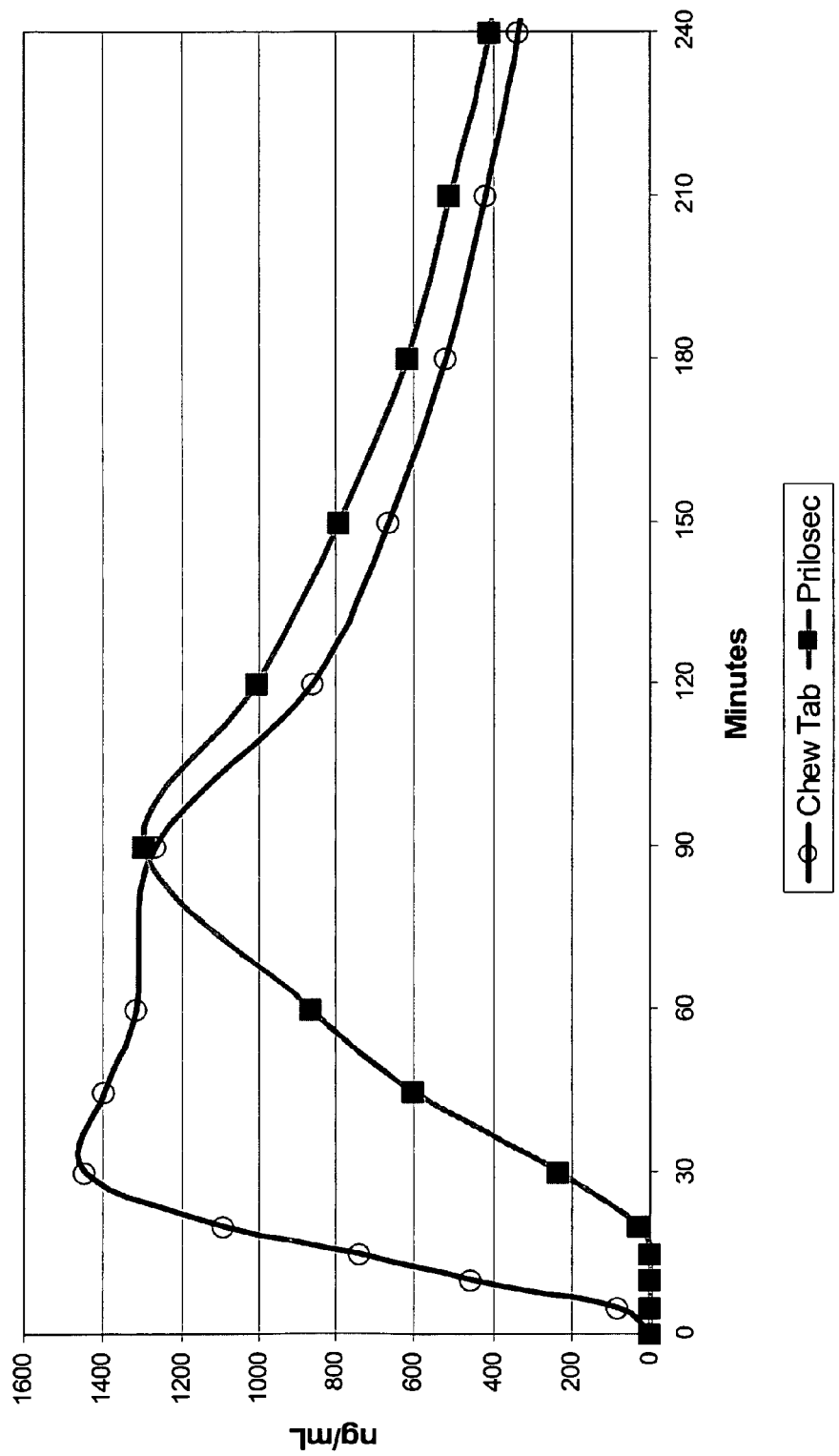
FIG. 8 is a graph comparing the average pharmacokinetic release profiles for SAN-15 40 mg and Priolosec® brand enteric coated omeprazole 40 mg, Day 7. The data is from the human clinical trial described in Examples 15B.
Figure 9:
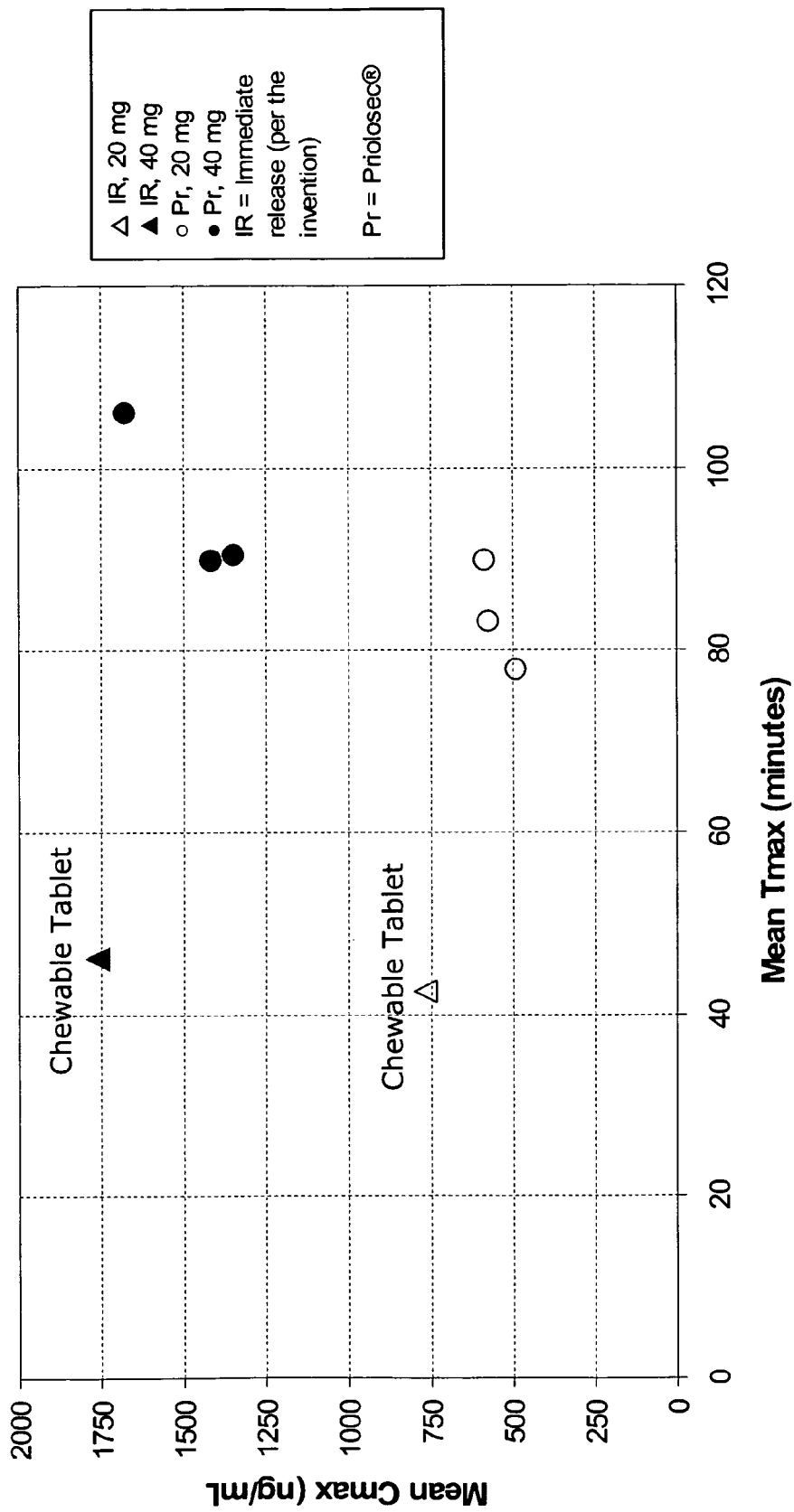
FIG. 9 is a graph comparing the mean peak plasma concentration (Cmax) versus the time at which Cmax is observed (Tmax) for SAN-15 (20 mg and 40 mg) and Priolosec® brand enteric coated omeprazole 20 mg and 40 mg, Day 7. The data is from the human clinical trial described in Examples 14B and 15B.
Figure 10:
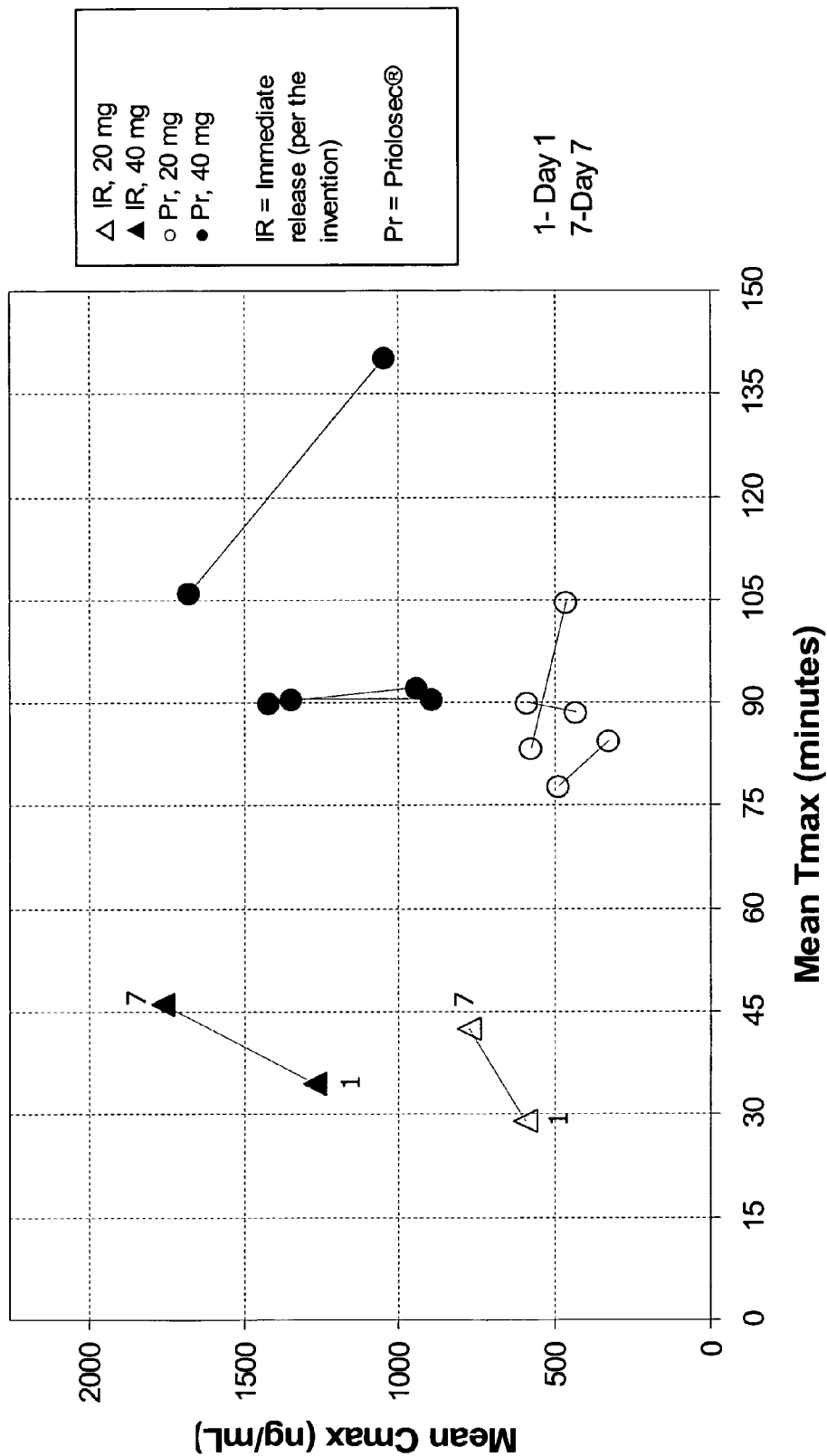
FIG. 10 is a graph comparing the mean peak plasma concentration (Cmax) versus the time at which Cmax is observed (Tmax) for SAN-15 (20 mg and 40 mg) and Priolosec® brand enteric coated omeprazole 20 mg and 40 mg, Day 1 and Day 7. The data is from the human clinical trial described in Examples 14B and 15B.

Pharmacokinetic results for this study are presented in Table 13.G.2 and FIGS. 3-10.

TABLE 13.G.2

| ng/mL | Period | Day | Intervals (Minutes) | | | | | | | |
|---|---|---|---|---|---|---|---|---|---|---|
| | | | 0 | 5 | 10 | 15 | 20 | 30 | 45 | 60 |
| Mean | Prilosec (P1) | 1 | 0 | 0 | 0 | 0 | 0 | 2 | 20 | 205 | 485 |
| Min | | 1 | 0 | 0 | 0 | 0 | 0 | 0 | 0 | 37 | 104 |
| Max | | 1 | 0 | 0 | 0 | 0 | 0 | 15 | 80 | 543 | 1474 |
| Mean | Chew Tab (P3) (SAN-15A) | 1 | 0 | 80 | 642 | 921 | 1001 | 1092 | 939 | 800 |
| Min | | 1 | 0 | 0 | 73 | 149 | 188 | 177 | 145 | 132 |
| Max | | 1 | 0 | 352 | 1321 | 1779 | 2073 | 2705 | 2571 | 2311 |
| Mean | Chew Tab (P5) (SAN-15B) | 1 | 0 | 53 | 473 | 820 | 956 | 958 | 897 | 856 |
| Min | | 1 | 0 | 0 | 36 | 330 | 428 | 379 | 227 | 167 |
| Max | | 1 | 0 | 150 | 1073 | 1770 | 2110 | 2327 | 2848 | 3097 |

TABLE 13.G.2-continued

| | | | | | | | | | | | |
|---|---|---|---|---|---|---|---|---|---|---|---|
| Mean | Chew Tab (P7) (SAN-15C) | 1 | 0 | 65 | 706 | 1396 | 1386 | 1230 | 1048 | 852 | |
| Min | | 1 | 0 | 0 | 191 | 473 | 711 | 515 | 321 | 226 | |
| Max | | 1 | 0 | 382 | 1172 | 2807 | 2306 | 2580 | 2358 | 2117 | |
| Mean | Caplet (P10) (SAN-20D) | 1 | 0 | 56 | 184 | 269 | 199 | 213 | 235 | 322 | |
| Min | | 1 | 0 | 0 | 5 | 23 | 28 | 49 | 48 | 56 | |
| Max | | 1 | 0 | 440 | 1256 | 1518 | 744 | 595 | 469 | 1013 | |
| Mean | Caplet (P12) (SAN-20E) | 1 | 0 | 5 | 43 | 81 | 116 | 327 | 540 | 583 | |
| Min | | 1 | 0 | 0 | 8 | 38 | 64 | 46 | 36 | 50 | |
| Max | | 1 | 0 | 30 | 98 | 135 | 199 | 1507 | 1687 | 1856 | |

| ng/mL | Period | Day | 90 | 120 | 180 | 240 | 300 | 360 | N | Cmax (ng/mL) | Tmax (hr) |
|---|---|---|---|---|---|---|---|---|---|---|---|
| Mean | Prilosec (P1) | 1 | 991 | 679 | 417 | 265 | 203 | 143 | 12 | 1061 | 1.38 |
| Min | | 1 | 241 | 127 | 37 | 8 | 8 | 0 | 12 | 273 | 1.00 |
| Max | | 1 | 2994 | 2146 | 1596 | 1093 | 1081 | 707 | 12 | 2994 | 1.50 |
| Mean | Chew Tab (P3) | 1 | 597 | 441 | 280 | 193 | 129 | 95 | 12 | 1201 | 0.54 |
| Min | | 1 | 71 | 42 | 9 | 0 | 0 | 0 | 12 | 196 | 0.50 |
| Max | | 1 | 2133 | 1701 | 1322 | 999 | 709 | 587 | 12 | 2705 | 1.50 |
| Mean | Chew Tab (P5) | 1 | 633 | 467 | 305 | 226 | 148 | 122 | 12 | 1192 | 0.50 |
| Min | | 1 | 70 | 29 | 14 | 7 | 0 | 0 | 12 | 428 | 0.17 |
| Max | | 1 | 2586 | 2058 | 1532 | 1279 | 788 | 744 | 12 | 3097 | 1.00 |
| Mean | Chew Tab (P7) | 1 | 610 | 436 | 295 | 217 | 161 | 112 | 11 | 1550 | 0.33 |
| Min | | 1 | 67 | 31 | 7 | 0 | 0 | 0 | 11 | 711 | 0.25 |
| Max | | 1 | 2244 | 1538 | 1279 | 1069 | 760 | 596 | 11 | 2807 | 0.50 |
| Mean | Caplet (P10) | 1 | 699 | 598 | 430 | 271 | 178 | 136 | 8 | 111 | 1.59 |
| Min | | 1 | 143 | 97 | 42 | 21 | 10 | 6 | 8 | 531 | 0.25 |
| Max | | 1 | 1440 | 1850 | 1404 | 1036 | 749 | 633 | 8 | 1850 | 3.00 |
| Mean | Caplet (P12) | 1 | 909 | 531 | 320 | 196 | 143 | 110 | 8 | 1083 | 1.59 |
| Min | | 1 | 93 | 111 | 28 | 10 | 0 | 0 | 8 | 159 | 0.75 |
| Max | | 1 | 1951 | 1315 | 1099 | 795 | 648 | 553 | 8 | 1951 | 3.00 |

Example 14A

Preparation of SAN-15 20 mg Chewable Tablets

Microencapsulation of Omeprazole

Omeprazole was microencapsulated as described in Example 1B.

Preparation of Chewable Tablet

An omeprazole pre-blend containing microencapsulated omeprazole, antacid excipients and other formulation components was prepared. A flavor pre-blend containing sensory components was then prepared. The main blend was then prepared by combining the omeprazole and flavor pre-blends. Magnesium stearate was then added to the main blend and mixed to form a final blend. All blending operations were carried out in appropriately sized V-blenders. Blend uniformity was ensured by testing at various stages of blending. The final blend was then compressed on a high speed rotary tablet press to form the final tablets. The tablet press was a Stokes® instrumented tablet press using less than a full set of tablet tooling in order to conserve powder. A compression force of 50 kN using ¾" round FFBE tooling gave an acceptable tablet harness and friability in all prototype batches. The amount of each component is listed below in Table 14.A.2.

TABLE 14.A.2

| Ingredient | Quantity/20 mg Tablet |
|---|---|
| Microencapsulated Omeprazole | 55.6 mg* |
| Sodium Bicarbonate | 600 mg |
| Magnesium Hydroxide (95% w/w) | 736.8 mg** |
| Hydroxypropyl Cellulose | 90 mg |
| Croscarmellose Sodium | 33 mg |
| Xylitol | 200 mg |
| Sucralose | 80 mg |
| Peach Durarome | 52 mg |
| Peppermint Durarome | 10 mg |
| Masking Flavor | 27 mg |

TABLE 14.A.2-continued

| Ingredient | Quantity/20 mg Tablet |
|---|---|
| Magnesium Stearate | 17 mg |
| Red #40 Lake Dye | 2 mg |
| Total Weight/Unit | 1902 mg |

*Spray-dried omeprazole (37% w/w) includes a 2% omeprazole overage in the blend manufacture that helps ensure label claim amount of omeprazole in the final product
**Spray-dried magnesium hydroxide (95% w/w with 5% starch) equivalent to 700 mg of active magnesium hydroxide Example 14B Clinical Trial with SAN-15 (20 mg) Chewable Tablet The primary objective was to show that SAN-15 20 mg Chewable Tablets are pharmacokinetically bioequivalent to Prilosec 20 mg with respect to area under the curve.

This was an open-label, randomized, 2-period crossover trial to evaluate the pharmacokinetics, pharmacodynamics, and safety of seven consecutive daily doses of SAN-15 chewable tablets (omeprazole immediate-release chewable tablets) 20 mg compared to seven consecutive daily doses of Prilosec Delayed-Release Capsules 20 mg in healthy subjects. A comparison of pharmacokinetic parameters for SAN-15 chewable tablets administered before versus after a meal was also conducted.

Volunteers were screened within 21 days before baseline measurements (e.g. gastric pH, vital signs). Gastric pH was recorded for 24 hours before the first dose of trial drug. In Period 1, subjects received SAN-15 chewable tablets 20 mg or Prilosec 20 mg, as randomized, 1 hour before breakfast for seven consecutive days. A standardized high-fat breakfast was given in the clinic 1 hour after dosing on Days 1 and 7, or 1 hour after water for baseline assessment. Standardized lunch and dinner were also given 5 and 10 hours post dose at Baseline and on Days 1 and 7 in the clinic. Blood samples to determine plasma omeprazole concentrations were collected for 12 hours and gastric pH was measured for 24 hours after the doses on Days 1 and 7. Subjects who had received SAN-15 chewable tablets 20 mg in Period 1 were given an eighth dose on Day 8 in Period 1, 1 hour after the start of the standardized high-fat breakfast. Blood samples were collected for 12 hours after the eighth dose. After a 10- to 14-day washout period, subjects returned for Period 2 and received the alternate treatment from that received in Period 1. Procedures in Period 2 were identical to those in Period 1 except that no eighth dose of SAN-15 chewable tablets 20 mg was given.

Number of Subjects: Thirty-five subjects were dosed and 34 subjects completed the trial. Thirty-four subjects were included in the pharmacokinetic analyses and 29 subjects were included in the pharmacodynamic analyses for Days 1 and 7.

Treatments: The treatments administered to subjects are listed in the table below:

| Treatment | Treatment Description |
|---|---|
| SAN-15 | SAN-15 chewable tablets (omeprazole immediate-release chewable tablets) 20 mg to be administered orally and chewed for 30 seconds, followed by drinking 120 mL water each morning after an overnight fast, 1 hour before starting breakfast. |
| Prilosec | Prilosec Capsules (omeprazole delayed-release capsules) 20 mg to be administered orally with 120 mL water each morning after an overnight fast, 1 hour before starting breakfast. |

Pharmacokinetic Sampling, Analytical Methods, and Parameters

Blood samples (3 mL) were obtained by venipuncture on Days 1 and 7 of both periods and Day 8 of Period 1 (for SAN-15 chewable tablets) within 30 minutes before each dose, and at 5, 10, 15, 20, 30, 45, 60, 90, 120, 150, 180, 210, 240, 300, 360, 420, 480, 540, 600, 660, and 720 minutes (12 hours) after each dose. Zero time was the time that the subject ingested a chewable tablet or swallowed a capsule of Prilosec.

Plasma omeprazole concentrations were measured using a validated liquid chromatography mass spectrometry (LC-MS/MS) assay (MDS Pharma Services, Lincoln, Nebr.). The linear assay range was 5.0 to 750 ng/mL. The following pharmacokinetic parameters were measured for each subject:

Plasma omeprazole concentration at each sampling time
Peak omeprazole plasma concentration (Cmax) and the time at which Cmax is observed (Tmax) obtained directly from the data without interpolation
Terminal elimination rate constant (kel) determined from a log-linear regression analysis of the terminal plasma omeprazole concentrations
Half-life of drug elimination (T ½) calculated as 0.693/Kel
Area under the plasma drug time-concentration curve from 1 time to last time point evaluated [AUC(0-t)] calculated using the trapezoidal rule with the plasma concentration at time "t" being the last measurable concentration
Area under the plasma drug time-concentration curve from 1 time and extrapolated to infinity [AUC(0-inf)] calculated as AUC(0-t)+Ct/Kel, where Ct is the last measurable plasma concentration and Kel is the terminal elimination rate constant defined above.

The Pharmacokinetic results are shown below in Tables 14.B. and 14.C.

TABLE 14B

SAN-15 Chewable Tablets 20 mg

| ng/mL | Day | \multicolumn{11}{c}{Interval (Minutes)} |
|---|---|---|---|---|---|---|---|---|---|---|---|---|
|  |  | 0 | 5 | 10 | 15 | 20 | 30 | 45 | 60 | 90 | 120 | 150 |
| Mean | 1 | 0 | 48 | 223 | 423 | 487 | 455 | 351 | 298 | 221 | 116 | 77 |
| Min | 1 | 0 | 0 | 21 | 36 | 80 | 94 | 91 | 55 | 22 | 8 | 0 |
| Max | 1 | 0 | 336 | 646 | 1150 | 1420 | 1270 | 1280 | 1200 | 1100 | 618 | 499 |
| Mean | 7 | 0 | 60 | 266 | 435 | 606 | 610 | 572 | 496 | 437 | 268 | 191 |
| Min | 7 | 0 | 0 | 30 | 74 | 129 | 152 | 170 | 158 | 55 | 21 | 10 |
| Max | 7 | 0 | 386 | 1120 | 1620 | 2010 | 1590 | 1510 | 1310 | 1230 | 696 | 548 |

| ng/mL | Day | \multicolumn{11}{c}{Interval (Minutes)} | N | Cmax (ng/mL) | Tmax (hr) |
|---|---|---|---|---|---|---|---|---|---|---|---|---|---|---|---|
|  |  | 180 | 210 | 240 | 300 | 360 | 420 | 480 | 540 | 600 | 660 | 720 |  |  |  |
| Mean | 1 | 55 | 40 | 28 | 15 | 9 | 6 | 4 | 2 | 1 | 1 | 1 | 34 | 594 | 0.48 |
| Min | 1 | 0 | 0 | 0 | 0 | 0 | 0 | 0 | 0 | 0 | 0 | 0 | 34 | 117 | 0.17 |
| Max | 1 | 421 | 347 | 276 | 179 | 131 | 87 | 62 | 40 | 26 | 17 | 12 | 34 | 1420 | 1.50 |
| Mean | 7 | 144 | 108 | 83 | 49 | 29 | 16 | 11 | 6 | 4 | 2 | 22 | 34 | 769 | 0.71 |
| Min | 7 | 6 | 0 | 0 | 0 | 0 | 0 | 0 | 0 | 0 | 0 | 00 | 34 | 198 | 0.17 |
| Max | 7 | 478 | 404 | 361 | 262 | 196 | 139 | 104 | 75 | 53 | 43 | 31 | 34 | 2010 | 1.50 |

TABLE 14C

Prilosec Delayed-Release Capsules 20 mg

| ng/mL | Day | \multicolumn{11}{c}{Interval (Minutes)} |
|---|---|---|---|---|---|---|---|---|---|---|---|---|
|  |  | 0 | 5 | 10 | 15 | 20 | 30 | 45 | 60 | 90 | 120 | 150 |
| Mean | 1 | 0 | 0 | 0 | 0 | 3 | 26 | 103 | 176 | 367 | 232 | 149 |
| Min | 1 | 0 | 0 | 0 | 0 | 0 | 0 | 0 | 0 | 0 | 35 | 17 |
| Max | 1 | 0 | 0 | 0 | 5 | 91 | 459 | 513 | 1180 | 1580 | 719 | 552 |
| Mean | 7 | 0 | 0 | 0 | 1 | 5 | 100 | 232 | 325 | 506 | 360 | 273 |

TABLE 14C-continued

| | | | | | | Prilosec Delayed-Release Capsules 20 mg | | | | | | |
|---|---|---|---|---|---|---|---|---|---|---|---|---|
| Min | 7 | 0 | 0 | 0 | 0 | 0 | 0 | 0 | 0 | 85 | 68 | 48 |
| Max | 7 | 0 | 0 | 0 | 11 | 83 | 1070 | 1180 | 1110 | 1740 | 1220 | 952 |

| | | Interval (Minutes) | | | | | | | | | | | Cmax | Tmax |
|---|---|---|---|---|---|---|---|---|---|---|---|---|---|---|
| ng/mL | Day | 180 | 210 | 240 | 300 | 360 | 420 | 480 | 540 | 600 | 660 | 720 | N | (ng/mL) | (hr) |
| Mean | 1 | 97 | 66 | 46 | 25 | 16 | 8 | 6 | 4 | 3 | 1 | 1 | 34 | 433 | 1.48 |
| Min | 1 | 7 | 0 | 0 | 0 | 0 | 0 | 0 | 0 | 0 | 0 | 0 | 34 | 107 | 0.33 |
| Max | 1 | 461 | 419 | 332 | 253 | 178 | 115 | 85 | 63 | 55 | 32 | 23 | 34 | 1580 | 2.50 |
| Mean | 7 | 198 | 149 | 115 | 67 | 40 | 25 | 15 | 10 | 4 | 4 | 3 | 34 | 583 | 1.50 |
| Min | 7 | 31 | 18 | 11 | 0 | 0 | 0 | 0 | 0 | 0 | 0 | 0 | 34 | 177 | 0.75 |
| Max | 7 | 667 | 583 | 530 | 363 | 263 | 195 | 146 | 104 | 74 | 65 | 44 | 34 | 1740 | 3.00 |

Example 15A

Preparation of SAN-15 40 mg Chewable Tablets

Microencapsulation of Omeprazole

Omeprazole was microencapsulated as described in Example 1B.

Preparation of Chewable Tablet

The procedure used to make SAN-15 40 mg Chewable Tablet was the same as the one described in Example 14A except that the following ingredients were used:

TABLE 15.A.2

| Ingredient | Quantity/40 mg Tablet |
|---|---|
| Microencapsulated Omeprazole | 110* |
| Sodium Bicarbonate | 600 mg |
| Magnesium Hydroxide (95% w/w) | 736.8 mg** |
| Hydroxypropyl Cellulose | 90 mg |
| Croscarmellose Sodium | 33 mg |
| Xylitol | 200 mg |
| Sucralose | 80 mg |
| Peach Durarome | 52 mg |
| Peppermint Durarome | 10 mg |

TABLE 15.A.2-continued

| Ingredient | Quantity/40 mg Tablet |
|---|---|
| Masking Flavor | 27 mg |
| Magnesium Stearate | 17 mg |
| Red #40 Lake Dye | 2 mg |
| Total Weight/Unit | 1902 mg |

*Spray-dried omeprazole (37% w/w) includes a 2% omeprazole overage in the blend manufacture that helps ensure label claim amount of omeprazole in the final product
**Spray-dried magnesium hydroxide (95% w/w with 5% starch) equivalent to 700 mg of active magnesium hydroxide Example 15B Clinical Trial with SAN-15 (40 mg) Chewable Tablet Trial design, design rationale, treatments, timing of dose for each subject, pharmacokinetic sampling, analytical methods, and parameters, and pharmacodynamic parameters and methodology were the same for this trial as was in the above Example 14.B with the exception of the use of SAN-15 40 mg chewable tablets and Prilosec Delayed-Release Capsules 40 mg in this trial verses 20 mg of each in the above example. The Pharmacokinetic results are shown below in Tables 15.B. and 15.C.

TABLE 15B

| | | SAN-15 Chewable Tablets 40 mg | | | | | | | | | |
|---|---|---|---|---|---|---|---|---|---|---|---|
| | | Intervals (Minutes) | | | | | | | | | |
| ng/mL | Day | 0 | 5 | 10 | 15 | 20 | 30 | 45 | 60 | 90 | 120 | 150 |
| Mean | 1 | 0 | 83 | 396 | 705 | 970 | 1062 | 907 | 727 | 575 | 349 | 244 |
| Min | 1 | 0 | 0 | 13 | 81 | 164 | 175 | 240 | 140 | 51 | 19 | 11 |
| Max | 1 | 0 | 885 | 1740 | 2170 | 2300 | 2470 | 2160 | 1940 | 1910 | 1600 | 1110 |
| Mean | 7 | 0 | 82 | 458 | 736 | 1090 | 1443 | 1394 | 1316 | 1266 | 857 | 662 |
| Min | 7 | 0 | 8 | 55 | 94 | 172 | 288 | 532 | 411 | 248 | 129 | 60 |
| Max | 7 | 10 | 304 | 1740 | 2010 | 2230 | 2970 | 2530 | 2450 | 2450 | 1840 | 1420 |

| | | Intervals (Minutes) | | | | | | | | | | | Cmax | Tmax |
|---|---|---|---|---|---|---|---|---|---|---|---|---|---|---|
| ng/mL | Day | 180 | 210 | 240 | 300 | 360 | 420 | 480 | 540 | 600 | 660 | 720 | N | (ng/mL) | (hr) |
| Mean | 1 | 189 | 141 | 120 | 83 | 45 | 32 | 24 | 18 | 12 | 9 | 7 | 35 | 1272 | 0.58 |
| Min | 1 | 0 | 0 | 0 | 0 | 0 | 0 | 0 | 0 | 0 | 0 | 0 | 35 | 403 | 0.25 |
| Max | 1 | 1180 | 881 | 1060 | 1040 | 445 | 414 | 399 | 329 | 237 | 197 | 163 | 35 | 2470 | 1.50 |
| Mean | 7 | 519 | 419 | 333 | 219 | 150 | 98 | 65 | 39 | 29 | 19 | 14 | 35 | 1763 | 0.77 |
| Min | 7 | 32 | 15 | 9 | 0 | 0 | 0 | 0 | 0 | 0 | 0 | 0 | 35 | 933 | 0.25 |
| Max | 7 | 1330 | 1160 | 920 | 755 | 589 | 458 | 338 | 277 | 211 | 148 | 137 | 35 | 2970 | 1.50 |

TABLE 15C

Prilosec Delayed-Release Capsules 40 mg

| ng/mL | Day | \multicolumn{11}{c}{Intervals (Minutes)} |
|---|---|---|---|---|---|---|---|---|---|---|---|---|
| | | 0 | 5 | 10 | 15 | 20 | 30 | 45 | 60 | 90 | 120 | 150 |
| Mean | 1 | 0 | 0 | 0 | 0 | 2 | 40 | 219 | 445 | 829 | 494 | 356 |
| Min | 1 | 0 | 0 | 0 | 0 | 0 | 0 | 0 | 10 | 45 | 34 | 40 |
| Max | 1 | 0 | 0 | 0 | 8 | 49 | 354 | 1200 | 1950 | 2210 | 1760 | 1650 |
| Mean | 7 | 1 | 1 | 1 | 1 | 28 | 232 | 600 | 862 | 1296 | 1005 | 790 |
| Min | 7 | 0 | 0 | 0 | 0 | 0 | 0 | 0 | 0 | 201 | 216 | 183 |
| Max | 7 | 18 | 15 | 16 | 15 | 748 | 1970 | 2050 | 2360 | 2510 | 2060 | 1810 |

| ng/mL | Day | \multicolumn{10}{c}{Intervals (Minutes)} | N | Cmax (ng/mL) | Tmax (hr) |
|---|---|---|---|---|---|---|---|---|---|---|---|---|---|---|
| | | 180 | 210 | 240 | 300 | 360 | 420 | 480 | 540 | 600 | 660 | 720 | | | |
| Mean | 1 | 267 | 231 | 166 | 118 | 84 | 53 | 36 | 27 | 22 | 16 | 12 | 35 | 938 | 1.54 |
| Min | 1 | 17 | 10 | 0 | 0 | 0 | 0 | 0 | 0 | 0 | 0 | 0 | 35 | 274 | 0.75 |
| Max | 1 | 1400 | 1330 | 1140 | 882 | 985 | 624 | 476 | 420 | 397 | 332 | 260 | 35 | 2210 | 3.50 |
| Mean | 7 | 615 | 507 | 408 | 282 | 189 | 129 | 85 | 60 | 42 | 28 | 20 | 35 | 1417 | 1.50 |
| Min | 7 | 116 | 66 | 37 | 14 | 6 | 0 | 0 | 0 | 0 | 0 | 0 | 35 | 408 | 0.50 |
| Max | 7 | 1370 | 1280 | 1060 | 855 | 600 | 505 | 390 | 327 | 278 | 200 | 218 | 35 | 2510 | 5.00 |

Example 16A

Preparation of Immediate Release Chewable Tablet Using Dry-Coated Omeprazole

Dry-coated omeprazole are prepared by mixing the ingredients listed in table 16A-1 and dry-granulate the powder using roller compactor. Resulting granules are screened through a 10-mesh screen.

Table 16A-1 Dry Granule Ingredient for Dry-Coated Omeprazole (20% w/w)

TABLE 16A-1

Dry Granule Ingredient for dry-coated omeprazole (20% w/w)

| | Mg/unit | % Level | Weight/batch |
|---|---|---|---|
| Omeprazole, USP (micronized) | 20 mg | 20.0% | 2.0 Kg |
| Sodium Bicarbonate, USP #2 | 30 mg | 30.0% | 3.0 Kg |
| Klucel (HPC) | 10 mg | 10.0% | 1.0 Kg |
| Xylitab 100 | 39.7 mg | 39.7% | 4.0 Kg |
| Magnesium Stearate | 0.3 mg | 0.3% | 0.03 Kg |
| Total Dry Coated API Granules | 100 mg | 100% | 10 Kg |

The dry granules are then mixed with the components shown in table 16A-2 until a homogeneous blend is obtained. This blend is then compressed using a 18 mm diameter tooling in a Stokes rotary press.

TABLE 16-A-2

Chewable Tablet using dry-coated omeprazole (40 mg dose)

| | Mg/unit | Weight/batch |
|---|---|---|
| Omeprazole Dry Granule (20% w/w) | 200 | 2.0 Kg |
| Sodium Bicarbonate, USP #2 | 390 | 3.9 Kg |
| Magnesium Hydroxide, 95% | 745.3 | 7.45 Kg |
| Klucel (HPC) | 80 | 0.8 Kg |
| Croscarmellose sodium | 28 | 0.28 Kg |
| Xylitab 100 | 151 | 1.51 Kg |
| Sucralose | 80 | 0.8 Kg |
| Masking Flavor | 30 | 0.3 Kg |
| Strawberry flavor | 60 | 0.6 Kg |
| Magnesium Stearate | 13 | 0.13 Kg |
| Total | 1777 | 17.77 Kg |

Example 16B

Preparation of Immediate Release Chewable Tablet Using Dry-Coated Omeprazole

Dry-coated omeprazole are prepared by mixing the ingredients listed in the table 16B-1 and dry-granulate the powder using roller compactor. Resulting granules are screened through a 10-mesh screen.

TABLE 16B-1

Dry Granule Ingredient for dry-coated omeprazole (10% w/w)

| | Mg/unit | % Level |
|---|---|---|
| Omeprazole | 10 mg | 10.0% |
| Sodium Bicarbonate | 25 mg | 25.0% |
| Klucel (HPC) | 10 mg | 10.0% |
| Xylitab 100 | 54.7 mg | 54.7% |
| Magnesium Stearate | 0.3 mg | 0.3% |
| Total Dry Coated API Granules | 100 mg | 100% |

The dry granules are then mixed with the components shown in table 16B-2 until a homogeneous blend is obtained. This blend is then compressed using a 18 mm diameter tooling in a Stokes rotary press.

TABLE 16-B-2

Chewable Tablet using dry-coated omeprazole (40 mg dose)

| | Mg/unit | Weight/batch |
|---|---|---|
| Omeprazole Dry Granule (10% w/w) | 400 | 2.0 Kg |
| Sodium Bicarbonate, USP #2 | 380 | 1.9 Kg |

TABLE 16-B-2-continued

Chewable Tablet using dry-coated omeprazole (40 mg dose)

| | Mg/unit | Weight/batch |
|---|---|---|
| Magnesium Hydroxide, 95% | 745.3 | 3.73 Kg |
| Klucel (HPC) | 60 | 0.3 Kg |
| Croscarmellose sodium | 28 | 0.14 Kg |
| Xylitab 100 | 11 | 0.06 Kg |
| Sucralose | 80 | 0.4 Kg |
| Masking Flavor | 30 | 0.15 Kg |
| Chocolate flavor | 70 | 0.35 Kg |
| Magnesium Stearate | 13 | 0.07 Kg |
| Total | 1817 | 9.09 Kg |

Example 16C

Preparation of Immediate Release Caplet Using Dry-Coated Omeprazole

Dry-coated omeprazole are prepared by mixing the ingredients listed in the table 16C-1 and dry-granulate the powder using roller compactor. Resulting granules are screened through a 10-mesh screen.

TABLE 16C-1

Dry Granule Ingredient for dry-coated omeprazole (10% w/w)

| | Mg/unit | % Level |
|---|---|---|
| Omeprazole, USP (micronized) | 10 mg | 10% |
| Sodium Bicarbonate | 85 mg | 85% |
| Klucel (HPC) | 5 mg | 5% |
| Magnesium Stearate | 0.3 mg | 0.3% |
| Total Dry Coated API Granules | 100.3 mg | 100% |

The dry granules prepared in Example 16C-1 are mixed with the ingredients shown in Table 16C-2 until a homogeneous blend is obtained. This blend is then compressed using oval-shaped tooling in a Stokes rotary press.

TABLE 16-C-2

Caplet using dry-coated omeprazole (40 mg dose)

| | Mg/unit | Weight/batch |
|---|---|---|
| Omeprazole Dry Granule (10% w/w) | 400 | 4 Kg |
| Sodium Bicarbonate, USP #2 | 160 | 1.6 Kg |
| Magnesium Oxide, USP | 280 | 2.8 Kg |
| Klucel (HPC) | 10 | 0.1 Kg |
| Croscarmellose sodium | 65 | 0.65 Kg |
| Magnesium Stearate | 8 | 0.08 Kg |
| Total | 923 | 9.23 Kg |

Many modifications, equivalents, and variations of the present invention are possible in light of the above teachings, therefore, it is to be understood that within the scope of the appended claims, the invention may be practiced other than as specifically described.

What is claimed is:

1. A solid pharmaceutical composition having an enhanced shelf-life, comprising:
   (a) about 1 to about 120 mg of omeprazole, or a free base, free acid, salt, enantiomer, isomer, or tautomer, thereof, in combination with sodium bicarbonate, wherein said combination is microencapsulated with a material that enhances the shelf-life of the pharmaceutical composition comprising at least one cellulose hydroxypropyl ether; and
   (b) about 1 to about 160 mEq of antacid comprising sodium bicarbonate wherein the pharmaceutical composition is not enteric coated and has less than 5% total new impurities after 1 year of storage at room temperature.

2. The pharmaceutical composition according to claim 1, wherein the antacid comprises at least one soluble buffer.

3. The pharmaceutical composition according to claim 2, wherein the soluble buffer is present in about 5 mEq to about 40 mEq.

4. The pharmaceutical composition according to claim 1 comprising about 500 to about 2000 mg of antacid.

5. The pharmaceutical composition according to claim 1, wherein the omeprazole has less than 1% degradation after one month of storage at room temperature.

6. The pharmaceutical composition according to claim 1 further comprising one or more excipients selected from the group consisting of parietal cell activators, organic solvents, erosion facilitators, flavoring agents, sweetening agents, diffusion facilitators, antioxidants and carrier materials selected from binders, suspending agents, disintegration agents, filling agents, surfactants, solubilizers, stabilizers, lubricants, wetting agents, diluents, anti-adherents, and antifoaming agents.

7. The pharmaceutical composition according to claim 6, wherein the flavoring agent comprises peach, menthol, aspartame, sucralose, xylitol, mint, sucrose, or a mixture thereof.

8. The pharmaceutical composition according to claim 1 in the form of a capsule, a chewable tablet, a tablet, or a powder.

9. The pharmaceutical composition according to claim 1, wherein the maximum serum concentration is reached within about 1 hour after administration of the pharmaceutical formulation to a subject.

10. The pharmaceutical composition according the claim 1, wherein the average particle size of the microencapsulated omeprazole is between about 20 to about 500 microns in diameter.

11. The pharmaceutical composition according the claim 1, wherein the average particle size of the microencapsulated proton pump inhibitor is between about 50 to about 150 microns in diameter.

12. A method of treating an acid related gastrointestinal disorder in a subject in need thereof by administering a pharmaceutical composition having an enhanced shelf-life, comprising:
   (a) about 1 to about 120 mg of omeprazole or a free base, free acid, salt, enantiomer, isomer, or tautomer thereof in combination with sodium bicarbonate, wherein said combination is microencapsulated with a material that enhances the shelf-life of the pharmaceutical composition wherein the material that enhances the shelf-life of the pharmaceutical formulation comprising at least one cellulose hydroxypropyl ether; and
   (b) about 1 to about 160 mEq of at least one antacid comprising sodium bicarbonate; wherein the pharmaceutical composition is not enteric coated and has less than 5% total new impurities after 1 year of storage at room temperature.

13. The pharmaceutical composition according to claim 1, wherein a serum concentration of the omeprazole is about 0.3 μg/ml within about 45 minutes after administration of the pharmaceutical formulation to a subject.

14. The pharmaceutical composition according to claim 1, wherein a serum concentration of the omeprazole is about 0.45 μg/ml within about 30 minutes after administration of the pharmaceutical formulation to a subject.

15. The pharmaceutical composition according to claim 1, wherein a serum concentration of the omeprazole is about 0.1 μg/ml within about 15 minutes after administration of the pharmaceutical formulation to a subject.

16. The pharmaceutical composition according to claim 1, wherein about 50% of the omeprazole is released from the composition within about 1 hour after exposure to gastrointestinal fluid.

17. The pharmaceutical composition according to claim 1, wherein about 70% of the omeprazole is released from the composition within about 1.5 hours after exposure to gastrointestinal fluid.

18. The pharmaceutical composition according to claim 1, wherein a maximum serum concentration is reached within about 45 minutes after administration of the pharmaceutical formulation to a fasting subject.

19. The pharmaceutical composition according to claim 1, wherein the antacid is present in an amount of about 1 mEq to about 3 mEq per mg of omeprazole.

20. The pharmaceutical composition according to claim 1, wherein the antacid is present in an amount of between about 5 mEq to about 60 mEq.

21. The pharmaceutical composition according to claim 1, wherein the material that enhances the shelf-life of the pharmaceutical formulation sufficiently dissolves in water in less than about 30 minutes.

22. The pharmaceutical composition according to claim 1, wherein the material that enhances the shelf-life of the pharmaceutical formulation sufficiently disintegrates to release the omeprazole into the gastrointestinal fluid within about 1 hour.

23. The pharmaceutical composition according to claim 1, wherein the drug loading of the omeprazole into microspheres is about 20 wt-% of omeprazole to microencapsulated omeprazole.

24. The pharmaceutical composition according to claim 1, wherein the drug loading of the omeprazole into microspheres is between about 10 wt-% to about 60 wt-% of omeprazole to microencapsulated omeprazole.

25. A chewable tablet, comprising:
(a) between about 1 to about 120 mg of omeprazole, or a free base, free acid, salt, enantiomer, isomer, or tautomer thereof in combination with sodium bicarbonate, wherein said combination is microencapsulated with a material that enhances the shelf-life of the chewable tablet comprising cellulose hydroxypropyl ether;
(b) between about 1 mEq and about 160 mEq of antacid comprising sodium bicarbonate; and
(c) at least one flavoring agent; wherein the pharmaceutical composition is not enteric coated and has less than 5% total new impurities after 1 year of storage at room temperature;
wherein upon administration of the chewable tablet to a fasted subject, the maximum serum concentration of the omeprazole is reached within about 45 minutes after administration.

26. The chewable tablet according to claim 25, wherein the flavoring agent comprises peach, menthol, aspartame, sucralose, sucrose, xylitol, mint, or a mixture thereof.

27. The chewable tablet according to claim 25, wherein a serum concentration of the omeprazole is about 0.5 μg/ml within about 1 hour after administration of the pharmaceutical formulation to a subject.

28. The chewable tablet according to claim 25, wherein about 70% of the omeprazole is released from the composition within about 1.5 hours after exposure to gastrointestinal fluid.

29. The chewable tablet according to claim 25, wherein the antacid is present in an amount of about 1.0 mEq to about 3 mEq per mg of omeprazole.

30. The chewable tablet according to claim 25, wherein the antacid comprises sodium bicarbonate, sodium carbonate, calcium carbonate, magnesium oxide, potassium bicarbonate, magnesium hydroxide, magnesium, carbonate, and mixtures thereof.

31. The chewable tablet according to claim 25, wherein the drug loading of the proton pump inhibitor into microspheres is about 20 wt-% of omeprazole to microencapsulated omeprazole.

32. The chewable tablet according to claim 25, wherein the drug loading of the omeprazole into microspheres is between about 10 wt-% to about 60 wt-% of omeprazole to microencapsulated omeprazole.

* * * * *